US012699321B2

(12) United States Patent
Omatsu et al.

(10) Patent No.: US 12,699,321 B2
(45) Date of Patent: Aug. 4, 2026

(54) COMPOUND, (CO)POLYMER, COMPOSITION, METHOD FOR FORMING RESIST PATTERN, METHOD FOR PRODUCING COMPOUND, AND METHOD FOR PRODUCING (CO)POLYMER

(71) Applicant: Mitsubishi Gas Chemical Company, Inc., Tokyo (JP)

(72) Inventors: Tadashi Omatsu, Hiratsuka (JP); Masahiro Matsumoto, Niigata (JP); Michihiro Yuri, Niigata (JP); Kentaro Kataoka, Niigata (JP); Takashi Sato, Hiratsuka (JP); Masatoshi Echigo, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 584 days.

(21) Appl. No.: 17/924,521

(22) PCT Filed: May 12, 2021

(86) PCT No.: PCT/JP2021/018110
§ 371 (c)(1),
(2) Date: Nov. 10, 2022

(87) PCT Pub. No.: WO2021/230300
PCT Pub. Date: Nov. 18, 2021

(65) Prior Publication Data

US 2023/0174688 A1 Jun. 8, 2023

(30) Foreign Application Priority Data

May 15, 2020 (JP) ................................ 2020-085904

(51) Int. Cl.

| | |
|---|---|
| ***C08F 220/22*** | (2006.01) |
| ***C07C 67/24*** | (2006.01) |
| ***C07C 69/653*** | (2006.01) |
| ***C08F 8/12*** | (2006.01) |
| ***C08F 20/18*** | (2006.01) |
| ***C08F 20/26*** | (2006.01) |
| ***G03F 7/039*** | (2006.01) |

(52) U.S. Cl.
CPC ............ *G03F 7/0397* (2013.01); *C07C 67/24* (2013.01); *C07C 69/653* (2013.01); *C08F 8/12* (2013.01); *C08F 20/18* (2013.01); *C08F 20/26* (2013.01); *C08F 220/22* (2013.01); *G03F 7/039* (2013.01)

(58) Field of Classification Search
CPC ...................................................... C08F 12/24
See application file for complete search history.

(56) References Cited

U.S. PATENT DOCUMENTS

| | | | |
|---|---|---|---|
| 2,100,798 | A | 11/1937 | Dilthey |
| 2,546,872 | A | 3/1951 | Schmid |
| 2,587,437 | A | 2/1952 | Bralley |
| 3,947,468 | A | 3/1976 | Hall |
| 4,017,627 | A | 4/1977 | Sturm |
| 4,252,884 | A | 2/1981 | Bennett |
| 4,289,839 | A | 9/1981 | Dipippo |
| 4,482,489 | A | 11/1984 | Dipippo |
| 4,579,758 | A | 4/1986 | Dorsch |
| 5,332,648 | A | 7/1994 | Kihara |
| 5,986,094 | A | 11/1999 | Ghoshal |
| 6,784,228 | B2 | 8/2004 | Ogura |
| 6,794,408 | B2 | 9/2004 | Eder |
| 7,871,751 | B2 | 1/2011 | Echigo |
| 9,122,153 | B2 | 9/2015 | Echigo |
| 9,136,121 | B2 | 9/2015 | Hatakeyama |

(Continued)

FOREIGN PATENT DOCUMENTS

| | | |
|---|---|---|
| CN | 1414031 | 4/2003 |
| CN | 1853141 | 10/2006 |

(Continued)

OTHER PUBLICATIONS

Machine translation of JP 2015-161823 (no date) (Year: 0000).*

(Continued)

*Primary Examiner* — Amanda C. Walke
(74) *Attorney, Agent, or Firm* — Fitch, Even, Tabin & Flannery LLP

(57) ABSTRACT

An iodine-containing (meth)acrylate compound represented by formula (1):

(1)

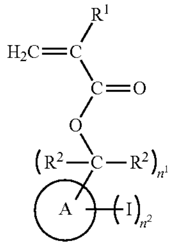

wherein $R^1$ represents a hydrogen atom, methyl, or halogen; each $R^2$ independently represents a hydrogen atom, a linear organic group having 1 to 20 carbon atoms, a branched organic group having 3 to 20 carbon atoms, or a cyclic organic group having 3 to 20 carbon atoms; A represents an organic group having 1 to 30 carbon atoms; A contains at least one acyl group; $n^1$ represents 0 or 1; and $n^2$ represents an integer of 1 to 20.

15 Claims, No Drawings

(56) References Cited

U.S. PATENT DOCUMENTS

| | | | | |
|---|---|---|---|---|
| 9,274,426 | B2 | 3/2016 | Rahman | |
| 9,316,913 | B2 | 4/2016 | Echigo | |
| 9,540,339 | B2 | 1/2017 | Echigo | |
| 9,904,167 | B2 * | 2/2018 | Tsuchimura | C07C 327/22 |
| 9,908,831 | B2 | 3/2018 | Echigo | |
| 9,989,849 | B2 * | 6/2018 | Nakagawa | C08F 220/22 |
| 10,303,055 | B2 | 5/2019 | Sato et al. | |
| 10,377,734 | B2 | 8/2019 | Echigo | |
| 10,495,968 | B2 * | 12/2019 | Aqad | G03F 7/0392 |
| 10,915,021 | B2 * | 2/2021 | Fukushima | G03F 7/0045 |
| 2002/0106909 | A1 | 8/2002 | Kato | |
| 2003/0092852 | A1 | 5/2003 | Ogura | |
| 2004/0197709 | A1 | 10/2004 | Arase | |
| 2004/0229162 | A1 | 11/2004 | Ohsawa | |
| 2005/0074695 | A1 | 4/2005 | Nakamura | |
| 2005/0118749 | A1 | 6/2005 | Sakamoto et al. | |
| 2005/0255712 | A1 | 11/2005 | Kato et al. | |
| 2006/0094845 | A1 | 5/2006 | Yamamoto | |
| 2007/0059632 | A1 | 3/2007 | Oguro | |
| 2007/0172759 | A1 | 7/2007 | Ogihara | |
| 2007/0232839 | A1 | 10/2007 | Yoshitomo | |
| 2008/0113294 | A1 | 5/2008 | Echigo | |
| 2008/0138744 | A1 | 6/2008 | Hatanaka | |
| 2008/0153031 | A1 | 6/2008 | Echigo et al. | |
| 2009/0171061 | A1 | 7/2009 | Sue | |
| 2009/0246684 | A1 | 10/2009 | Kim | |
| 2009/0261300 | A1 | 10/2009 | Watanabe | |
| 2010/0047709 | A1 | 2/2010 | Echigo | |
| 2010/0081081 | A1 | 4/2010 | Enomoto et al. | |
| 2010/0099044 | A1 | 4/2010 | Hatakeyama | |
| 2010/0104977 | A1 | 4/2010 | Hatakeyama | |
| 2010/0136477 | A1 | 6/2010 | Ng | |
| 2010/0190107 | A1 | 7/2010 | Shibata | |
| 2010/0207516 | A1 | 8/2010 | Moriwaki | |
| 2010/0227859 | A1 | 9/2010 | Li | |
| 2010/0285407 | A1 | 11/2010 | Ogihara | |
| 2010/0316950 | A1 | 12/2010 | Oguro et al. | |
| 2011/0177459 | A1 | 7/2011 | Ogihara | |
| 2011/0230058 | A1 | 9/2011 | Sakamoto | |
| 2011/0274713 | A1 | 11/2011 | Burn | |
| 2011/0311920 | A1 | 12/2011 | Kinsho | |
| 2012/0064725 | A1 | 3/2012 | Kinsho | |
| 2012/0171611 | A1 | 7/2012 | Ideno et al. | |
| 2012/0184103 | A1 | 7/2012 | Ogihara | |
| 2012/0220112 | A1 | 8/2012 | Hatakeyama | |
| 2012/0228584 | A1 | 9/2012 | Wigglesworth | |
| 2013/0004896 | A1 | 1/2013 | Echigo | |
| 2013/0056653 | A1 | 3/2013 | Hatakeyama | |
| 2013/0056654 | A1 | 3/2013 | Hatakeyama | |
| 2013/0084705 | A1 | 4/2013 | Nakafuji | |
| 2013/0087529 | A1 | 4/2013 | Hatakeyama | |
| 2013/0150627 | A1 | 6/2013 | Okada | |
| 2014/0186776 | A1 | 7/2014 | Uchiyama | |
| 2014/0248556 | A1 | 9/2014 | Kato | |
| 2014/0248561 | A1 | 9/2014 | Echigo | |
| 2014/0308615 | A1 | 10/2014 | Echigo | |
| 2014/0319097 | A1 | 10/2014 | Kim | |
| 2014/0363768 | A1 | 12/2014 | Kinsho | |
| 2014/0363955 | A1 | 12/2014 | Hatakeyama | |
| 2014/0363957 | A1 | 12/2014 | Morishita | |
| 2014/0363958 | A1 | 12/2014 | Hatakeyama | |
| 2015/0030980 | A1 | 1/2015 | Echigo | |
| 2015/0037735 | A1 | 2/2015 | Yang | |
| 2015/0090691 | A1 | 4/2015 | Echigo | |
| 2015/0115199 | A1 | 4/2015 | Choi et al. | |
| 2015/0192851 | A1 | 7/2015 | Yamashita et al. | |
| 2015/0309403 | A1 | 10/2015 | Rahman | |
| 2015/0368224 | A1 | 12/2015 | Echigo | |
| 2015/0376157 | A1 | 12/2015 | Echigo | |
| 2015/0376158 | A1 | 12/2015 | Echigo | |
| 2015/0376202 | A1 | 12/2015 | Echigo | |
| 2016/0130243 | A1 | 5/2016 | Satou | |
| 2016/0145231 | A1 | 5/2016 | Echigo | |
| 2017/0183279 | A1 | 6/2017 | Echigo | |
| 2017/0242338 | A1 | 8/2017 | Hirano | |
| 2017/0349564 | A1 | 12/2017 | Toida | |
| 2018/0074402 | A1 | 3/2018 | Toida | |
| 2018/0074406 | A1 | 3/2018 | Toida | |
| 2018/0095368 | A1 | 4/2018 | Toida et al. | |
| 2018/0155472 | A1 | 6/2018 | Saha et al. | |
| 2018/0208703 | A1 | 7/2018 | Okada | |
| 2018/0246405 | A1 | 8/2018 | Kudo et al. | |
| 2018/0246409 | A1 | 8/2018 | Toida | |
| 2018/0284605 | A1 | 10/2018 | Aqad et al. | |
| 2019/0056657 | A1 | 2/2019 | Toida et al. | |
| 2019/0094690 | A1 | 3/2019 | Hatakeyama et al. | |
| 2019/0163065 | A1 | 5/2019 | Hatakeyama et al. | |
| 2019/0202955 | A1 | 7/2019 | Aqad et al. | |
| 2020/0026188 | A1 | 1/2020 | Maruyama | |
| 2020/0209747 | A1 * | 7/2020 | Hatakeyama | C08F 220/1809 |
| 2021/0018841 | A1 | 1/2021 | Sato et al. | |
| 2021/0116813 | A1 | 4/2021 | Sato et al. | |
| 2021/0206901 | A1 | 7/2021 | Sato et al. | |
| 2022/0119336 | A1 | 4/2022 | Omatsu et al. | |

FOREIGN PATENT DOCUMENTS

| | | | |
|---|---|---|---|
| CN | 1942825 | A | 4/2007 |
| CN | 101088046 | A | 12/2007 |
| CN | 101889247 | | 11/2010 |
| CN | 102070595 | | 5/2011 |
| CN | 103304385 | | 9/2013 |
| CN | 103717562 | A | 4/2014 |
| CN | 103733135 | A | 4/2014 |
| CN | 103733136 | | 4/2014 |
| CN | 103804196 | A | 5/2014 |
| CN | 10424885 | A | 12/2014 |
| CN | 104245885 | A | 12/2014 |
| CN | 104557552 | A | 4/2015 |
| CN | 104870438 | A | 8/2015 |
| CN | 105131161 | A | 12/2015 |
| CN | 107428717 | A | 12/2017 |
| CN | 107533291 | A | 1/2018 |
| CN | 108690164 | A | 10/2018 |
| CN | 110325916 | A | 10/2019 |
| EP | 1275673 | | 1/2003 |
| EP | 1300403 | | 4/2003 |
| EP | 1666970 | | 6/2006 |
| EP | 2743249 | | 6/2014 |
| EP | 2743769 | | 6/2014 |
| EP | 2743770 | A1 | 6/2014 |
| EP | 3279190 | | 2/2018 |
| JP | S48049508 | A | 7/1973 |
| JP | S61-060630 | A | 3/1986 |
| JP | 62094841 | A | 5/1987 |
| JP | S62191850 | A | 8/1987 |
| JP | H01283280 | | 11/1989 |
| JP | H04217675 | | 8/1992 |
| JP | H0519463 | | 1/1993 |
| JP | H05034913 | A | 2/1993 |
| JP | H05134415 | A | 5/1993 |
| JP | H05163290 | A | 6/1993 |
| JP | 05216235 | A | 8/1993 |
| JP | H06049402 | A | 2/1994 |
| JP | H06242607 | A | 9/1994 |
| JP | H07215833 | | 8/1995 |
| JP | H09-020721 | A | 1/1997 |
| JP | H09020721 | | 1/1997 |
| JP | H1025220 | | 1/1998 |
| JP | H10045764 | A | 2/1998 |
| JP | H11072925 | | 3/1999 |
| JP | 2001042525 | | 2/2001 |
| JP | 2002214769 | | 7/2002 |
| JP | 2002334869 | A | 11/2002 |
| JP | 2002334896 | | 11/2002 |
| JP | 2002341542 | | 11/2002 |
| JP | 2003201333 | | 7/2003 |
| JP | 2004177668 | A | 6/2004 |
| JP | 2004271838 | A | 9/2004 |
| JP | 2005250434 | A | 9/2005 |
| JP | 2005266741 | A | 9/2005 |
| JP | 2005326838 | A | 11/2005 |
| JP | 2005326868 | A | 11/2005 |
| JP | 2005346024 | A | 12/2005 |

(56) References Cited

FOREIGN PATENT DOCUMENTS

JP 2006036648 2/2006
JP 2006098869 4/2006
JP 2006113136 4/2006
JP 2006160663 6/2006
JP 2006213634 8/2006
JP 2006259482 A 9/2006
JP 2007019294 1/2007
JP 2007199653 8/2007
JP 2007226170 A 9/2007
JP 2007226204 A 9/2007
JP 2007262398 10/2007
JP 2007326847 12/2007
JP 2008065081 3/2008
JP 2008145539 A 6/2008
JP 2008201954 A 9/2008
JP 2008239868 10/2008
JP 2009073738 A 4/2009
JP 2009-098651 A 5/2009
JP 2009098155 A 5/2009
JP 2009108313 5/2009
JP 2009155256 7/2009
JP 2009173623 A 8/2009
JP 2009-275155 A 11/2009
JP 2009300978 12/2009
JP 2010160189 7/2010
JP 2010170013 8/2010
JP 2010219295 9/2010
JP 2010235643 10/2010
JP 2011068624 4/2011
JP 2011105887 6/2011
JP 2011150023 8/2011
JP 20121687 1/2012
JP 2012068652 4/2012
JP 2012077295 4/2012
JP 2012083731 A 4/2012
JP 2012145897 8/2012
JP 2013064978 A 4/2013
JP 2013068928 4/2013
JP 2013083833 A 5/2013
JP 2013083939 5/2013
JP 2013087173 A 5/2013
JP 2013137524 A 7/2013
JP 2013253161 A 12/2013
JP 2014196288 A 10/2014
JP 2014205746 10/2014
JP 2015018220 1/2015
JP 2015018221 1/2015
JP 2015018223 1/2015
JP 2015087115 A 5/2015
JP 2015514691 A 5/2015
JP 2015-108781 A 6/2015
JP 2015-110532 A 6/2015
JP 2015-516972 A 6/2015
JP 2015127821 7/2015
JP 2015161823 A * 9/2015 ............ G03F 7/325
JP 2018-013744 A 1/2018
JP 2018-095851 A 6/2018
JP 2018-172640 A 11/2018
JP 2019-061217 A 4/2019
JP 2019-101417 A 6/2019
JP 2020-106826 A 7/2020
JP 2004-029542 A 1/2024
JP 7579516 B2 11/2024
KR 20060071423 6/2006
KR 1020100095563 8/2010
KR 1020130025833 A 3/2013
KR 20130048307 A 5/2013
KR 1020140066161 5/2014
KR 1020140079358 6/2014
KR 1020140079359 6/2014
KR 10-2017-0133367 A 12/2017
KR 10-2018-0050665 A 5/2018
KR 10-2018-0111531 A 10/2018
KR 10-2019-0035543 A 4/2019
KR 10-2019-0126090 A 11/2019
TW 200519538 A 6/2005
TW 200918502 A 5/2009
TW 201204450 A 2/2012
TW 201321362 A 6/2013
TW 201321891 A 6/2013
TW 201321895 A 6/2013
TW 201329031 A 7/2013
TW 201446711 A 12/2014
TW 201446825 A 12/2014
TW 201723663 A 7/2017
TW 201837048 A 10/2018
TW 201921109 A 6/2019
TW 201930283 A 8/2019
WO 9736960 10/1997
WO 0214434 2/2002
WO 03017002 2/2003
WO 2004066377 A1 8/2004
WO 2005029189 A1 3/2005
WO 2005111724 11/2005
WO 2006068267 A1 6/2006
WO 2007097457 8/2007
WO 2008053974 A1 5/2008
WO 2008/105266 A1 9/2008
WO 2008137816 A2 11/2008
WO 2009072465 A1 6/2009
WO 2009119201 A1 10/2009
WO 2009145224 12/2009
WO 2011034062 A1 3/2011
WO 2012165507 A1 12/2012
WO 2013010102 1/2013
WO 2013024777 A1 2/2013
WO 2013024778 A1 2/2013
WO 2013024779 A1 2/2013
WO 2013066067 5/2013
WO 2013184755 12/2013
WO 2014050690 4/2014
WO 2014123032 A1 8/2014
WO 2014199660 12/2014
WO 2017/043561 A1 3/2017
WO 2018/180049 A1 10/2018
WO 2019151403 8/2019
WO 2019/208762 A1 10/2019
WO 2019208761 A1 10/2019
WO 2020/040161 A1 2/2020
WO WO2020/137935 A1 7/2020
WO 2021/029396 A1 2/2021

OTHER PUBLICATIONS

International Search Report for PCT/JP2021/018110, mailed Jul. 13, 2021, and English Translation submitted herewith (7 pages).

Shinji Okazaki et al., "Development of Lithography Technology in These 40 Years", S&T Publishing Inc., Dec. 9, 2016 (Cited in Specification).

Saha, Sourabh K. et al.; "Radiopaque Resists for Two-Photon Lithography to Enable Submicron 3D Imaging of Polymer Parts via X-ray Computed Tomography"; 2018; vol. 10; ACS Applied Materials & Interfaces; pp. 1164-1172.

Shinji Okazaki et al.; Development Lithography Technology in These 40 Years, S&T Publishing Inc.; Dec. 9, 2016.

Green, Ori et al.; "Near-Infrared Dioxetane Luminophores with Direct Chemiluminescence Emission Mode"; J. Am. Chem. Soc.; 2017' vol. 139, pp. 13243-13248.

International Search Report issued in PCT/JP2019/050261; mailed Mar. 24, 2020; 9 pages.

H. Yamamoto et al.; "Polymer-Structure Dependence of Acid Generation in Chemically Amplified Extreme Ultraviolet Resits"; Jpn. J.Appl.Phys.46,L142; 2007.

International Search Report issued in PCT/JP2021/003658; mailed Apr. 27, 2021; 7 pages.

H. Yamamoto et al.; "Study on acid generation from polymer"; J.Vac.Sci.Technol.b; 23,2728; 2005.

CID 86081112, National Center for Biotechnology Information, PubChem Compound Summary for CID 86081112, 2025, 6 pages.

Shinji Okazaki et al., "New Trends of Photoresists", CMC Publishing Co., Ltd., Sep. 2009, p. 211-259.

(56) References Cited

OTHER PUBLICATIONS

Ahmed Munir et al., The Direct Bradsher Reaction. Part I. Synthesis of Thiophen Analogues of Linear Polycyclic Hydrocarbons, Journal of the Chemical Society, Perkin Transactions 1,1973, pp. 1099-1103.
Areephong, Jetsuda, et al., "A concise synthesis of functionalized 7-oxa-[5]-helicenes," Tetrahedron Letters, 2004, vol. 45, pp. 3067-3070.
Bentley, K. W., and Robinson, R., "A Synthesis of alpha-Anhydrotrimethylbrazilone," Tetrahedron Letters, 1959, vol. 1, Issue 2, pp. 11-14.
Brecher, Jonathan, Graphical Representation Standards for Chemical Structure Diagrams, Pure Appl. Chem., 2008, pp. 277-410, vol. 80, No. 2, Cambridge, Massachusetts.
Burnett, James C., et al. "Novel small molecule inhibitors of botulinum neurotoxin A metalloprotease activity," Biochemical and Biophysical Research Communications, vol. 310, No. 1, Oct. 2003, pp. 84-93.
Cameron, Donald W., et al., "Synthesis of a natural polychloro dinaphthofuran quinone," Tetrahedron Letters, 1980, vol. 21(14), pp. 1385-1386.
Chatterjea, J.N., "Experiments on the Syntheses of Furano Compounds. Part XII. Further Transformations of isoCoumaranone," Journal of the Indian Chemical Society, 1957, vol. 34, Issue 4, pp. 299-305,.
Clowes, G. A., et al., "Studies of the Scholl reaction: Oxidative Dehydrogenation involving 1-Ethoxynaphthylenen and Related Compounds," J Chem. Soc (C) 2519-2526 (1968).
Dann, von Otto, and Hofmann, Hans, Synthese von ( )-Brasilin, Justus Liebigs Annalen der Chemie, 1963, vol. 667, Issue 1, pp. 116-125.
English Translation of JP H01-283280 A, Nov. 14, 1989.
European Journal of Medicinal Chemistry, published bi-monthly, Ejmcs, 13(4): 381-385 (1978).
Ghodratbeigi Mohsen et al., "Design, modeling and synthesis of molecular tweezers with self-assembly Properties," Journal of Molecular Structure, 2011, vol. 990, No. 1, pp. 140-151.
Hagihara K. et al., "The effect of Ti-addition on plastic deformation and fracture behavior of directionally solidified NliAl/Cr(Mo) eutetic alloys," Intermetallics, 2006, vol. 14, No. 10, pp. 1326-1331.
Hannuksela, Miska M. et al., "Hook for scalable extensions: video parameter set," Joint Collaborative Team on Video Coding (JCT-VC) of ITU-T SG 16 WP 3 and ISO/IEC JTC 1/SC 29/WG 11, May 2012, pp. 1-6.
International Preliminary Report on Patentability issued in International Application No. PCT/JP2012/070304.
International Search Report date of mailing Feb. 25, 2014 for PCT/JP2014/051775 and English translation of the same (4 pages).
International Search Report date of mailing Feb. 9, 2016, for PCT/JP2015/084907 and English translation of the same (7 pages).
International Search Report dated Mar. 25, 2014 for International Application No. PCT/JP2014/052524 with English Translation (8 pages).
International Search Report dated May 13, 2014 for International Application No. PCT/JP2014/052530 with English Translation (8 pages).
International Search Report dated Oct. 23, 2012 issued in International Application No. PCT/JP2012/070304.
International Search Report dated Sep. 11, 2012 for International Application No. PCT/JP2012/070305 with English Translation (5 pages).
International Search Report on Patentability for PCT/JP2016/056333 mailed May 24, 2016; English translation submitted herewith (7 pages).
Jha Amitabh and Beal Jennifer, "Convenient synthesis of 12H-benzo[a]xanthenes from 2-tetralone," Tetrahedron Letters, 2004, vol. 45, No. 49, pp. 8999-9001.
Journal of the Chemical Society, p. 5336-5341 (Nov. 1963).
Luo, Junfei et al., "Salicylic acids as readily available starting materials for the synthesis of meta-substituted biaryls," ChemComm, 2015, vol. 51, pp. 3127-3130.
Machine English Translation of JP 2008-239868 A, Oct. 9, 2008.
Massif, Cedrik, et al. "New insights into the water-solubilisation of fluorophores by post-synthetic 'click' and Sonogashira reactions," Organic & Biomolecular Chemistry, vol. 10, No. 22, Apr. 2012, pp. 4430-4336.
Nakayama, Tomonari, Nomura, Masayoshi, Haga, Kohji, and Ueda, Mitsuru, A New Three-Component Photoresist Based on Calix[4]resorcinarene Derivative, a Cross-Linker, and a Photo-acid Generator, The Chemical Society of Japan, Bulletin of the Chemical Society of Japan, 1998, vol. 71, No. 12, pp. 2979-2984.
Nature, 161:930-931 (1948).
Nishiyama Tomihiro et al., Antioxidant activities of fused heterocyclic compounds, xanthene-2,7-diols with BHT or Catechol skeleton, Polymer Degradation and Stability, 1998, vol. 62, No. 3, pp. 529-534.
Ohishi Takeshi. Tetrahedron Letters 42 (2001) 2493-2496.
Osman A-M, Reactions Between Chloro-p-benzoquinones and Beta-Naphtol, Journal of Organic Chemistry, 1957, vol. 22, pp. 342-344.
Percec, Virgil, et al., Synthesis of Aromatic Polyethers by Scholl Reaction. I. Poly(1,1'-Dinaphthyl Ether Phenyl Sulfone)s and Poly(1,1'-Dinaphthyl Ether Phenyl Ketone)s, Journal of Polymer Science: Part A: Polymer Chemistry, 1988, vol. 26, pp. 783-805.
Percec, Virgil, et al., "Synthesis of Aromatic Polyethers by Scholl Reaction. VI. Aromatic Polyethers by Cation-Radical Polymerization of 4,4'-, 3,3'-, and 2-2'-Bis(1-naphthoxy)biphenyls and of 1,3-Bis(1-naphthoxy)benzene," Macromolecules, 1992, vol. 25(1), pp. 64-74.
Protiva, Miroslav et al., Potential metabolites of tricyclic neuroleptics: 2,8-dihydroxy and 3,8-dihydroxy derivatives of 10-(4-methylpiperazino)-10,11-dihydrodibenzo[b,fJthiepin, Part CXXXIII in the series Neurotropic and Psychotropic Agents, Collection of Czechoslovak Chemical Communications, 1979, vol. 44, No. 10, pp. 2987-2996.
Protiva, Miroslav, et al., "Potential metabolites or tricyclic neuroleptics 3,7-dimethoxy and 7,8-dimethoxy derivatives of 10-{4-methylpiperazino )-10,11-dihydrodibenzo[b,f]thiepin", Collection of Czechoslovak Chemical Communications, 1981, vol. 46, pp. 1808-1817.
Singh Ritesh and Panda Gautam, "Scandium triflate-catalyzed one-pot domino approach towards general and efficient syntheses of unsymmetrical 9-substituted xanthene derivatives," Organic & Biomolecular Chemistry, 2010, vol. 8, No. 5, pp. 1097-1105.
Sirkecioglu Okan et al., A Novel Synthesis of 14-(Hydroxymethylalkyl) Derivatives of Dibenzoxanthenes and 3,3-Dimethyl-4-(2-hydroxy-1-naphthyl)benzo[fJchroman, Journal of Heterocyclic Chemistry, Mar. 1, 1998, vol. 35, No. 2, pp. 457-460.
Sirringhaus Henning et al., Dibenzothienobisbenzothiophene—a novel fused-ring oligomer with high field-effect mobility, Journal of Materials Chemistry, 1999, vol. 9, pp. 2095-2101.
Skandinavisches Archiv fuer Physiologie, 43: 215-243 (1923).
Tian-jun Liu, Ke-shen Zhang, Yong-jun Chen, Dong Wang and Chao-jun Li, "Chiral Conjugated Oligomer Based on 1, 1'-Binol With 3, 3'-Acetylene-Phenylene-Acetylene Spacer", Chinese Journal of Polymer Science, Mar. 8, 2001, vol. 19, No. 5, p. 521-526.
Written Opinion of the International Searching Authority issued in International Application No. PCT/JP2012/070304 (including translation), dated Oct. 23, 2012.
International Search Report on Patentability for PCT/JP2016/056332 mailed May 31, 2016; English translation submitted herewith (11 pages).
Jayakrishnan et al., "Synthesis and Polymerization of Some Iodine-Containing Monomers for Biomedical Applications", Journal of Applied Polymer cience, vol. 44, pp. 743-748 (1992).
Moszner et al., "Synthesis and polymerization of hydrophobic iodine-containing methacrylaes", Die Angewandte Makromolekulare Chemie 224(1995) 115-123 (nr. 3917).
Wang et al., "Radio-opaque Micelles for X-ray Imaging", Aust. J. Chem., 2014, 67, pp. 78-84.
Okamura et al., "Synthesis and properties of radiopaque polymer hydrogels II: copolymers of 2,4,6-triiodophenyl-or-N-(3-carboxy-

(56) References Cited

OTHER PUBLICATIONS 2,4,6,-triiodophenyl)-acrylamide and p-styrene sufonate", Journal of Molecular Structure , vol. 602-603, 2002, 17-28.
Zaharia et al., "Triiodophenyl acrylate-based microbeads find important use in the medical field", Int. J. Nano and Biomaterials, vol. 3, No. 4, 2011.
Artola et al., "Elimination of barium sulphate from acrylic bone cements. Use of two-iodone-containing monomers", Biomaterials vol. 24 (2003) 4071-4080.
Schmidt et al., "Synthesis of 8-Aryl-Substituted Coumarins Based on Ring-Closing Metathesis and Suzuki-Miyaura Coupling: SYnthesis of a Furyl Coumarin Natural Product from Galipea panamensis", The Journal of Organic Chemistry 2012, vol. 77, 2360-2367.
Kruft et al., "Studies on two new radiopaque polymeric biomaterials", Journal of Biomedical Materials Research, vol. 28, 1259-1266 (1994).
Jayakrishnan et al., "Synthesis and Polymerization of Some Iodine-Containing Monomers for Biomedical Applications", Journal of Applied Polymer Science, vol. 44, pp. 743-748 (1992).
Zaharia et al., Triiodophenyl acrylate-based microbeads find important use in the medical field, Int. J. Nano and Biomaterials, vol. 3, No. 4, 2011, pp. 302-315.

* cited by examiner

COMPOUND, (CO)POLYMER, COMPOSITION, METHOD FOR FORMING RESIST PATTERN, METHOD FOR PRODUCING COMPOUND, AND METHOD FOR PRODUCING (CO)POLYMER

CROSS-REFERENCE TO RELATED APPLICATIONS

This application is a U.S. national phase application filed under 35 U.S.C. § 371 of International Application Number PCT/JP2021/018110 filed May 12, 2021, designating the United States, which claims priority from Japanese Application Number 2020-085904, filed May 15, 2020.

FIELD OF THE INVENTION

The present invention relates to a compound, a (co) polymer, a composition, a method for forming a resist pattern, a method for producing a compound, and a method for producing a (co)polymer.

BACKGROUND OF THE INVENTION

In recent years, in the production of semiconductor elements and liquid crystal display elements, semiconductors (patterns) and pixels have been rapidly miniaturized due to the advance in lithography technology. As an approach for pixel miniaturization, the exposure light source has been shifted to have a shorter wavelength, in general. Specifically, ultraviolet rays typified by g-ray and i-ray have been used conventionally, but nowadays, far ultraviolet exposure such as KrF excimer laser (248 nm) and ArF excimer laser (193 nm) is being the center of mass production. Furthermore, the introduction of extreme ultraviolet (EUV) lithography (13.5 nm) is progressing. In addition, electron beam (EB) has also been used for forming a fine pattern.

Examples of general resist materials include polymer based resist materials capable of forming an amorphous film, for example, polymer based resist materials such as polymethyl methacrylate, polyhydroxy styrene with an acid dissociation group, and polyalkyl methacrylate (see, for example, Non Patent Document 1).

Conventionally, a line pattern of about 10 to 100 nm is formed by irradiating a resist thin film made by coating a substrate with a solution of these resist materials with ultraviolet, far ultraviolet, electron beam, extreme ultraviolet, X-ray or the like.

In addition, lithography using electron beam or extreme ultraviolet has a reaction mechanism different from that of normal photolithography. Furthermore, lithography with electron beam or extreme ultraviolet aims at forming fine patterns of several nm to ten-odd nm. Accordingly, there is a demand for a resist material having higher sensitivity for an exposing source when the resist pattern dimension is reduced. In particular, lithography with extreme ultraviolet is required to further increase sensitivity in terms of throughput.

As a resist material that solves the problems as mentioned above, an inorganic resist material having a metallic element such as titanium, tin, hafnium and zirconium has been proposed (see, for example, Patent Document 1).

CITATION LIST

Patent Document

Patent Document 1: Japanese Patent Laid-Open No. 2015-108781

Non Patent Document

Non Patent Document 1: Shinji Okazaki et al., "Development of Lithography Technology in These 40 Years", S&T Publishing Inc., Dec. 9, 2016

SUMMARY OF INVENTION

However, since the compounds and (co)polymers used in conventional resist materials have low stability, there is a problem in that the stability and productivity of the compounds and (co)polymers are poor.

In addition, conventionally developed resist materials have problems such as many film defects, insufficient sensitivity, insufficient etching resistance, or poor resist pattern. In particular, for the reason that resolution and sensitivity are in a trade-off relationship, it is difficult to achieve both high resolution and high sensitivity.

Furthermore, although a (co)polymer having a hydroxy group is useful as a resist material, there is a problem in that the productivity of the (co)polymer is low because the stability of the raw material compound and the (co)polymer is low.

In view of the above circumstances, an object of the present invention is to provide a compound suitable for a resist material and having high stability, and capable of forming a film having high sensitivity and high resolution, a method for producing the compound, a (co)polymer, a composition, and a method for forming a resist pattern using the composition. Another object of the present invention is to provide a method for producing a (co)polymer having a hydroxy group useful for a resist material with high productivity.

As a result of intensive studies to solve the above problems, the present inventors have found that a compound and a (co)polymer having a specific structure and a composition containing the compound and the (co)polymer have high stability, are capable of forming a film having high sensitivity and high resolution, and are suitable as a resist material, thereby completing the present invention.

The present inventors have also found that since a compound and a (co)polymer having a specific structure have high stability, a (co)polymer having a hydroxy group useful for a resist material can be efficiently produced by using the (co)polymer, thereby completing the present invention.

More specifically, the present invention is as follows.

[1]

An iodine-containing (meth)acrylate compound represented by formula (1):

(1)

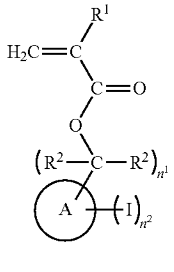

wherein $R^1$ represents a hydrogen atom, a methyl group, or halogen;

each $R^2$ independently represents a hydrogen atom, a linear organic group having 1 to 20 carbon atoms, a branched organic group having 3 to 20 carbon atoms, or a cyclic organic group having 3 to 20 carbon atoms;

A represents an organic group having 1 to 30 carbon atoms;

A comprises at least one acyl group;

$n^1$ represents 0 or 1; and $n^2$ represents an integer of 1 to 20.

[1-1]

The iodine-containing (meth)acrylate compound according to [1], wherein $n^1$ is 0, and A is an alicyclic ring having 5 to 30 carbon atoms optionally having a substituent.

[1-2]

The iodine-containing (meth)acrylate compound according to [1-1], wherein the alicyclic ring having 5 to 30 carbon atoms optionally having a substituent is adamantane optionally having a substituent.

[2]

The iodine-containing (meth)acrylate compound according to [1], wherein the formula (1) is formula (2)

(2)

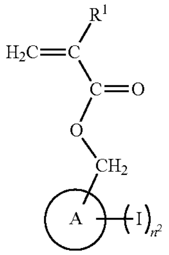

wherein $R^1$, A, and $n^2$ are the same as described above.

[3]

The iodine-containing (meth)acrylate compound according to [2], wherein the formula (2) is formula (3):

(3)

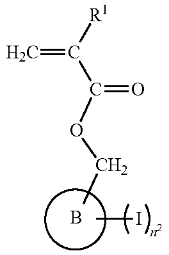

wherein

B represents an organic group containing an aromatic group and having 5 to 30 carbon atoms, B comprises at least one acyl group, and $R^1$ and $n^2$ are as described above.

[3-1]

The iodine-containing (meth)acrylate compound according to [3], wherein B is an aromatic group having 5 to 30 carbon atoms optionally having a substituent.

[3-2]

The iodine-containing (meth)acrylate compound according to [3-1], wherein the aromatic group having 5 to 30 carbon atoms optionally having a substituent is benzene optionally having a substituent.

[4]

The iodine-containing (meth)acrylate compound according to [2], wherein the formula (2) is formula (3'):

(3')

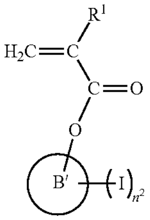

wherein B' represents an organic group containing an alicyclic ring and having 5 to 30 carbon atoms, B' comprises at least one acyl group, and $R^1$ and $n^2$ are as described above.

[4-1]

The iodine-containing (meth)acrylate compound according to [4], wherein B' is an alicyclic ring having 5 to 30 carbon atoms optionally having a substituent.

[4-2]

The iodine-containing (meth)acrylate compound according to [4-1], wherein the alicyclic ring having 5 to 30 carbon atoms optionally having a substituent is adamantane optionally having a substituent.

[5]

The iodine-containing (meth)acrylate compound according to any one of [1] to [4-2], wherein $n^2$ represents an integer of 2 to 20.

[6]

An iodine-containing (meth)acrylate (co)polymer comprising a constituent unit represented by formula (4)

(4)

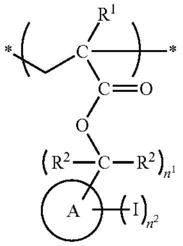

wherein $R^1$ represents a hydrogen atom, a methyl group, or halogen;

each $R^2$ independently represents a hydrogen atom, a linear organic group having 1 to 20 carbon atoms, a branched organic group having 3 to 20 carbon atoms, or a cyclic organic group having 3 to 20 carbon atoms;

A represents an organic group having 1 to 30 carbon atoms;

A comprises at least one acyl group;

$n^1$ represents 0 or 1;

$n^2$ represents an integer of 1 to 20; and the symbol * represents a bonding site to an adjacent constituent unit.

[6-1]

The iodine-containing (meth)acrylate (co)polymer according to [6], wherein $n^1$ is 0, and A is an alicyclic ring having 5 to 30 carbon atoms optionally having a substituent.

[6-2]

The iodine-containing (meth)acrylate (co)polymer according to [6-1], wherein the alicyclic ring having 5 to 30 carbon atoms optionally having a substituent is adamantane optionally having a substituent.

[7]

The iodine-containing (meth)acrylate (co)polymer according to [6], wherein the formula (4) is formula (5)

(5)

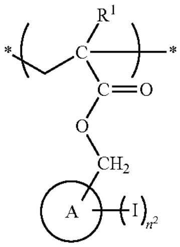

wherein $R^1$, $n^2$, A, and the symbol * are the same as described above.

[8]

The iodine-containing (meth)acrylate (co)polymer according to [7], wherein the formula (5) is formula (6)

(6)

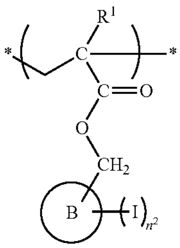

wherein B represents an organic group containing an aromatic group and having 5 to 30 carbon atoms, B comprises at least one acyl group, and $R^1$, $n^2$, and the symbol * are as described above.

[8-1]

The iodine-containing (meth)acrylate (co)polymer according to [8], wherein B is an aromatic group having 5 to 30 carbon atoms optionally having a substituent.

[8-2]

The iodine-containing (meth)acrylate (co)polymer according to [8-1], wherein the aromatic group having 5 to 30 carbon atoms optionally having a substituent is benzene optionally having a substituent.

[9]

The iodine-containing (meth)acrylate (co)polymer according to [7], wherein the formula (5) is formula (6'):

(6')

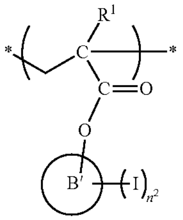

wherein B' represents an organic group containing an alicyclic ring and having 5 to 30 carbon atoms, B' comprises at least one acyl group, and $R^1$, $n^2$, and the symbol * are as described above.

[9-1]

The iodine-containing (meth)acrylate (co)polymer according to [9], wherein B' is an alicyclic ring having 5 to 30 carbon atoms optionally having a substituent.

[9-2]

The iodine-containing (meth)acrylate (co)polymer according to [9-1], wherein the alicyclic ring having 5 to 30 carbon atoms optionally having a substituent is adamantane optionally having a substituent.

[10]

The iodine-containing (meth)acrylate (co)polymer according to any one of [6] to [9-2], wherein $n^2$ represents an integer of 2 to 20.

[11]

A composition comprising the iodine-containing (meth) acrylate compound according to any one of [1] to [5] and/or the iodine-containing (meth)acrylate (co)polymer according to any one of [6] to [10].

[12]

The composition according to [11], further comprising a solvent.

[13]

The composition according to [11] or [12], further comprising an acid generating agent.

[14]

The composition according to any one of [11] to [13], further comprising an acid diffusion controlling agent.

[15]

A method for forming a resist pattern, comprising the steps of:

forming a film using the composition according to any one of [11] to [14];

exposing the formed film; and removing an exposed portion of the exposed film using a developer to form a pattern.

[16]

A method for producing the iodine-containing (meth) acrylate compound according to any one of [1] to [5], comprising the steps of:

reacting an iodine-containing hydroxy compound represented by formula (a) with a (meth)acrylic acid compound represented by formula (b);

reacting the obtained reaction product with an acylating agent:

(a)

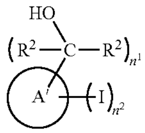

wherein A' represents an organic group having 1 to 30 carbon atoms, A' comprises at least one hydroxy group, and $R^2$, $n^1$, and $n^2$ are as described above, and (b)

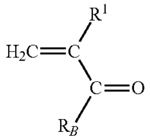

wherein $R^1$ is the same as described above, and $R_B$ is a hydroxy group, halogen, a (meth)acryloyloxy group, or an alkoxy group.

[16-1]

The method for producing the iodine-containing (meth) acrylate compound according to [16], wherein $n^1$ is 0, A' is an alicyclic ring having 5 to 30 carbon atoms optionally having a substituent, and A' comprises at least one hydroxy group.

[16-2]

The iodine-containing (meth)acrylate compound according to [16-1], wherein the alicyclic ring having 5 to 30 carbon atoms optionally having a substituent is adamantane optionally having a substituent.

[17]

The method for producing the iodine-containing (meth) acrylate compound according to [16], wherein the formula (a) is formula (a1):

(a1)

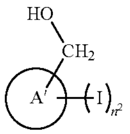

wherein A' and $n^2$ are the same as described above.

[18]

The method for producing the iodine-containing (meth) acrylate compound according to [16], wherein the formula (a) is formula (a2):

(a2)

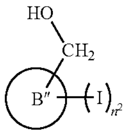

wherein B" represents an organic group containing an aromatic group and having 5 to 30 carbon atoms, B" comprises at least one hydroxy group, and $n^2$ is as described above.

[18-1]

The method for producing the iodine-containing (meth) acrylate compound according to [18], wherein B" is an aromatic group having 5 to 30 carbon atoms optionally having a substituent, and B" comprises at least one hydroxy group.

[18-2]

The method for producing the iodine-containing (meth) acrylate compound according to [18-1], wherein the aromatic group having 5 to 30 carbon atoms optionally having a substituent is benzene optionally having a substituent.

[19]

The method for producing the iodine-containing (meth) acrylate compound according to [16], wherein the formula (a) is formula (a3):

(a3)

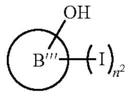

wherein B'" represents an organic group containing an alicyclic ring and having 5 to 30 carbon atoms, B comprises at least one hydroxy group, and $n^2$ is as described above.

[19-1]

The method for producing the iodine-containing (meth) acrylate compound according to [19], wherein B'" is an alicyclic ring having 5 to 30 carbon atoms optionally having a substituent, and B'" comprises at least one hydroxy group.

[19-2]

The method for producing the iodine-containing (meth) acrylate compound according to [19-1], wherein the alicyclic ring having 5 to 30 carbon atoms optionally having a substituent is adamantane optionally having a substituent.

[20]

The method for producing the iodine-containing (meth) acrylate compound according to any one of [16] to [19], wherein $n^2$ represents an integer of 2 to 20.

[21]

A method for producing a (co)polymer having a hydroxy group represented by formula (Y), comprising the step of hydrolyzing an acyl group in the iodine-containing (meth) acrylate (co)polymer according to any one of [6] to [9]:

(Y)

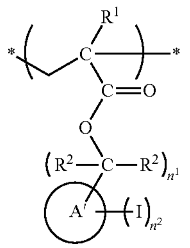

wherein $R^1$ represents a hydrogen atom, a methyl group, or halogen;

each $R^2$ independently represents a hydrogen atom, a linear organic group having 1 to 20 carbon atoms, a branched organic group having 3 to 20 carbon atoms, or a cyclic organic group having 3 to 20 carbon atoms;

A' represents an organic group having 1 to 30 carbon atoms;

A' comprises at least one hydroxy group;

$n^1$ represents 0 or 1;

$n^2$ represents an integer of 1 to 20; and the symbol * represents a bonding site to an adjacent constituent unit.

According to the present invention, it is possible to provide a compound suitable for a resist material and having high stability, and capable of forming a film having high sensitivity and high resolution, a method for producing the compound, a (co)polymer, a composition, and a method for forming a resist pattern using the composition. It is also possible to provide a method for efficiently producing a (co)polymer having a hydroxy group useful for a resist material by using the compound and the (co)polymer.

DESCRIPTION OF EMBODIMENT

Hereinafter, an embodiment of the present invention will be described (hereinafter, may be referred to as the "present embodiment"). The present embodiment is given in order to illustrate the present invention. The present invention is not limited to only the present embodiment.

In the present specification, the (meth)acrylate means acrylate and methacrylate. Other terms having the expression (meth) shall be construed in the same manner as (meth)acrylate.

In the present specification, the (co)polymer means a homopolymer and a copolymer.

[Iodine-Containing (Meth)Acrylate Compound]

The iodine-containing (meth)acrylate compound (also simply referred to as "compound") of the present embodiment is represented by the following formula (1). Since the compound has high stability, the compound can be efficiently produced. The compound can achieve high sensitivity in a lithography process, and can form a film having high resolution. Furthermore, a (co)polymer containing the compound as a constituent unit also has high stability, and an iodine-containing (meth)acrylate (co)polymer (also simply referred to as "(co)polymer") can be efficiently produced.

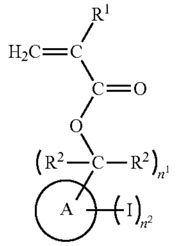

(1)

In the formula (1), $R^1$ represents a hydrogen atom, a methyl group, or halogen; each $R^2$ independently represents a hydrogen atom, a linear organic group having 1 to 20 carbon atoms, a branched organic group having 3 to 20 carbon atoms, or a cyclic organic group having 3 to 20 carbon atoms; A represents an organic group having 1 to 30 carbon atoms; A contains at least one acyl group; $n^1$ represents 0 or 1; and $n^2$ represents an integer of 1 to 20.

As $R^1$, a hydrogen atom, a methyl group, or halogen can be used. As the halogen, publicly known atoms can be used, and fluorine (F), chlorine (Cl), bromine (Br), iodine (I), or the like can be appropriately used. $R^1$ is preferably a methyl group or halogen from the viewpoint of exposure sensitivity and material stability when the compound of the present embodiment is used as a constituent unit of resin for resists, and more preferably a methyl group in terms of more excellent stability. Further, in consideration of more excellent exposure sensitivity, $R^1$ is more preferably halogen, and still more preferably iodine (I).

$R^2$ may be a combination of two or more selected from the group consisting of a linear organic group having 1 to 20 carbon atoms, a branched organic group having 3 to 20 carbon atoms, and a cyclic organic group having 3 to 20 carbon atoms.

$R^2$ is preferably a hydrogen atom for the purpose of suppressing an increase in Tg (glass transition temperature) of the resin and improving the effect of introducing the iodine element. On the other hand, for the purpose of controlling solubility in the developer, it is preferable to use an organic group having 1 or more carbon atoms in order to improve the acid decomposability. It is more preferable to use a hydrogen atom for the purpose of suppressing acid decomposability, especially ensuring solubility in an alkali developer and suppressing residue.

$R^2$ may have a substituent. Examples of $R^2$ include, for example, an alkyl group having 1 to 20, preferably 1 to 10, and more preferably 1 to 6 carbon atoms, optionally having a substituent; an alkenyl group having 2 to 20, preferably 2 to 10, and more preferably 2 to 6 carbon atoms, optionally having a substituent; an alkynyl group having 2 to 20, preferably 2 to 10, and more preferably 2 to 6 carbon atoms, optionally having a substituent; a cycloalkyl group having 3 to 20, preferably 3 to 10, and more preferably 3 to 6 carbon atoms, optionally having a substituent; a cycloalkenyl group having 3 to 20, preferably 3 to 10, and more preferably 3 to 6 carbon atoms, optionally having a substituent; a cycloalkynyl group having 3 to 20, preferably 3 to 10, and more preferably 3 to 6 carbon atoms, optionally having a substituent; an aryl group having 5 to 20, preferably 5 to 10, and more preferably 5 to 6 carbon atoms, optionally having a substituent; and combinations thereof.

Specific examples of $R^2$ include a methyl group, an ethyl group, a propyl group, a butyl group, a pentyl group, a hexyl group, a heptyl group, an octyl group, a nonyl group, a decyl group, an icosyl group, a cyclopropyl group, a cyclobutyl group, a cyclopentyl group, a cyclohexyl group, a cycloheptyl group, a cyclooctyl group, a cyclononyl group, a cyclodecyl group, a cycloicosyl group, an adamantyl group, an ethylene group, a propylene group, a butylene group, a phenyl group, a naphthyl group, an anthracene group, a phenanthrene group, a tetracene group, a chrysene group, a triphenylene group, a pyrene group, a benzopyrene group, an azulene group, and a fluorene group, optionally having a substituent. These groups may each contain an ether bond, a ketone bond or an ester bond.

In the present embodiment, the groups listed above include isomers. Examples of such isomers include n-propyl group and isopropyl group in the case of propyl group, and n-butyl group, sec-butyl group, isobutyl group, and tert-butyl group in the case of butyl group.

Examples of the substituent for $R^2$ include, but are not particularly limited to, halogen, a hydroxy group, a cyano group, a nitro group, an amino group, a thiol group, a heterocyclic group, a linear aliphatic hydrocarbon group, a branched aliphatic hydrocarbon group, a cyclic aliphatic hydrocarbon group, an aryl group, an aralkyl group, an alkoxy group, an alkenyl group, an acyl group, an alkoxycarbonyl group, an alkyloyloxy group, an aryloyloxy group, and an alkylsilyl group, and various crosslinkable groups and acid dissociation groups.

The "crosslinkable group" refers to a group capable of crosslinking by acid, alkali, light or heat in the presence of a catalyst or without a catalyst. Examples of the crosslinkable group include, but not particularly limited to, a group having an allyl group, a group having a (meth)acryloyl group, a group having an epoxy (meth)acryloyl group, a group having a urethane (meth)acryloyl group, a group having a hydroxy group, a group having a glycidyl group, a group having a vinyl phenylmethyl group, a group having a styrene group, a group having an alkynyl group, a group having a carbon-carbon double bond, a group having a carbon-carbon triple bond, and a group containing these groups.

The "acid dissociation group" is a group that is cleaved in the presence of an acid to generate an alkali soluble group (for example, a phenolic hydroxy group, a carboxyl group, a sulfonic acid group, or a hexafluoroisopropanol group) or the like. The acid dissociation group is not particularly limited, but can be appropriately selected for use from among, for example, those proposed in hydroxystyrene resins, (meth)acrylic resins, and the like for use in chemically amplified resist compositions for KrF or ArF. Specific examples of the acid dissociation group include, for example, those described in International Publication No. WO 2016/158168.

A may have a substituent. Examples of the compound serving as the skeleton of A include, for example, an alkane group having 1 to 30, preferably 1 to 20, more preferably 1 to 10, and still more preferably 1 to 6 carbon atoms, optionally having a substituent; an alkene group having 2 to 30, preferably 2 to 20, more preferably 2 to 10, and still more preferably 2 to 6 carbon atoms, optionally having a substituent; an alkyne group having 2 to 30, preferably 2 to 20, more preferably 2 to 10, and still more preferably 2 to 6 carbon atoms, optionally having a substituent; a cycloalkane group having 3 to 30, preferably 3 to 20, more preferably 3 to 10, and still more preferably 3 to 6 carbon atoms, optionally having a substituent; a cycloalkene group having 3 to 30, preferably 3 to 20, more preferably 3 to 10, and still more preferably 3 to 6 carbon atoms, optionally having a substituent; a cycloalkyne group having 3 to 30, preferably 3 to 20, more preferably 3 to 10, and still more preferably 3 to 6 carbon atoms, optionally having a substituent; an arene group having 5 to 30, preferably 5 to 20, more preferably 5 to 10, and still more preferably 5 to 6 carbon atoms, optionally having a substituent; and combinations thereof.

Specific examples of the compound serving as the skeleton of A include methane, ethane, propane, butane, pentane, hexane, heptane, octane, nonane, decane, icosane, triacontane, cyclopropane, cyclobutane, cyclopentane, cyclohexane, cycloheptane, cyclooctane, cyclononane, cyclodecane, cycloicosane, cyclotriacontane, adamantane, ethylene, propylene, butene, pentene, hexene, heptene, octene, nonene, decene, icosene, triacontene, benzene, phenol, naphthalene, anthracene, phenanthrene, tetracene, chrysene, triphenylene, pyrene, pentacene, benzopyrene, coronene, azulene, and fluorene, optionally having a substituent, and combinations thereof. These may each contain an ether bond, a ketone bond or an ester bond.

Examples of the substituent for the compound serving as the skeleton of A include, but are not particularly limited to, halogen (fluorine, chlorine, bromine), a hydroxy group, a cyano group, a nitro group, an amino group, a thiol group, a heterocyclic group, a linear aliphatic hydrocarbon group, a branched aliphatic hydrocarbon group, a cyclic aliphatic hydrocarbon group, an aryl group, an aralkyl group, an alkoxy group, an alkenyl group, an acyl group, an alkoxycarbonyl group, an alkyloyloxy group, an aryloyloxy group, and an alkylsilyl group, and various crosslinkable groups and acid dissociation groups. From the viewpoint of enhancing stability and productivity of the iodine-containing (meth) acrylate compound, it is preferable that the substituent for the compound serving as the skeleton of A does not contain a hydroxy group.

The "crosslinkable group" and the "acid dissociation group" are not particularly limited, and for example, those described for $R^2$ can be used.

In view of achieving all of film defect reduction, compound stability, sensitivity, and etching resistance, A is preferably an alicyclic ring having 5 to 30 carbon atoms optionally having a substituent, in which $n^1$ is 0, more preferably alicyclic hydrocarbon having 5 to 30 carbon atoms optionally having a substituent, in which $n^1$ is 0, and still more preferably adamantane optionally having a substituent, in which $n^1$ is 0. Examples of the alicyclic ring include cyclopropane, cyclobutane, cyclopentane, cyclohexane, cycloheptane, cyclooctane, cyclononane, cyclodecane, cycloicosane, cyclotriacontane, and adamantane, which may contain an ether bond, a ketone bond, and an ester bond.

Examples of the alicyclic hydrocarbon include cyclopropane, cyclobutane, cyclopentane, cyclohexane, cycloheptane, cyclooctane, cyclononane, cyclodecane, cycloicosane, cyclotriacontane, and adamantane.

A contains at least one acyl group. The acyl group is preferably contained as the substituent for the compound serving as the skeleton of A. The substituent may contain an ether bond, a ketone bond, or an ester bond, but preferably contains an ether bond. Specific examples of the acyl group include a methanoyl group (formyl group), an ethanoyl group (acetyl group), a propanoyl group, a butanoyl group, a pentanoyl group, a hexanoyl group, an octanoyl group, a decanoyl group, and a benzoyl group. An ethanoyl group (acetyl group) and a benzoyl group are preferable, and an ethanoyl group (acetyl group) is more preferable.

It is preferable that A contains at least one acyl group from the viewpoint of enhancing the stability of the compound and the (co)polymer. It is also preferable from the viewpoint of enhancing the productivity of the compound and the (co)polymer. When an acyl group is contained as a substituent in the compound serving as the skeleton of A, the stability of the compound and the (co)polymer is further enhanced, and the resin into which the compound and the (co)polymer are introduced is satisfactorily dissolved in an organic solvent and is more excellent in storage stability, and thus the number of acyl groups in the compound serving as the skeleton of A is preferably 1 to 10, more preferably 1 to 5, still more preferably 1 to 3, and further preferably 1.

$n^1$ represents 0 or 1, and is preferably 1.

In view of achieving all of film defect reduction, sensitivity, and etching resistance, A is preferably an aromatic group having 5 to 30 carbon atoms optionally having a substituent, in which $n^1$ is 1, and more preferably benzene optionally having a substituent, in which $n^1$ is 1. Specific examples of the aromatic group include, for example, benzene, phenol, naphthalene, anthracene, phenanthrene, tetracene, chrysene, triphenylene, pyrene, pentacene, benzopyrene, and coronene. These may each contain an ether bond, a ketone bond or an ester bond.

A contains at least one acyl group. The acyl group is as described above. When $n^1$ is 1, among the acyl groups, an ethanoyl group (acetyl group) and a benzoyl group are preferable, and an ethanoyl group (acetyl group) is more preferable.

It is preferable that A contains at least one acyl group from the viewpoint of enhancing the stability of the compound and the (co)polymer. It is also preferable from the viewpoint of enhancing the productivity of the compound and the (co)polymer. When an acyl group is contained as an aromatic substituent, the stability of the compound and the (co)polymer is further enhanced, and the resin into which the compound and the (co)polymer are introduced is satisfactorily dissolved in an organic solvent and is more excellent in storage stability, and thus the number of acyl groups in the aromatic substituent is preferably 1 to 8, more preferably 1 to 5, still more preferably 1 to 3, and further preferably 1.

In view of achieving both sensitivity and etching resistance, $n^2$ is an integer of 1 to 20, preferably an integer of 1 to 20, more preferably an integer of 1 to 10, and still more preferably an integer of 2 to 5.

The compound represented by the above formula (1) is preferably a compound represented by the formula (2) from the viewpoint of reactivity.

(2)

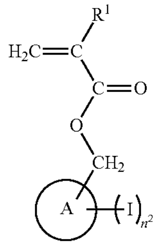

In the formula (2), $R^1$, A, and $n^2$ are as defined in the above formula (1).

The compound represented by the above formula (1) is more preferably a compound represented by the formula (3) from the viewpoint of etching resistance.

(3)

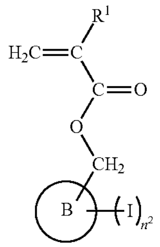

In the formula (3), B represents an organic group containing an aromatic group and having 5 to 30 carbon atoms, and B contains at least one acyl group. $R^1$ and $n^2$ are as defined in the above formula (1).

B may have a substituent. Examples of the compound serving as the skeleton of B include, for example, an arene having 5 to 30 carbon atoms, preferably 5 to 20 carbon atoms, more preferably 5 to 10 carbon atoms, and still more preferably 5 to 6 carbon atoms, which may have a substituent.

Specific examples of the compound serving as the skeleton of B include benzene, phenol, naphthalene, anthracene, phenanthrene, tetracene, chrysene, triphenylene, pyrene, pentacene, benzopyrene, coronene, azulene, fluorene, and combinations thereof, optionally having a substituent. These may each contain an ether bond, a ketone bond or an ester bond.

Examples of the substituent for the compound serving as the skeleton of B include, but are not particularly limited to, halogen (fluorine, chlorine, bromine), a hydroxy group, a cyano group, a nitro group, an amino group, a thiol group, a heterocyclic group, a linear aliphatic hydrocarbon group, a branched aliphatic hydrocarbon group, a cyclic aliphatic hydrocarbon group, an aryl group, an aralkyl group, an alkoxy group, an alkenyl group, an acyl group, an alkoxycarbonyl group, an alkyloyloxy group, an aryloyloxy group, and an alkylsilyl group, and various crosslinkable groups and acid dissociation groups. From the viewpoint of enhancing stability and productivity of the iodine-containing (meth) acrylate compound, it is preferable that the substituent for the compound serving as the skeleton of B does not contain a hydroxy group.

The "crosslinkable group" and the "acid dissociation group" are not particularly limited, and for example, those described for $R^2$ can be used. The acid dissociation group bonded to the aromatic group of B is preferably a group that is cleaved in the presence of an acid to generate a hydroxy group.

In view of achieving all of film defect reduction, sensitivity, and etching resistance, B is preferably an aromatic group having 5 to 30 carbon atoms optionally having a substituent, and more preferably benzene optionally having a substituent. Specific examples of the aromatic group include, for example, benzene, phenol, naphthalene, anthracene, phenanthrene, tetracene, chrysene, triphenylene, pyrene, pentacene, benzopyrene, and coronene.

B contains at least one acyl group. The acyl group is as described above. Among them, an ethanoyl group (acetyl group) and a benzoyl group are preferable, and an ethanoyl group (acetyl group) is more preferable.

It is preferable that B contains at least one acyl group from the viewpoint of enhancing the stability of the compound and the (co)polymer. It is also preferable from the viewpoint of enhancing the productivity of the compound and the (co)polymer. When an acyl group is contained as a substituent in the compound serving as the skeleton of B, the stability of the compound and the (co)polymer is further enhanced, and the resin into which the compound and the (co)polymer are introduced is satisfactorily dissolved in an organic solvent and is more excellent in storage stability, and thus the number of acyl groups in the compound serving as the skeleton of B is preferably 1 to 8, more preferably 1 to 5, still more preferably 1 to 3, and further preferably 1.

The compound represented by the above formula (1) is more preferably a compound represented by the formula (3') from the viewpoint of etching resistance.

(3')

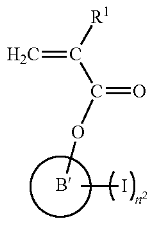

In the formula (3'), B' represents an organic group containing an alicyclic ring and having 5 to 30 carbon atoms, and B' contains at least one acyl group. $R^1$ and $n^2$ are as defined in the above formula (1).

B' may have a substituent. Examples of the compound serving as the skeleton of B' include, for example, a cycloalkane having 5 to 30, preferably 5 to 20, more preferably 5 to 10, and still more preferably 5 to 6 carbon atoms, optionally having a substituent; a cycloalkene having 5 to 30, preferably 5 to 20, more preferably 5 to 10, and still more preferably 5 to 6 carbon atoms, optionally having a substituent; and a cycloalkyne having 5 to 30, preferably 5 to 20, more preferably 5 to 10, and still more preferably 5 to 6 carbon atoms, optionally having a substituent; and combinations thereof.

Specific examples of the compound serving as the skeleton of B' include cyclopentane, cyclohexane, cycloheptane, cyclooctane, cyclononane, cyclodecane, cycloicosane, cyclotriacontane, and adamantane, optionally having a substituent, and combinations thereof. These may each contain an ether bond, a ketone bond or an ester bond.

Examples of the substituent for the compound serving as the skeleton of B' include, but are not particularly limited to, halogen (fluorine, chlorine, bromine), a hydroxy group, a cyano group, a nitro group, an amino group, a thiol group, a heterocyclic group, a linear aliphatic hydrocarbon group, a branched aliphatic hydrocarbon group, a cyclic aliphatic hydrocarbon group, an aryl group, an aralkyl group, an alkoxy group, an alkenyl group, an acyl group, an alkoxycarbonyl group, an alkyloyloxy group, an aryloyloxy group, and an alkylsilyl group, and various crosslinkable groups and acid dissociation groups. From the viewpoint of enhancing stability and productivity of the iodine-containing (meth) acrylate compound, it is preferable that the substituent for the compound serving as the skeleton of B' does not contain a hydroxy group.

The "crosslinkable group" and the "acid dissociation group" are not particularly limited, and for example, those described for $R^2$ can be used.

In view of achieving all of film defect reduction, compound stability, sensitivity, and etching resistance, B' is preferably an alicyclic ring having 5 to 30 carbon atoms optionally having a substituent, more preferably alicyclic hydrocarbon having 5 to 30 carbon atoms optionally having a substituent, and still more preferably adamantane optionally having a substituent. The alicyclic ring and alicyclic hydrocarbon are as described above.

B' contains at least one acyl group. The acyl group is as described above. Among them, an ethanoyl group (acetyl group) and a benzoyl group are preferable, and an ethanoyl group (acetyl group) is more preferable.

It is preferable that B' contains at least one acyl group from the viewpoint of enhancing the stability of the compound and the (co)polymer. It is also preferable from the viewpoint of enhancing the productivity of the compound and the (co)polymer. When an acyl group is contained as a substituent in the compound serving as the skeleton of B', the stability of the compound and the (co)polymer is further enhanced, and the resin into which the compound and the (co)polymer are introduced is satisfactorily dissolved in an organic solvent and is more excellent in storage stability, and thus the number of acyl groups in the compound serving as the skeleton of B' is preferably 1 to 10, more preferably 1 to 5, still more preferably 1 to 3, and further preferably 1.

Specific examples of the iodine-containing (meth)acrylate compound of the present embodiment are shown below, but are not limited thereto. In the following examples, $R^1$ represents a hydrogen atom, a methyl group, or halogen. R' represents an acyl group, preferably an acetyl group. In the following examples, I represents an iodide atom, and $I_{1-9}$ means that 1 to 9 I are bonded to the carbons of adamantane.

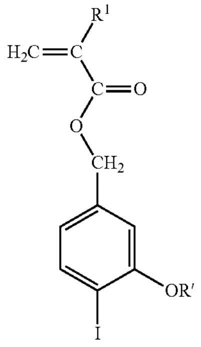
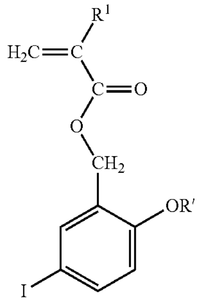
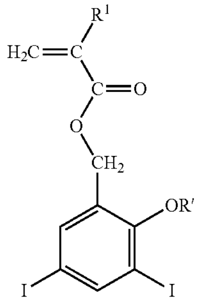
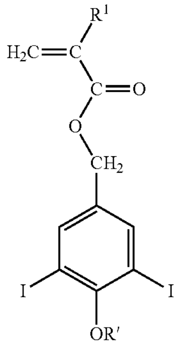
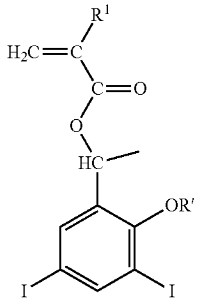
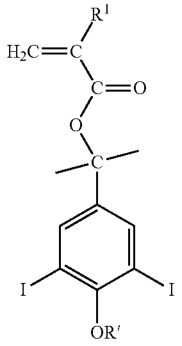
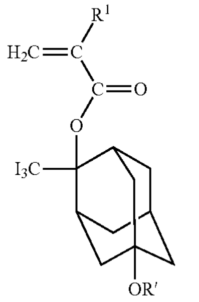
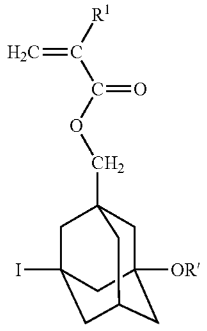
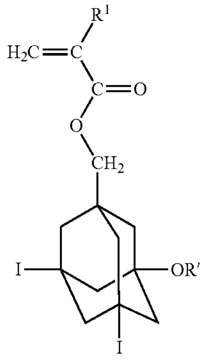
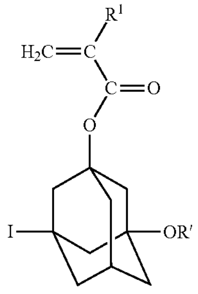

-continued

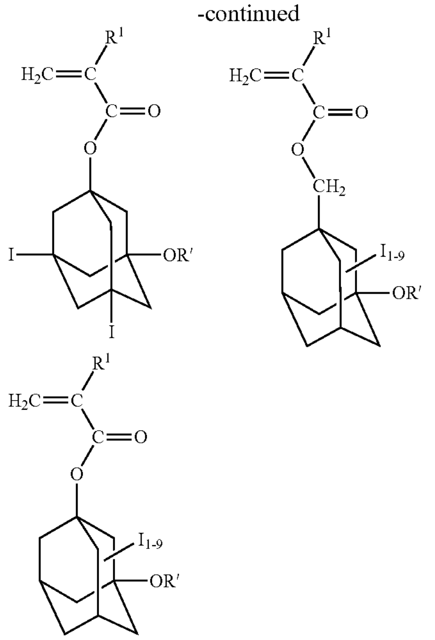

As for structural formulas described in the present specification, for example, when a line indicating a bond to C is in contact with a ring A and a ring B as described below, C is meant to be bonded to either the ring A or the ring B.

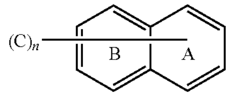

[Method for Producing Iodine-Containing (Meth)Acrylate Compound]

The iodine-containing (meth)acrylate compound of the present embodiment can be produced by a publicly known method. Examples of such a method include, but are not particularly limited to, a method which includes the steps of reacting an iodine-containing hydroxy compound represented by the formula (a) with a (meth)acrylic acid compound represented by the formula (b) to obtain an iodine-containing hydroxy (meth)acrylic acid compound, and then reacting a hydroxy group derived from the iodine-containing hydroxy compound represented by the formula (a) in the compound with an acylating agent to obtain the iodine-containing (meth)acrylate compound; and a method which includes the steps of reacting a hydroxy group in an iodine-containing hydroxy compound represented by the formula (a) with an acylating agent to obtain a reaction product, and then reacting the reaction product with a (meth)acrylic acid compound represented by the formula (b) to obtain the iodine-containing (meth)acrylate compound.

(a)

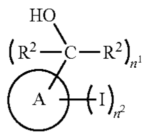

In the formula (a), A' represents an organic group having 1 to 30 carbon atoms, A' has at least one hydroxy group, and $R^2$, $n^1$, and $n^2$ are as defined in the above formula (1). A' is the same as A in the above formula (1) except that A' contains at least one hydroxy group instead of the acyl group in A in the above formula (1). When a hydroxy group is contained as a substituent in the compound serving as the skeleton of A', the stability of the compound and the (co)polymer is further enhanced, and the resin into which the compound and the (co)polymer are introduced is satisfactorily dissolved in an organic solvent and is more excellent in storage stability, and thus the number of hydroxy groups in the compound serving as the skeleton of A' is preferably 1 to 10, more preferably 1 to 5, still more preferably 1 to 3, and further preferably 1. The compound serving as the skeleton of A' is the same as the compound serving as the skeleton of A described above.

$n^2$ is an integer of 1 to 20. In view of achieving both high sensitivity and high resolution, $n^2$ is preferably an integer of 1 to 20, more preferably an integer of 1 to 10, and still more preferably an integer of 2 to 5.

(b)

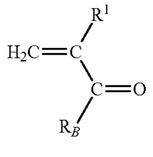

In the formula (b), $R^1$ is as defined in the above formula (1). $R_B$ is a hydroxy group, halogen, a (meth)acryloyloxy group, or an alkoxy group. $R_B$ is preferably halogen or a (meth)acryloyloxy group. The halogen is preferably chlorine. Examples of the alkoxy group include a methoxy group, an ethoxy group, a propoxy group, an isopropoxy group, a n-butoxy group, an isobutoxy group, a tert-butoxy group, a n-hexanoxy group, a 2-methylpropoxy group, a methoxy group, and a phenoxy group.

In view of achieving all of film defect reduction, compound stability, sensitivity, and etching resistance, in the formula (a), it is preferable that A' is an alicyclic ring having 5 to 30 carbon atoms optionally having a substituent, in which $n^1$ is 0, and A' has at least one hydroxy group; it is more preferable that alicyclic hydrocarbon having 5 to 30 carbon atoms optionally having a substituent, in which $n^1$ is 0, and A' has at least one hydroxy group; and it is still more preferable that adamantane optionally having a substituent, in which $n^1$ is 0, and A' has at least one hydroxy group. The alicyclic ring and alicyclic hydrocarbon are as described above.

In view of achieving all of film defect reduction, sensitivity, and etching resistance, it is preferable that A' is an aromatic group having 5 to 30 carbon atoms optionally having a substituent, in which $n^1$ is 1, and A' has at least one hydroxy group; and it is more preferable that A' is benzene optionally having a substituent, in which $n^1$ is 1, and A' has at least one hydroxy group. The aromatic group is as described above.

In view of achieving all of film defect reduction, compound stability, sensitivity, and etching resistance, the compound represented by the above formula (a) is preferably a compound represented by the formula (a1):

(a1)

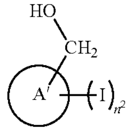

In the formula (a1), A' and $n^2$ are as described above.

In view of achieving all of film defect reduction, sensitivity, and etching resistance, the compound represented by the above formula (a) is preferably a compound represented by the formula (a2):

(a2)

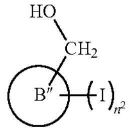

In the formula (a2), B" represents an organic group containing an aromatic group and having 5 to 30 carbon atoms, B" has at least one hydroxy group, and $n^2$ is as defined in the above formula (1). B" is the same as B in the above formula (3) except that B" contains at least one hydroxy group instead of the acyl group in B in the above formula (3). When a hydroxy group is contained as a substituent in the compound serving as the skeleton of B", the stability of the compound and the (co)polymer is further enhanced, and the resin into which the compound and the (co)polymer are introduced is satisfactorily dissolved in an organic solvent and is more excellent in storage stability, and thus the number of hydroxy groups in the compound serving as the skeleton of B" is preferably 1 to 8, more preferably 1 to 5, still more preferably 1 to 3, and further preferably 1. The compound serving as the skeleton of B" is the same as the compound serving as the skeleton of B described above.

In view of achieving all of film defect reduction, sensitivity, and etching resistance, in the formula (a2), it is preferable that B" is an aromatic group having 5 to 30 carbon atoms optionally having a substituent, and B" has at least one hydroxy group; and it is more preferable that B" is benzene optionally having a substituent, and B" has at least one hydroxy group. The aromatic group is as described above.

In view of achieving all of film defect reduction, compound stability, sensitivity, and etching resistance, the compound represented by the above formula (a) is preferably a compound represented by the formula (a3):

(a3)

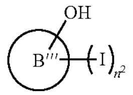

In the formula (a3), B'" represents an organic group containing an alicyclic ring and having 5 to 30 carbon atoms, B'" has at least one hydroxy group, and $n^2$ is as defined in the above formula (1). B'" is the same as B' in the above formula (3') except that B'" contains at least one hydroxy group instead of the acyl group in B' in the above formula (3'). When a hydroxy group is contained as a substituent in the compound serving as the skeleton of B'", the stability of the compound and the (co)polymer is further enhanced, and the resin into which the compound and the (co)polymer are introduced is satisfactorily dissolved in an organic solvent and is more excellent in storage stability, and thus the number of hydroxy groups in the compound serving as the skeleton of B'" is preferably 1 to 10, more preferably 1 to 5, still more preferably 1 to 3, and further preferably 1. The compound serving as the skeleton of B'" is the same as the compound serving as the skeleton of B' described above.

In view of achieving all of film defect reduction, compound stability, sensitivity, and etching resistance, in the formula (a3), it is preferable that B'" is an alicyclic ring having 5 to 30 carbon atoms optionally having a substituent, and B'" has at least one hydroxy group; it is more preferable that alicyclic hydrocarbon having 5 to 30 carbon atoms optionally having a substituent, and B'" has at least one hydroxy group; and it is still more preferable that adamantane optionally having a substituent, and B'" has at least one hydroxy group. The alicyclic ring and alicyclic hydrocarbon are as described above.

Specific examples of the (meth)acrylic acid compound represented by the formula (b) of the present embodiment are shown below, but are not limited thereto. In the following examples, $R^1$ represents a hydrogen atom, a methyl group, or halogen. $R^1$ may be the same or different.

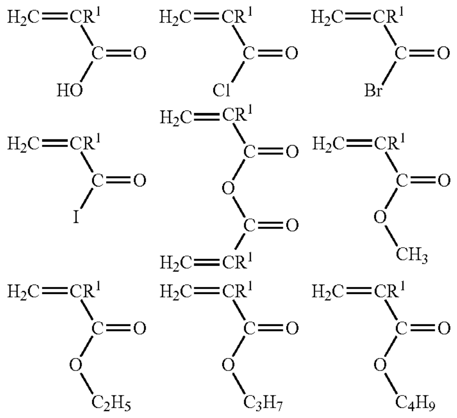

<Method for Producing Iodine-Containing Hydroxy Compound Represented by Formula (a)>

Next, a method for producing an iodine-containing hydroxy compound represented by the formula (a) will be described.

An example of the production of the iodine-containing hydroxy compound represented by the formula (a) is not particularly limited, and an iodine introduction reaction can be performed to produce a compound represented by the formula (Sa1) or (Sa2). When the compound of the formula (Sa2) is performed to an iodine introduction reaction, the method further includes a step of converting the iodine-introduced product into the compound of the formula (a).

In the present embodiment, an iodine-introduced product obtained by introducing iodine into the compound of the formula (Sa2) in advance may be used. Examples of such iodine-introduced products include 3,5-diiodosalicylaldehyde and 4-hydroxy-3,5-diiodobenzaldehyde. The step of converting to the compound of the formula (a) includes, for example, a reduction step.

(Sa1)

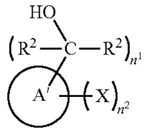

In the formula (Sa1), $R^2$, A', $n^1$, and $n^2$ are as described above. X may be selected from the group consisting of a hydroxy group; an aliphatic group having 1 to 30 carbon atoms or an aromatic group, the aliphatic group or the aromatic group having at least one selected from the group consisting of a hydroxy group, an aldehyde group and a carboxyl group; or halogen (F, Cl, Br, or the like). Examples of the compound of the formula (Sa1) include, for example, salicyl alcohol, 4-hydroxybenzyl alcohol, salicyclic acid, 4-hydroxybenzoic acid, 1,3,5-adamantanetriol, 1,3-adamantanediol, 1-adamantaneol, and 2-adamantaneol.

(Sa2)

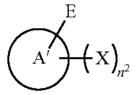

In the formula (Sa2), A' and $n^2$ are as described above. X is as defined in the formula (Sa1). E is a hydrocarbon group having 1 to 30 carbon atoms and having at least one selected from the group consisting of a hydroxy group, an aldehyde group, a carboxyl group, an ether group, a thiol group, and an amino group. Examples of the compound of the formula (Sa2) include, for example, salicylaldehyde and 4-hydroxybenzaldehyde.

As the iodine introduction reaction, Sandmeyer method; Halex method; iodine introduction method using an iodinating agent or a compound serving as an iodine source; iodine introduction method using an iodinating agent or a compound serving as an iodine source and an oxidizing agent; iodine introduction method using an iodinating agent or a compound serving as an iodine source and a radical generating agent; iodine introduction method using a system in which catalytic activity is improved by an iodinating agent or a compound serving as an iodine source and zeolite or the like; a method in which iodination is carried out by substitution reaction with a functional group such as a hydroxy group or a halogen group, and the like can be arbitrarily used.

As the iodinating agent, a publicly known compound serving as an iodine supply source such as iodine, potassium iodide, hydrogen iodide (HI), iodine chloride, or N-iodosuccinimide can be arbitrarily used. These iodinating agents are used alone or in combination of two or more thereof.

As the oxidizing agent, a publicly known oxidizing agent such as hydrogen peroxide, iodic acid, periodic acid and sulfuric acid can be used. These oxidizing agents are used alone or in combination of two or more thereof.

<Method for Producing Iodine-Containing Hydroxy (Meth) Acrylic Acid Compound>

Next, a method for producing an iodine-containing hydroxy (meth)acrylic acid compound will be described.

The iodine-containing hydroxy compound represented by the formula (a) is used in an amount of, for example, 0.5 to 100 molar equivalents, preferably 1 to 20 molar equivalents, and still more preferably 1.2 to 5 molar equivalents, based on the (meth)acrylic acid compound represented by the formula (b). Within this range, the reaction proceeds sufficiently, and the yield of the iodine-containing hydroxy (meth)acrylic acid compound, which is the objective product, is high and thus preferable.

As the solvent used in this reaction, solvents that are generally available can be used. For example, an alcohol, an ether, a hydrocarbon, an aromatic solvent, a halogen-based solvent, or the like can be appropriately used as long as the reaction is not inhibited. A mixture of a plurality of solvents may be used as long as the reaction is not inhibited. Since water inhibits the reaction, it is preferable to use a dehydrated solvent. Examples of the solvent include solvents described herein.

As such a solvent, a solvent having good solubility is preferably used for the purpose of improving the stability of the material and the efficiency in the process from the reaction to the acquisition of the final compound. As a preferable solvent, γP and γH in Hansen Solubility Parameters (A User's Handbook, CRC Press, Boca Raton FL, 2007) can be used as indices, and γP and γH can be determined from the compound structure. γP and γH are preferably lower, and the γP value is preferably 6 or less, more preferably 4 or less, and still more preferably 2 or less. The γH value is preferably 6 or less, more preferably 4 or less, and still more preferably 2 or less. As such a solvent, aromatic solvents such as benzene, toluene, and xylene; aliphatic hydrocarbon-based solvents such as hexane, heptane, and octane; and halogen-based solvents such as dichloromethane, dichloroethane, and chloroform are preferably used as a main solvent.

The reaction temperature and the reaction time depend on the substrate concentration and the catalyst used, but in general, the reaction can be carried out at a reaction temperature of −20° C. to 100° C. for a reaction time of 1 hour to 30 hours under normal pressure, reduced pressure or increased pressure. The reaction can be carried out by appropriately selecting a publicly known method such as a batch system, a semi-batch system, or a continuous system.

In addition, a polymerization inhibitor may be added to the series of reactions, and commercially available products that are generally available can be used. Examples of such a polymerization inhibitor include nitroso compounds such as 2,2,6,6-tetramethyl-4-hydroxypiperidine-1-oxyl, N-nitrosophenylhydroxyamine ammonium salt, N-nitrosophenylhydroxyamine aluminum salt, N-nitroso-N-(1-naphthyl) hydroxyamine ammonium salt, N-nitrosodiphenylamine, N-nitroso-N-methylaniline, nitrosonaphthol, p-nitrosophenol, and N,N'-dimethyl-p-nitrosoaniline; sulfur-containing compounds such as phenothiazine, methylene blue and 2-mercaptobenzimidazole; amines such as N,N'-diphenyl-p-phenylenediamine, N-phenyl-N'-isopropyl-p-phenylenediamine, 4-hydroxydiphenylamine and aminophenol; quinones such as hydroxyquinoline, hydroquinone, methylhydroquinone, p-benzoquinone and hydroquinone monomethyl ether; phenols such as 4-methoxyphenol, 2,4-dimethyl-6-t-butylphenol, catechol, 3-s-butylcatechol, and 2,2-methylenebis-(6-t-butyl-4-methylphenol); imides such as N-hydroxyphthalimide; oximes such as cyclohexane oxime and p-quinonedioxime; and dialkylthiodipropionate. The amount added is, for example, 0.001 to 10 parts by mass, or preferably 0.01 to 1 part by mass based on 100 parts by mass of the (meth)acrylic acid compound represented by the formula (b).

A catalyst may be added to the series of reactions, and a wide variety of catalysts functioning under the reaction conditions of the present embodiment are used. As such a catalyst, for example, an acid catalyst or a base catalyst is preferable.

Examples of suitable acid catalysts include an inorganic acid such as hydrochloric acid, sulfuric acid, phosphoric acid, hydrobromic acid, and hydrofluoric acid; an organic acid such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; a Lewis acid such as zinc chloride, aluminum chloride, iron chloride, and boron trifluoride; and a solid acid such as tungstosilicic acid, tungstophosphoric acid, silicomolybdic acid, and phosphomolybdic acid. These acid catalysts are used alone or in combination of two or more thereof. Among these, organic acids and solid acids are preferable from the viewpoint of production, and it is preferable to use p-toluenesulfonic acid, hydrochloric acid, or sulfuric acid from the viewpoint of production such as easy availability and handleability.

Examples of suitable base catalysts include amine-containing catalysts such as pyridine and ethylenediamine; and non-amine basic catalysts such as metal salts. The metal salt is preferably a potassium salt or an acetate salt, and examples of such a catalyst include potassium acetate, potassium carbonate, potassium hydroxide, sodium acetate, sodium carbonate, sodium hydroxide, and magnesium oxide.

Non-amine base catalysts are commercially available, for example, from EM Science and Aldrich.

These catalysts are used alone or in combination of two or more thereof.

The amount of the catalyst to be used can be appropriately set according to the substrate to be used, the catalyst, the reaction conditions, or the like, and is not particularly limited, but in general, is suitably 1 to 5000 parts by mass, and is preferably 50 to 3000 parts by mass based on 100 parts by mass of the reaction raw materials from the viewpoint of the yield.

The iodine-containing hydroxy (meth)acrylic acid compound obtained by the reaction can be isolated and purified by a publicly known purification method such as a separation and purification method using filtration, concentration, distillation, extraction, crystallization, recrystallization, column chromatography, activated carbon, or the like, or a method using a combination thereof to obtain a desired high-purity monomer. Further, for the purpose of removing metal-containing impurities such as metal ions and metal oxides contained in the obtained high-purity monomer, a purification method for the purpose of removing metal impurities described later may be added. In the obtained high-purity monomer, the content of various metals (for example, sodium (Na), potassium (K), calcium (Ca), magnesium (Mg), iron (Fe), copper (Cu), nickel (Ni), tin (Sn), silver (Ag), molybdenum (Mo), manganese (Mn), zinc (Zn), cobalt (Co), aluminum (Al), lead (Pb), chromium (Cr), and titanium (Ti)) in the compound is usually 10 ppb or less, preferably 5 ppb or less, and more preferably 1 ppb or less.

The reaction liquid may be subjected to acylation as it is without isolation and purification of the iodine-containing hydroxy (meth)acrylic acid compound.

The purification method for removing metal impurities include, but not particularly limited to, a step of dissolving the iodine-containing hydroxy (meth)acrylic acid compound in a solvent to obtain a solution (S), and a step of bringing the solution (S) into contact with an acidic aqueous solution to extract impurities in the iodine-containing hydroxy (meth) acrylic acid compound (hereinafter also referred to as "compound (A)") (first extraction step), and the solvent used in the step of obtaining a solution (S) includes an organic solvent that does not inadvertently mix with water.

According to such a purification method, the contents of various metals contained as impurities in the compound (A) can be reduced.

More specifically, the compound (A) is dissolved in an organic solvent that does not inadvertently mix with water to obtain the solution (S), and further, extraction treatment can be carried out by bringing the solution (S) into contact with an acidic aqueous solution. Thereby, extracted metals contained in the solution (S) are transferred to the aqueous phase, then the organic phase and the aqueous phase are separated, and thus the compound (A) having a reduced metal content can be obtained.

The organic solvent that does not inadvertently mix with water used in the purification method of the present embodiment is not particularly limited, but is preferably an organic solvent that is safely applicable to semiconductor manufacturing processes. Specifically, the organic solvent preferably has a solubility in water at room temperature (25° C.) of less than 30%, more preferably less than 20%, and still more preferably less than 10%. The amount of the organic solvent used is preferably 1 to 100 times parts by mass based on the total amount of the compound (A) to be used.

Specific examples of the solvent that does not inadvertently mix with water include ethers such as diethyl ether and diisopropyl ether; esters such as ethyl acetate, n-butyl acetate, and isoamyl acetate; ketones such as methyl ethyl ketone, methyl isobutyl ketone, ethyl isobutyl ketone, cyclohexanone, cyclopentanone, 2-heptanone, and 2-pentanone; glycol ether acetates such as ethylene glycol monoethyl ether acetate, ethylene glycol monobutyl ether acetate, propylene glycol monomethyl ether acetate (PGMEA), and propylene glycol monoethyl ether acetate; aliphatic hydrocarbons such as n-hexane and n-heptane; aromatic hydrocarbons such as toluene and xylene; and halogenated hydrocarbons such as methylene chloride and chloroform. Among these, toluene, 2-heptanone, cyclohexanone, cyclopentanone, methyl isobutyl ketone, propylene glycol monomethyl ether acetate, ethyl acetate, and the like are preferable, methyl isobutyl ketone, ethyl acetate, cyclohexanone, and propylene glycol monomethyl ether acetate are more preferable, and methyl isobutyl ketone and ethyl acetate are still more preferable. Methyl isobutyl ketone and ethyl acetate have relatively high saturation solubility for the compound (A) and a relatively low boiling point, and it is thus possible to reduce the load in the case of industrially distilling off the solvent and in the step of removing the solvent by drying. These solvents are used alone or in combination of two or more thereof.

The acidic aqueous solution used in the purification method is arbitrarily selected from among acidic aqueous solutions in which organic compounds or inorganic compounds are dissolved in water, generally known as acidic aqueous solutions. Examples of such an aqueous solution include, for example, aqueous mineral acid solutions obtained by dissolving mineral acids such as hydrochloric acid, sulfuric acid, nitric acid, and phosphoric acid in water; and aqueous organic acid solutions obtained by dissolving organic acids such as acetic acid, propionic acid, polycarboxylic acids such as oxalic acid, malonic acid, succinic acid, fumaric acid, maleic acid, tartaric acid, and citric acid, methanesulfonic acid, phenolsulfonic acid, p-toluenesulfonic acid, and trifluoroacetic acid in water. These acidic aqueous solutions are used alone or in combination of two or more thereof. Among these acidic aqueous solutions, an aqueous solution of sulfuric acid, nitric acid, and a polycarboxylic acid such as acetic acid, oxalic acid, tartaric acid and citric acid are preferable; an aqueous solution of sulfuric acid, oxalic acid, tartaric acid and citric acid are more preferable; and an aqueous solution of oxalic acid is still more preferable. It is considered that polyvalent carboxylic acids such as oxalic acid, tartaric acid and citric acid coordinate with metal ions and provide a chelating effect, and thus tend to be capable of more effectively removing metals. Also, as for water used herein, it is preferable to use water, the metal content of which is small, such as ion exchanged water, according to the purpose of the purification method in the present embodiment.

The pH of the acidic aqueous solution used in the purification method is not particularly limited, but it is preferable to regulate the acidity of the aqueous solution in consideration of an influence on the compound (A). Normally, the pH range is about 0 to 5, and is preferably about 0 to 3.

The amount of the acidic aqueous solution to be used in the purification method is not particularly limited, but it is preferable to regulate the amount from the viewpoint of reducing the number of extraction operations for removing metals and ensuring operability in consideration of the overall amount of fluid. From the above viewpoints, the amount of the acidic aqueous solution to be used is preferably 10 to 200% by mass, more preferably 20 to 100% by mass, based on 100% by mass of the solution (S).

In the purification method, by bringing the acidic aqueous solution as described above into contact with the solution (S), metals can be extracted from the compound (A) in the solution (S).

In the purification method, the solution (S) may further contain an organic solvent that inadvertently mixes with water. When the solution (A) contains an organic solvent that inadvertently mixes with water, there is a tendency that the amount of the compound (A) to be charged can be increased, also the fluid separability is improved, and purification can be carried out at a high reaction vessel efficiency. Examples of the method for adding the organic solvent that inadvertently mixes with water include, for example, a method involving adding it to the organic solvent-containing solution in advance, a method involving adding it to water or the acidic aqueous solution in advance, and a method involving adding it after bringing the organic solvent-containing solution into contact with water or the acidic aqueous solution. Among these, the method involving adding it to the organic solvent-containing solution in advance is preferable from the viewpoint of the workability of operations and the ease of managing the amount.

The organic solvent that inadvertently mixes with water used in the purification method of the present embodiment is not particularly limited, but is preferably an organic solvent that is safely applicable to semiconductor manufacturing processes. The amount of the organic solvent used that inadvertently mixes with water is not particularly limited as long as the solvent phase and the aqueous phase separate, but is preferably 0.1 to 100 times parts by mass, more preferably 0.1 to 50 times parts by mass, and further preferably 0.1 to 20 times parts by mass based on the total amount of the compound (A).

Examples of the organic solvent used in the purification method that inadvertently mixes with water include, ethers such as tetrahydrofuran and 1,3-dioxolane; alcohols such as methanol, ethanol, and isopropanol; ketones such as acetone and N-methylpyrrolidone; aliphatic hydrocarbons such as glycol ethers such as ethylene glycol monoethyl ether, ethylene glycol monobutyl ether, propylene glycol monomethyl ether (PGME), and propylene glycol monoethyl ether. Among them, N-methylpyrrolidone, propylene glycol monomethyl ether, and the like are preferable. These solvents are used alone or in combination of two or more thereof.

The temperature at which the above extraction treatment is carried out is not particularly limited, but is generally in the range of 20 to 90° C., and preferably 30 to 80° C. The extraction operation is carried out, for example, by thoroughly mixing by stirring or the like to obtain a mixed solution and then leaving the obtained mixed solution to stand still. Thereby, metals contained in the solution (S) are transferred to the aqueous phase. Also, by this operation, the acidity of the solution is lowered, and the deterioration of the compound (A) can be suppressed.

By being left to stand still, the mixed solution is separated into an aqueous phase and a solvent phase containing the compound (A) and the solvent, and thus the solvent phase is recovered by decantation. The time for leaving the mixed solution to stand still is not particularly limited, but it is preferable to regulate the time for leaving the mixed solution to stand still from the viewpoint of attaining good separation of the solvent phase and the aqueous phase. Normally, the time to stand still is 1 minute or longer, preferably 10 minutes or longer, and more preferably 30 minutes or longer. In addition, while the extraction treatment may be carried out only once, it is also effective to repeat mixing, leaving-to-stand-still, and separating operations multiple times.

It is preferable that the purification method include a step of further bringing the solvent phase containing the compound (A) into contact with water after the first extraction step, thereby extracting impurities in the compound (A) (a second extraction step). Specifically, for example, it is preferable that after the above extraction treatment is carried out using an acidic aqueous solution, the aqueous solution is recovered, and the remaining solvent phase containing the compound (A) and the solvent is further subjected to an extraction treatment with water. The extraction treatment by the second extraction step is not particularly limited, and can be carried out by, for example, thoroughly mixing the solvent phase and water by stirring or the like and then leaving the obtained mixed solution to stand still. The mixed solution after being left to stand still is separated into an aqueous phase and a solvent phase containing the compound (A) and the solvent, and the solvent phase can thus be recovered by decantation or the like.

Water used herein is preferably water, the metal content of which is small, such as ion exchanged water, according to the purpose of the present embodiment. While the extraction treatment may be carried out only once, it is also effective to repeat mixing, leaving-to-stand-still, and separating operations multiple times. Conditions such as the ratio of use of both in the extraction treatment, the temperature, and the time are not particularly limited, but the above may be referred to.

Water that is possibly present in the thus-obtained solution containing the compound (A) and the solvent can be easily removed by performing vacuum distillation or a like operation. Also, if required, the concentration of the compound (A) can be regulated to be any concentration by adding a solvent to the solution.

The purification method of the compound (A) can also be performed by passing a solution obtained by dissolving the compound (A) in a solvent through a filter.

According to the purification method of the present embodiment, the content of various metals in the compound (A) can be effectively and significantly reduced.

Herein, the term "passed through" of the present embodiment means that the above solution is passed from the outside of the filter through the inside of the filter and is allowed to move out of the filter again, and for example, an aspect in which the solution is simply brought into contact with the surface of the filter and an aspect in which the solution is brought into contact on the surface while being allowed to move outside an ion-exchange resin (that is, an aspect in which the solution is simply brought into contact) are excluded.

The purification method using a filter will be described in detail.

Commercially available filters for liquid filtration can be usually used as the filter. The filtration accuracy of the filter is not particularly limited, but the nominal pore size of the filter is preferably 0.2 μm or less, more preferably less than 0.2 μm, still more preferably 0.1 μm or less, further preferably less than 0.1 μm, and still further preferably 0.05 μm or less. The lower limit of the nominal pore size of the filter is not particularly limited, but is usually 0.005 μm. As used herein, the term "nominal pore size" refers to the pore size nominally used to indicate the separation performance of the filter, which is determined, for example, by any method specified by the filter manufacturer, such as a bubble point test, a mercury intrusion test or a standard particle trapping test. When using a commercially available product, the nominal pore size is a value described in the manufacturer's catalog data. The nominal pore size of 0.2 μm or less makes it possible to effectively reduce the contents of the metal components after passing the solution through the filter once. The step of passing a solution through a filter may be performed twice or more to reduce the more content of each metal component in the solution.

Examples of the forms of the filter to be used include a hollow fiber membrane filter, a membrane filter, a pleated membrane filter, and a filter filled with a filter medium such as a non-woven fabric, cellulose or diatomaceous earth. Among the above, the filter is preferably one or more selected from the group consisting of a hollow fiber membrane filter, a membrane filter and a pleated membrane filter. Further, it is particularly preferable to use a hollow fiber membrane filter, in particular due to its high precision filtration accuracy and its higher filtration area than other forms.

Examples of the material for the filter include a polyolefin such as polyethylene and polypropylene; a polyethylene-based resin having a functional group having an ion exchange capacity provided by graft polymerization; a polar group-containing resin such as polyamide, polyester and polyacrylonitrile; and a fluorine-containing resin such as fluorinated polyethylene (PTFE). Among the above, the material for the filter is preferably one or more selected from the group consisting of a polyamide, a polyolefin resin, and a fluororesin. A polyamide is further preferable from the viewpoint of the reduction effect of heavy metals such as chromium. From the viewpoint of avoiding metal elution from the material, it is preferable to use a filter other than the sintered metal material.

Examples of the polyamide-based filter can include: Polyfix® nylon series manufactured by KITZ MICROFILTER CORPORATION; Ultipleat® P-Nylon 66 and Ultipor® N66 manufactured by Nihon Pall Ltd.; and LifeASSURE® PSN series and LifeASSURE® EF series manufactured by 3M Company.

Examples of polyolefin-based filter can include: Ultipleat® PE Clean and Ion Clean manufactured by Nihon Pall Ltd.; Protego® series, Microgard® Plus HC10 and Optimizer D manufactured by Entegris Japan Co., Ltd.

Examples of the polyester-based filter can include: Geraflow DFE manufactured by Central Filter Mfg. Co., Ltd.; and a pleated Type® PMC manufactured by Nihon Filter Co., Ltd.

Examples of the polyacrylonitrile-based filter can include: Ultrafilters AIP-0013D, ACP-0013D and ACP-0053D manufactured by Advantec Toyo Kaisha, Ltd.

Examples of the fluororesin-based filter can include: Emflon® HTPFR manufactured by Nihon Pall Ltd.; and LifeASSURE FA series manufactured by 3M Company.

These filters can be used alone or in combination of two or more thereof.

The filter may also contain an ion exchanger such as a cation-exchange resin, or a cation charge controlling agent and the like that causes a zeta potential in an organic solvent solution to be filtered.

Examples of the filter containing an ion exchanger can include: Protego® series manufactured by Entegris Japan Co., Ltd.; and KURANGRAFT® manufactured by Kurashiki Textile Manufacturing Co., Ltd.

Examples of the filter containing a material having a positive zeta potential such as a cationic polyamide-polyamine-epichlorohydrin resin include: Zeta Plus® 40QSH and Zeta Plus® 020GN and LifeASSURE® EF series manufactured by 3M company.

The method for isolating the compound (A) from the obtained solution containing the compound (A) and the solvents is not particularly limited, and publicly known methods can be carried out, such as reduced-pressure removal, separation by reprecipitation, and a combination thereof. Publicly known treatments such as concentration operation, filtration operation, centrifugation operation, and drying operation can be carried out if required.

<Method for Producing Iodine-Containing (Meth)Acrylate Compound>

Next, a method for producing the iodine-containing (meth)acrylate compound of the present embodiment will be described.

The iodine-containing (meth)acrylate compound can be obtained by reacting a hydroxy group in an iodine-containing hydroxy (meth)acrylic acid compound with an acylating agent. Examples of suitable acylating agents include, but not particularly limited to, acetic anhydride, acetyl halide, and acetic acid. Among these, acetic anhydride is preferable.

This reaction may be carried out in an organic solvent. As the organic solvent, a wide variety of organic solvents are used, including polar aprotic organic solvents and protic polar organic solvents. A single protic polar solvent or a single polar aprotic solvent can be used. Furthermore, it is possible to use mixtures of polar aprotic solvents, mixtures of protic polar solvents, mixtures of polar aprotic solvents with protic polar solvents and mixtures of aprotic or protic solvents with nonpolar solvents. Among these, polar aprotic solvents or mixtures thereof are preferred.

The solvent is effective but not an essential component. Examples of suitable polar aprotic solvents include, for example, alcohol-based solvents such as methanol and ethanol; ether-based solvents such as diethyl ether, tetrahydrofuran, dimethoxyethane, diglyme, and triglyme; ester-based solvents such as ethyl acetate and γ-butyrolactone; nitrile solvents such as acetonitrile; hydrocarbon-based solvents such as toluene and hexane; amide-based solvents such as N,N-dimethylformamide, 1-methyl-2-pyrrolidinone, N,N- dimethylacetamide, hexamethylphosphoramide, and hexamethylphosphorous triamide; and dimethyl sulfoxide. Among them, toluene and dimethyl sulfoxide are preferable. Examples of suitable protic polar solvents include di(propylene glycol)methyl ether, di(ethylene glycol)methyl ether, 2-butoxyethanol, ethylene glycol, 2-methoxyethanol, propylene glycol methyl ether, n-hexanol, and n-butanol.

The amount of the solvent to be used can be appropriately set according to the substrate to be used, the catalyst, the reaction conditions, or the like, and is not particularly limited, but in general, is suitably 0 to 10000 parts by mass, and is preferably 100 to 2000 parts by mass based on 100 parts by mass of the reaction raw materials from the viewpoint of the yield.

A catalyst may be used for this reaction. As the catalyst, a wide variety of acylation catalysts functioning under the reaction conditions of the present embodiment are used, and an acid catalyst or a base catalyst is preferable.

Examples of suitable acid catalysts include an inorganic acid such as hydrochloric acid, sulfuric acid, phosphoric acid, hydrobromic acid, and hydrofluoric acid; an organic acid such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; a Lewis acid such as zinc chloride, aluminum chloride, iron chloride, and boron trifluoride; and a solid acid such as tungstosilicic acid, tungstophosphoric acid, silicomolybdic acid, and phosphomolybdic acid. These acid catalysts are used alone or in combination of two or more thereof. Among these, organic acids and solid acids are preferable from the viewpoint of production, and hydrochloric acid or sulfuric acid is more preferably used from the viewpoint of production such as easy availability and handleability.

Examples of suitable base catalysts include amine-containing catalysts such as pyridine and ethylenediamine; and non-amine basic catalysts such as metal salts. The metal salt is preferably a potassium salt or an acetate salt. Examples of such a catalyst include potassium acetate, potassium carbonate, potassium hydroxide, sodium acetate, sodium carbonate, sodium hydroxide, and magnesium oxide.

Non-amine base catalysts are commercially available, for example, from EM Science and Aldrich.

These catalysts are used alone or in combination of two or more thereof.

The amount of the catalyst to be used can be appropriately set according to the substrate to be used, the catalyst, the reaction conditions, or the like, and is not particularly limited, but in general, is suitably 1 to 5000 parts by mass, and is preferably 50 to 3000 parts by mass based on 100 parts by mass of the reaction raw materials from the viewpoint of the yield.

A polymerization inhibitor may be used for this reaction. As the polymerization inhibitor, a wide variety of polymerization inhibitors functioning under the reaction conditions of the present embodiment are used. The polymerization inhibitor is effective but not an essential component. Examples of suitable polymerization inhibitors include, in addition to those described herein, for example, hydroquinone, hydroquinone monomethylether, 4-tert-butyl catechol, phenothiazine, N-oxyl(nitroxide) inhibitors, including Prostab® 5415 (bis(1-oxyl-2,2,6,6-tetramethylpiperidine-4-yl) sebacate, available from Ciba Specialty Chemicals), 4-hydroxy-TEMPO (4-hydroxy-2,2,6,6-tetramethylpiperidin-1-yloxy, available from Tokyo Chemical Industry Co., Ltd.) and Uvinul® 4040 P (1,6-hexamethylene-bis(N-formyl-N-(1-oxyl-2,2,6,6-tetramethylpiperidine-4-yl)amine, available from BASF Corp.). These polymerization inhibitors are used alone or in combination of two or more thereof.

The amount of the polymerization inhibitor to be used can be appropriately set according to the substrate to be used, the catalyst, the reaction conditions, or the like, and is not particularly limited, but in general, is suitably 0.0001 to 100 parts by mass, and is preferably 0.001 to 10 parts by mass based on 100 parts by mass of the reaction raw materials from the viewpoint of the yield.

A polymerization suppressor may be used for this reaction. As the polymerization suppressor, a wide variety of polymerization suppressors functioning under the reaction conditions of the present embodiment are used. The polymerization suppressor is effective but not an essential component. Examples of the polymerization suppressor include hydroquinone, methoquinone, methoxyphenol, hydroxyanisole, di-t-butylhydroquinone, toluhydroquinone, butylhydroquinone, benzoquinone, methyl-p-benzoquinone, toluquinone, butyl-p-benzoquinone, and diphenyl-p-benzoquinone. These polymerization suppressors are used alone or in combination of two or more thereof.

It is also effective to use a polymerization retarder in combination with a polymerization suppressor. Polymerization retarders are well known in the art and are compounds that slow down the polymerization reaction but do not prevent all polymerization. Common polymerization retarders are aromatic nitro compounds such as dinitro-ortho-cresol (DNOC) and dinitrobutylphenol (DNBP). Methods for producing polymerization retarders are common and well known in the art (see for example U.S. Pat. No. 6,339,177; Park et al., Polymer (Korea) (1988), 12(8), 710-19) and their use in the control of styrene polymerization is well documented (see for example Bushby et al., Polymer (1998), 39(22), 5567-5571). These polymerization retarders are used alone or in combination of two or more thereof.

The amount of the polymerization retarder to be used can be appropriately set according to the substrate to be used, the catalyst, the reaction conditions, or the like, and is not particularly limited, but in general, is suitably 0.0001 to 100 parts by mass, and is preferably 0.001 to 10 parts by mass based on 100 parts by mass of the reaction raw materials from the viewpoint of the yield.

In the reaction, an iodine-containing hydroxy (meth) acrylic acid compound, an acylating agent, and optionally an organic solvent, a catalyst, a polymerization inhibitor, a polymerization suppressor, and a polymerization retarder are added to a reactor to form a reaction mixture. Any suitable reactor may be used for the reaction. The reaction can be carried out by appropriately selecting a publicly known method such as a batch system, a semi-batch system, or a continuous system.

The reaction temperature depends on the concentration of the substrate, the stability of the product formed, the choice of catalyst and the desired yield and is not particularly limited. In general, a temperature of 0 to 200° C. is suitable, and from the viewpoint of yield, a temperature of 0 to 100° C. is preferable.

The reaction pressure depends on the concentration of the substrate, the stability of the product formed, the choice of catalyst and the desired yield and is not particularly limited. The pressure can be adjusted using an inert gas such as nitrogen or using an intake pump or the like. Conventional pressure reactors, including shaker vessels, rocker vessels, and agitated autoclaves, are used for high-pressure reactions.

The reaction time depends on the concentration of the substrate, the stability of the product formed, the choice of catalyst and the desired yield and is not particularly limited. Usually, most of the reaction is carried out in less than 12 hours, and the reaction time is generally 15 to 600 minutes.

Isolation and purification can be carried out after completion of the reaction using any suitable method publicly known in the art. For example, the reaction mixture is poured onto ice water and extracted into an organic solvent such as ethyl acetate, butyl acetate, and diethyl ether. The product is then recovered by removing the solvent using evaporation at reduced pressure. The iodine-containing (meth)acrylate compound can be isolated and purified by a purification method well known in the art such as a separation and purification method using filtration, concentration, distillation, extraction, crystallization, recrystallization, column chromatography, activated carbon, or the like, or a method using a combination thereof to obtain a desired high-purity monomer. Further, for the purpose of removing metal-containing impurities such as metal ions and metal oxides contained in the obtained high-purity monomer, a purification method for the purpose of removing metal impurities may be added. For the details of the purification method, reference can be made to the methods described herein, such as the above and Examples. In the obtained high-purity monomer, the content of various metals (for example, Na, K, Ca, Mg, Fe, Cu, Ni, Sn, Ag, Mo, Mn, Zn, Co, Al, Pb, Cr, and Ti) in the compound is usually 10 ppb or less, preferably 5 ppb or less, and more preferably 1 ppb or less.

The compound of the present embodiment can be utilized widely and effectively in, for example, electrical insulating materials, resins for resists, encapsulation resins for semiconductors, adhesives for printed circuit boards, electrical laminates mounted in electric equipment, electronic equipment, industrial equipment, and the like, matrix resins of prepregs mounted in electric equipment, electronic equipment, industrial equipment, and the like, buildup laminate materials, resins for fiber-reinforced plastics, resins for encapsulation of liquid crystal display panels, coating materials, various coating agents, adhesives, coating agents for semiconductors, resins for resists for semiconductors, resins for resist underlayer film formation, and the like.

[Iodine-Containing (Meth)Acrylate (Co)Polymer]

The compound of the present embodiment has high stability, and even an iodine-containing (meth)acrylate (co) polymer containing this compound as a constituent unit has high stability, and the (co)polymer can be efficiently produced.

By forming a (co)polymer containing the compound of the present embodiment as a constituent unit, a polymer containing one or more halogen elements, one or more hydrophilic groups or one or more decomposable groups can be formed. As a result, a resist composition containing a (co)polymer containing the compound of the present embodiment as a constituent unit as a resin component can achieve high sensitivity in a lithography process and high resolution by increasing the solubility contrast of the resin in development.

The (co)polymer of the present embodiment has a constituent unit represented by the following formula (4):

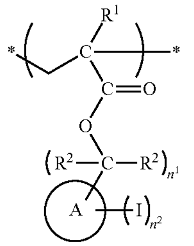

(4)

In the formula (4), $R^1$, $R^2$, A, $n^1$, and $n^2$ are as defined in the above formula (1), and the symbol * represents a bonding site to an adjacent constituent unit. In view of achieving both sensitivity and etching resistance, $n^2$ is an integer of 1 to 20, preferably an integer of 1 to 20, more preferably an integer of 1 to 10, and still more preferably an integer of 2 to 5.

A contains at least one acyl group. The acyl group is as described above. Among them, an ethanoyl group (acetyl group) and a benzoyl group are preferable, and an ethanoyl group (acetyl group) is more preferable.

It is preferable that A contains at least one acyl group from the viewpoint of enhancing the stability of the (co)polymer. It is also preferable from the viewpoint of enhancing the productivity of the (co)polymer. When an acyl group is contained as a substituent in the compound serving as the skeleton of A, the stability of the compound and the (co) polymer is further enhanced, and the resin into which the compound and the (co)polymer are introduced is satisfactorily dissolved in an organic solvent and is more excellent in storage stability, and thus the number of acyl groups in the compound serving as the skeleton of A is preferably 1 to 10, more preferably 1 to 5, still more preferably 1 to 3, and further preferably 1. The compound serving as the skeleton of A is as described above.

In a practical aspect, the (co)polymer can also be used by hydrolyzing a part or all of the acyl groups contained in A to form hydroxy groups. By having a hydroxy group, it is possible to obtain a (co)polymer having more excellent alkali developability and achieving all of film defect reduction, compound stability, and sensitivity. The (co)polymer may contain, together with the constituent unit represented by the formula (4), a constituent unit having a hydroxy group obtained by hydrolysis of a part or all of the acyl groups contained in A in the formula (4).

The (co)polymer can be obtained as a polymer composed of the compound of the present embodiment (homopolymer), a copolymer obtained by polymerizing two or more compounds of the present embodiment, or a copolymer obtained by polymerizing one or more compounds of the present embodiment and one or more other monomers. In the present embodiment, these polymers are collectively referred to as "(co)polymer". The (co)polymer can be used in a material for film formation for lithography, a material for resist film formation, and the like.

In view of achieving all of film defect reduction, compound stability, sensitivity, and etching resistance, in the formula (4), it is preferable that $n^1$ is 0 and A is preferably an alicyclic ring having 5 to 30 carbon atoms optionally having a substituent, it is more preferable that $n^1$ is 0 and A is alicyclic hydrocarbon having 5 to 30 carbon atoms optionally having a substituent, and it is still more preferable that $n^1$ is 0 and A is adamantane optionally having a substituent. The alicyclic ring and alicyclic hydrocarbon are as described above.

In view of achieving all of film defect reduction, sensitivity, and etching resistance, in the formula (4), it is preferable that $n^1$ is 1 and A is an aromatic group having 5 to 30 carbon atoms optionally having a substituent, and it is more preferable that $n^1$ is 1 and A is preferably benzene optionally having a substituent. The aromatic group is as described above.

The (co)polymer includes a constituent unit derived from the iodine-containing (meth)acrylate compound of the present embodiment, and preferred aspects of the iodine-containing (meth)acrylate compound are as described above.

The (co)polymer includes, for example, a constituent unit derived from the compound represented by the formula (1), the compound represented by the formula (2), the compound represented by the formula (3), and the compound represented by the formula (3'). The constituent unit derived from the compound represented by the formula (1) corresponds to the constituent unit represented by the formula (4), and the same interpretation applies to the compound represented by the formula (2), the compound represented by the formula (3), and the compound represented by the formula (3').

Examples of the other monomers include, but not particularly limited to, compounds (monomers) described in International Publication No. WO 2016/125782, International Publication No. WO 2015/115613, Japanese Patent Laid-Open No. 2015/117305, International Publication No. WO 2014/175275, and Japanese Patent Laid-Open No. 2012/162498. The copolymer may contain a constituent unit represented by the formula (Cl) and a constituent unit represented by the formula (C2). These monomers and constituent units are used alone or in combination of two or more thereof.

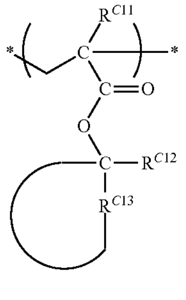

(C1)

In the formula (C1), $R^{C11}$ represents a hydrogen atom or a methyl group, $R^{C12}$ represents a hydrogen atom or an alkyl group having 1 to 4 carbon atoms, $R^{C13}$ together with the carbon atom to which $R^{C13}$ is bonded is a cycloalkyl group or a heterocycloalkyl group having 4 to 20 carbon atoms, and the symbol * represents a bonding site to an adjacent constituent unit. $R^{13}$ may have a substituent (for example, an oxo group).

Preferably, $R^{C12}$ represents a hydrogen atom or an alkyl group having 1 to 3 carbon atoms, and $R^{C13}$ together with the carbon atom to which $R^{C13}$ is bonded is a cycloalkyl group or a heterocycloalkyl group having 4 to 10 carbon atoms.

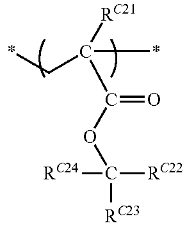

(C2)

In the formula (C2), $R^{C21}$ represents a hydrogen atom or a methyl group, $R^{C22}$ and $R^{C23}$ each independently represent an alkyl group having 1 to 4 carbon atoms, $R^{C24}$ represents an alkyl group having 1 to 4 carbon atoms or a cycloalkyl group having 5 to 20 carbon atoms, two or three of $R^{C22}$ to $R^{C24}$ may form an alicyclic structure having 3 to 20 carbon atoms together with the carbon atom to which they are bonded, and the symbol * represents a bonding site to an adjacent constituent unit. The alicyclic structure may have a substituent (for example, a hydroxy group or an alkyl group).

Preferably, $R^{C22}$ represents an alkyl group having 1 to 3 carbon atoms, and $R^{C24}$ represents a cycloalkyl group having 5 to 10 carbon atoms. The alicyclic structure formed by $R^{C22}$ to $R^{C24}$ may include a plurality of rings such as an adamantyl group.

Examples of the monomer raw material of the constituent unit represented by the formula (C2) include 2-methyl-2-(meth)acryloyloxyadamantane (2-methyl-2-adamantyl (meth)acrylate), 2-ethyl-2-(meth)acryloyloxyadamantane, 2-isopropyl-2-(meth)acryloyloxyadamantane, 2-n-propyl-2-(meth)acryloyloxyadamantane, 2-n-butyl-2-(meth)acryloyloxyadamantane, 3-hydroxy-1-adamantyl(meth)acrylate, 1-methyl-1-(meth)acryloyloxycyclopentane, 1-ethyl-1-(meth)acryloyloxycyclopentane, 1-methyl-1-(meth)acryloyloxycyclohexane, 1-ethyl-1-(meth)acryloyloxycyclohexane, 1-methyl-1-(meth)acryloyloxycycloheptane, 1-ethyl-1-(meth)acryloyloxycycloheptane, 1-methyl-1-(meth)acryloyloxycyclooctane, 1-ethyl-1-(meth)acryloyloxycyclooctane, 2-ethyl-2-(meth)acryloyloxydecahydro-1,4:5,8-dimethanonaphthalene, and 2-ethyl-2-(meth)acryloyloxynorbornane. Commercially available products can be used as these monomers.

Examples of the constituent unit other than the constituent unit represented by the formulas (Cl) and (C2) include a constituent unit derived from a monomer such as γ-butyrolactone (meth)acrylate, 2-hydroxystyrene, 3-hydroxystyrene, 4-hydroxystyrene, 3,5-diiodo-4-hydroxystyrene, or maleic acid anhydride. Commercially available products can be used as these monomers.

The iodine-containing (meth)acrylate (co)polymer represented by the formula (5) obtained by using the iodine-containing (meth)acrylate compound represented by the formula (2) as a constituent unit, the iodine-containing (meth)acrylate (co)polymer represented by the formula (6) obtained by using the iodine-containing (meth)acrylate compound represented by the formula (3) as a constituent unit, and the iodine-containing (meth)acrylate (co)polymer represented by the formula (6') obtained by using the iodine-containing (meth)acrylate compound represented by the formula (3') as a constituent unit can also be obtained by the same method. The (co)polymer represented by the formula (5), the (co)polymer represented by the formula (6), and the (co)polymer represented by the formula (6') are preferable for improving the performance of the material for film formation for lithography.

(5)

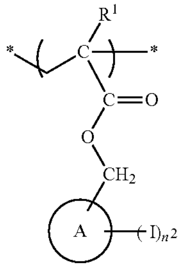

In the formula (5), $R^1$, $n^2$, and A are as defined in the above formula (1), and the symbol * is as defined in the above formula (4).

(6)

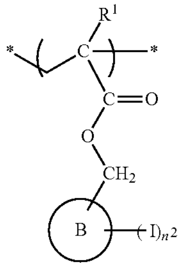

In the formula (6), $R^1$, $n^2$, and B are as defined in the above formula (3), and the symbol * is as defined in the above formula (4).

B contains at least one acyl group. The acyl group is as described above. Among them, an ethanoyl group (acetyl group) and a benzoyl group are preferable, and an ethanoyl group (acetyl group) is more preferable.

It is preferable that B contains at least one acyl group from the viewpoint of enhancing the stability of the (co)polymer. It is also preferable from the viewpoint of enhancing the productivity of the (co)polymer. When an acyl group is contained as a substituent in the compound serving as the skeleton of B, the stability of the compound and the (co) polymer is further enhanced, and the resin into which the compound and the (co)polymer are introduced is satisfactorily dissolved in an organic solvent and is more excellent in storage stability, and thus the number of acyl groups in the compound serving as the skeleton of B is preferably 1 to 8, more preferably 1 to 5, still more preferably 1 to 3, and further preferably 1.

In a practical aspect, the (co)polymer can also be used by hydrolyzing a part or all of the acyl groups contained in B to form hydroxy groups. By having a hydroxy group, it is possible to obtain a (co)polymer having more excellent alkali developability and achieving both film defect reduction and sensitivity. The (co)polymer may contain, together with the constituent unit represented by the formula (6), a constituent unit having a hydroxy group obtained by hydrolysis of a part or all of the acyl groups contained in B in the formula (6).

In view of achieving all of film defect reduction, sensitivity, and etching resistance, in the formula (6), B is preferably an aromatic group having 5 to 30 carbon atoms optionally having a substituent, and more preferably benzene optionally having a substituent. The aromatic group is as described above.

(6')

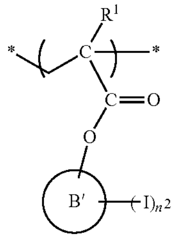

In the formula (6'), $R^1$, $n^2$, and B' are as defined in the above formula (3'), and the symbol * is as defined in the above formula (4).

B' contains at least one acyl group. The acyl group is as described above. Among them, an ethanoyl group (acetyl group) and a benzoyl group are preferable, and an ethanoyl group (acetyl group) is more preferable.

It is preferable that B' contains at least one acyl group from the viewpoint of enhancing the stability of the (co) polymer. It is also preferable from the viewpoint of enhancing the productivity of the (co)polymer. When an acyl group is contained as a substituent in the compound serving as the skeleton of B', the stability of the compound and the (co)polymer is further enhanced, and the resin into which the compound and the (co)polymer are introduced is satisfactorily dissolved in an organic solvent and is more excellent in storage stability, and thus the number of acyl groups in the compound serving as the skeleton of B' is preferably 1 to 10, more preferably 1 to 5, still more preferably 1 to 3, and further preferably 1.

In a practical aspect, the (co)polymer can also be used by hydrolyzing a part or all of the acyl groups contained in B' to form hydroxy groups. By having a hydroxy group, it is possible to obtain a (co)polymer having more excellent alkali developability and achieving both film defect reduction and sensitivity. The (co)polymer may contain, together with the constituent unit represented by the formula (6'), a constituent unit having a hydroxy group obtained by hydrolysis of a part or all of the acyl groups contained in B' in the formula (6').

In view of achieving all of film defect reduction, compound stability, sensitivity, and etching resistance, in the formula (6), B' is preferably an alicyclic ring having 5 to 30 carbon atoms optionally having a substituent, more preferably alicyclic hydrocarbon having 5 to 30 carbon atoms optionally having a substituent, and still more preferably adamantane optionally having a substituent. The alicyclic ring and alicyclic hydrocarbon are as described above.

<Method for Producing Iodine-Containing (Meth)Acrylate (Co) Polymer>

Next, a method for producing the (co)polymer of the present embodiment by polymerization reaction will be described.

The polymerization reaction is carried out by dissolving a monomer to be a constituent unit in a solvent, adding a catalyst, and heating or cooling. The reaction conditions can be arbitrarily set depending on the kind of the initiator, the initiation method such as heat and light, the temperature, the pressure, the concentration, the solvent, the additive, and the like. The (co)polymer can be produced by a publicly known method such as radical polymerization using a radical generating agent such as azoisobutyronitrile and peroxide, or ion polymerization using a catalyst such as alkyllithium and Grignard reagent.

As the solvent used in the polymerization reaction, commercially available products that are generally available can be used. Various solvents such as alcohols, ethers, hydrocarbons and halogen-based solvents can be appropriately used as such a solvent, within a range not inhibiting the reaction. The solvent may be used alone or as a mixture of a plurality of solvents as long as the reaction is not inhibited. Examples of the solvent include solvents described herein.

The (co)polymer obtained by the polymerization reaction can be purified by a publicly known method. Specifically, ultrafiltration, crystallization, microfiltration, acid washing, washing with water having an electric conductivity of 10 mS/m or less and extraction can be carried out in combination. By such a purification method, a desired high-purity (co)polymer can be obtained.

Further, for the purpose of removing metal-containing impurities such as metal ions and metal oxides contained in the obtained (co)polymer, a purification method for the purpose of removing metal impurities may be added. For the details of the purification method, reference can be made to the methods described herein, such as the above and Examples. In the obtained (co)polymer, the content of various metals (for example, Na, K, Ca, Mg, Fe, Cu, Ni, Sn, Ag, Mo, Mn, Zn, Co, Al, Pb, Cr, and Ti) in the (co)polymer is usually 10 ppb or less, preferably 5 ppb or less, and more preferably 1 ppb or less.

[Composition Containing Iodine-Containing (Meth)Acrylate Compound and/or Iodine-Containing (Meth)Acrylate (Co)Polymer]

The composition of the present embodiment (also simply referred to as "composition") includes the iodine-containing (meth)acrylate compound of the present embodiment and/or the iodine-containing (meth)acrylate (co)polymer of the present embodiment. The composition is suitable for lithographic techniques. The composition can be used for film formation purposes for lithography, for example, resist film formation purposes (that is, a "resist composition"). The composition can be used for upper layer film formation purposes (that is, a "composition for upper layer film formation"), intermediate layer formation purposes (that is, a "composition for intermediate layer formation"), underlayer film formation purposes (that is, a "composition for underlayer film formation"), and the like. According to the composition of the present embodiment, not only a film having high sensitivity can be formed, but also the composition can also impart a good shape to a resist pattern with high resolution.

The composition can also be used as an optical component forming composition applying lithography technology. The optical component is used in the form of a film or a sheet. Examples of such an optical component include a plastic lens (a prism lens, a lenticular lens, a microlens, a Fresnel lens, a viewing angle control lens, a contrast improving lens, etc.), a phase difference film, a film for electromagnetic wave shielding, a prism, an optical fiber, a solder resist for flexible printed wiring, a plating resist, an interlayer insulating film for multilayer printed circuit boards, a photosensitive optical waveguide, a liquid crystal display, an organic electroluminescent (EL) display, an optical semiconductor (LED) element, a solid state image sensing element, an organic thin film solar cell, a dye sensitized solar cell, and an organic thin film transistor (TFT). The composition can be particularly suitably utilized as an embedded film and a smoothed film on a photodiode, a smoothed film in front of or behind a color filter, a microlens, and a smoothed film and a conformal film on a microlens, all of which are components of a solid state image sensing element, to which high refractive index is demanded.

The composition may also contain other components such as a base material, a solvent, an acid generating agent, an acid diffusion controlling agent, and a base generating agent, as needed. These components can be used alone or in combination of two or more thereof, as needed. Hereinafter, each of these components will be described.

<Base Material>

The composition may contain a base material.

The "base material" in the present embodiment is a compound (including a resin) other than the iodine-containing (meth)acrylate compound of the present embodiment and an iodine-containing (meth)acrylate (co)polymer of the present embodiment, and means a base material applied as a resist for g-ray, i-ray, KrF excimer laser (248 nm), ArF excimer laser (193 nm), extreme ultraviolet (EUV) lithography (13.5 nm) or electron beam (EB) (for example, a base material for lithography or a base material for resist). These base materials can be used as the base material according to the present embodiment without particular limitation. Examples of the base material include a phenol novolac resin, a cresol novolac resin, a hydroxystyrene resin, a (meth)acrylic resin, a hydroxystyrene-(meth)acrylic copolymer, a cycloolefin-maleic anhydride copolymer, a cycloolefin, and a vinyl ether-maleic anhydride copolymer; an inorganic resist material having a metallic element such as titanium, tin, hafnium and zirconium; and a derivative thereof. Among them, from the viewpoint of obtaining a finer resist pattern, preferable are a phenol novolac resin, a cresol novolac resin, a hydroxystyrene resin, a (meth)acrylic resin, a hydroxystyrene-(meth)acrylic copolymer; an inorganic resist material having a metallic element such as titanium, tin, hafnium and zirconium; and a derivative thereof. These base materials are used alone or in combination of two or more thereof.

Examples of the derivative include those to which a dissociation group is introduced and those to which a crosslinkable group is introduced. The derivative to which a dissociation group or a crosslinkable group is introduced can exhibit dissociation reaction or crosslinking reaction through the effect of light, acid or the like.

The "dissociation group" refers to a characteristic group such as an alkali soluble group that is cleaved to generate a functional group that alters solubility. Examples of the alkali-soluble group include a phenolic hydroxy group, a carboxyl group, a sulfonic acid group, and a hexafluoroisopropanol group, and a phenolic hydroxy group and a carboxyl group are preferable, and a phenolic hydroxy group is more preferable.

The "crosslinkable group" refers to a group that crosslinks in the presence of a catalyst or without a catalyst. Examples of the crosslinkable group include an alkoxy group having 1 to 20 carbon atoms, a group having an allyl group, a group having a (meth)acryloyl group, a group having an epoxy (meth)acryloyl group, a group having a hydroxy group, a group having a urethane (meth)acryloyl group, a group having a glycidyl group, and a group having a vinyl phenylmethyl group.

<Solvent>

The composition may contain a solvent.

As the solvent, publicly known solvents can be arbitrarily used as long as it can at least dissolve the iodine-containing (meth)acrylate compound of the present embodiment and/or the iodine-containing (meth)acrylate (co)polymer of the present embodiment. Specific examples of the solvent include an ethylene glycol monoalkyl ether acetate such as ethylene glycol monomethyl ether acetate, ethylene glycol monoethyl ether acetate, ethylene glycol mono-n-propyl ether acetate, and ethylene glycol mono-n-butyl ether acetate; an ethylene glycol monoalkyl ether such as ethylene glycol monomethyl ether and ethylene glycol monoethyl ether; a propylene glycol monoalkyl ether acetate such as propylene glycol monomethyl ether acetate (PGMEA), propylene glycol monoethyl ether acetate, propylene glycol mono-n-propyl ether acetate, and propylene glycol mono-n-butyl ether acetate; a propylene glycol monoalkyl ethers such as propylene glycol monomethyl ether (PGME) and propylene glycol monoethyl ether; a lactate ester such as methyl lactate, ethyl lactate, n-propyl lactate, n-butyl lactate, and n-amyl lactate; an aliphatic carboxylic acid ester such as methyl acetate, ethyl acetate, n-propyl acetate, n-butyl acetate, n-amyl acetate, n-hexyl acetate, methyl propionate, and ethyl propionate; another ester such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutyl acetate, 3-methyl-3-methoxybutyl acetate, butyl 3-methoxy-3-methylpropionate, butyl 3-methoxy-3-methylbutyrate, methyl acetoacetate, methyl pyruvate, and ethyl pyruvate; an aromatic hydrocarbon such as toluene and xylene; a ketone such as acetone, 2-butanone, 2-heptanone, 3-heptanone, 4-heptanone, cyclopentanone (CPN), anisole, and cyclohexanone (CHN); an amide such as N,N-dimethylformamide, N-methylacetamide, N,N-dimethylacetamide, and N-methylpyrrolidone; a lactone such as γ-lactone; and a furan such as tetrahydrofuran. The solvent used in the present embodiment is preferably a safe solvent, more preferably at least one selected from PGMEA, PGME, CHN, CPN, 2-heptanone, anisole, n-butyl acetate and ethyl lactate, and still more preferably at least one selected from PGMEA, PGME, CHN, CPN and ethyl lactate. These solvents are used alone or in combination of two or more thereof.

In the present embodiment, the amount of the solid components and the amount of the solvent are not particularly limited, but preferably the solid components are 1 to 80% by mass and the solvent is 20 to 99% by mass, more preferably the solid components are 1 to 50% by mass and the solvent is 50 to 99% by mass, still more preferably the solid components are 2 to 40% by mass and the solvent is 60 to 98% by mass, and still further preferably the solid components are 2 to 10% by mass and the solvent is 90 to 98% by mass, based on the total amount (100% by mass) of the solid components and the solvent.

<Acid Generating Agent>

The composition may contain an acid generating agent.

The composition preferably contains one or more acid generating agents generating an acid directly or indirectly by irradiation of any radiation selected from visible light, ultraviolet, excimer laser, electron beam, extreme ultraviolet (EUV), X-ray and ion beam. For example, an acid generating agent described in International Publication No. WO 2013/024778 can be used. The acid generating agent is used alone or in combination of two or more thereof.

The amount of the acid generating agent to be used is preferably 0.001 to 49% by mass, more preferably 1 to 40% by mass, still more preferably 3 to 30% by mass, and further preferably 10 to 25% by mass, based on the total mass (100% by mass) of solid components. By using the acid generating agent within the above range, there is a tendency that a pattern profile with high sensitivity and low edge roughness is obtained. In the present embodiment, the acid generation method is not particularly limited as long as an acid is generated in the system. By using excimer laser instead of ultraviolet such as g-ray and i-ray, finer processing is possible, and also by using electron beam, extreme ultraviolet, X-ray or ion beam as a high energy ray, further finer processing is possible.

Examples of the acid generating agent include the compounds disclosed in International Publication No. WO 2017/033943. The acid generating agent is preferably an acid generating agent having an aromatic ring, more preferably an acid generating agent having a sulfonate ion having an aryl group, and still more preferably diphenyltrimethylphenylsulfonium p-toluenesulfonate, triphenylsulfonium p-toluenesulfonate, triphenylsulfonium trifluoromethanesulfonate, or triphenylsulfonium nonafluoromethanesulfonate. By using such an acid generating agent, line edge roughness can be reduced.

<Base Generating Agent>

The composition may contain a base generating agent.

The case where the base generating agent is a photobase generating agent will be described.

In the present embodiment, the photobase generating agent refers to a base generating agent that generates a base upon exposure and does not exhibit activity under normal conditions at normal temperature and pressure, but generates a base (basic substance) upon irradiation with an electromagnetic wave and heating as an external stimulus.

As the photobase generating agent, publicly known photobase generating agents can be used, and examples thereof include, for example, a carbamate derivative, an amide derivative, an imide derivative, an α-cobalt complex, an imidazole derivative, a cinnamic acid amide derivative, and an oxime derivative.

Examples of the basic substance generated from the photobase generating agent include, but not particularly limited to, a compound having an amino group. Examples of such a compound include monoamines, polyamines such as diamines, and amidines.

The basic substance to be generated is preferably a compound having an amino group with a higher basicity (a higher pKa value of the conjugate acid) from the viewpoint of sensitivity and resolution.

Examples of the photobase generating agent include, for example, base generating agents having a cinnamic amide structure as disclosed in Japanese Patent Laid-Open No. 2009/80452 and International Publication NO. WO 2009/123122; base generating agents having a carbamate structure as disclosed in Japanese Patent Laid-Open No. 2006/189591 and Japanese Patent Laid-Open No. 2008/247747; base generating agents having an oxime structure or a carbamoyloxime structure as disclosed in Japanese Patent Laid-Open No. 2007/249013 and Japanese Patent Laid-Open No. 2008/003581; and compounds described in Japanese Patent Laid-Open No. 2010/243773. Other structures of publicly known base generating agents can also be used.

The photobase generating agent can be used alone or in combination of two or more thereof.

The preferred content of the photobase generating agent in actinic ray or radiation sensitive resin composition is similar to the preferred content of the above photoacid generating agent in actinic ray or radiation sensitive resin composition.

<Acid Diffusion Controlling Agent>

The composition may contain an acid diffusion controlling agent.

In the present embodiment, the composition may contain an acid diffusion controlling agent having a function of controlling diffusion of an acid generated from an acid generating agent by radiation irradiation in a resist film to inhibit any unpreferable chemical reaction in an unexposed region or the like. By using the acid diffusion controlling agent, there is a tendency that the storage stability of the composition can be improved. Also, by using the acid diffusion controlling agent, there is a tendency that not only the resolution of a film formed by using the composition of the present embodiment can be improved, but the line width change of a resist pattern due to variation in the post exposure delay time before radiation irradiation and the post exposure delay time after radiation irradiation can also be inhibited, making the composition excellent in process stability. Examples of the acid diffusion controlling agent include, a radiation degradable basic compound such as a nitrogen atom-containing basic compound such as tributylamine, a basic sulfonium compound, and a basic iodonium compound.

For example, an acid diffusion controlling agent described in International Publication No. WO 2013/024778 can be used. The acid diffusion controlling agent is used alone or in combination of two or more thereof.

The content of the acid diffusion controlling agent is preferably 0.001 to 49% by mass, more preferably 0.01 to 10% by mass, still more preferably 0.01 to 5% by mass, and further preferably 0.01 to 3% by mass, based on the total mass (100% by mass) of solid components. When the content of the acid diffusion controlling agent is within the above range, there is a tendency that a decrease in resolution, and deterioration of the pattern shape and the dimension fidelity or the like can be prevented. Moreover, even though the post exposure delay time from electron beam irradiation to heating after radiation irradiation becomes longer, the shape of the pattern upper layer portion can be prevented from being deteriorated. Also, when the content is 10% by mass or less, there is a tendency that a decrease in sensitivity, and developability of the unexposed portion or the like can be prevented. By using an acid diffusion controlling agent, there is a tendency that the storage stability of a composition is improved, along with improvement of the resolution, the line width change of a resist pattern due to variation in the post exposure delay time before radiation irradiation and the post exposure delay time after radiation irradiation can be inhibited, making the composition excellent in process stability.

<Further Component>

To the composition of the present embodiment, if required, as the further component, one kind or two kinds or more of various additive agents such as a crosslinking agent, a dissolution promoting agent, a dissolution controlling agent, a sensitizing agent, a surfactant, and an organic carboxylic acid or an oxo acid of phosphor or derivative thereof can be added.

(Crosslinking Agent)

The composition may include one or more crosslinking agents. The crosslinking agent means a compound capable of crosslinking at least one of a base material, the iodine-containing (meth)acrylate compound, and iodine-containing (meth)acrylate (co)polymer. It is preferable that the crosslinking agent be an acid crosslinking agent capable of intramolecularly or intermolecularly crosslinking the base material in the presence of the acid generated from the acid generating agent. Examples of such an acid crosslinking agent include a compound having one or more groups capable of crosslinking the base material (hereinafter, referred to as a "crosslinkable group").

Examples of the crosslinkable group include: (i) a hydroxyalkyl group or a group derived therefrom, such as a hydroxy (alkyl group having 1 to 6 carbon atoms), alkoxy having 1 to 6 carbon atoms (alkyl group having 1 to 6 carbon atoms) and acetoxy (alkyl group having 1 to 6 carbon atoms); (ii) a carbonyl group or a group derived therefrom, such as a formyl group and a carboxy (alkyl group having 1 to 6 carbon atoms); (iii) a nitrogenous group containing group such as a dimethylaminomethyl group, a diethylaminomethyl group, a dimethylolaminomethyl group, a diethylolaminomethyl group and a morpholinomethyl group; (iv) a glycidyl group containing group such as a glycidyl ether group, a glycidyl ester group and a glycidylamino group; (v) a group derived from an aromatic group such as an allyloxy having 1 to 6 carbon atoms (alkyl group having 1 to 6 carbon atoms) and an aralkyloxy having 1 to 6 carbon atoms (alkyl group having 1 to 6 carbon atoms) such as a benzyloxymethyl group and a benzoyloxymethyl group; and (vi) a polymerizable multiple bond containing group such as a vinyl group and an isopropenyl group. As the crosslinkable group of the crosslinking agent, a hydroxyalkyl group and an alkoxyalkyl group or the like are preferable, and an alkoxymethyl group is more preferable.

As the crosslinking agent having a crosslinkable group, for example, an acid crosslinking agent described in International Publication No. WO 2013/024778 can be used. The crosslinking agent is used alone or in combination of two or more thereof.

The content of the crosslinking agent is preferably 50% by mass or less, more preferably 40% by mass or less, still more preferably 30% by mass or less, and further preferably 20% by mass or less, based on the total mass (100% by mass) of the solid component.

(Dissolution Promoting Agent)

The dissolution promoting agent is a component having a function of, when the solubility of a solid component is too low, increasing the solubility of the solid component in a developer to moderately increase the dissolution rate of the compound upon developing. As the dissolution promoting agent, those having a low molecular weight are preferable, and examples thereof include a phenolic compound having a low molecular weight. Examples of the phenolic compound having a low molecular weight include a bisphenol and a tris (hydroxyphenyl)methane. These dissolution promoting agents are used alone or in combination of two or more thereof.

The content of the dissolution promoting agent, which is arbitrarily adjusted according to the kind of the above solid component to be used, is preferably 0 to 49% by mass, more preferably 0 to 5% by mass, still more preferably 0 to 1% by mass, and further preferably 0% by mass, based on the total mass (100% by mass) of the solid component.

(Dissolution Controlling Agent)

The dissolution controlling agent is a component having a function of, when the solubility of a solid component is too high, controlling the solubility of the solid component in a developer to moderately decrease the dissolution rate upon developing. As such a dissolution controlling agent, the one which does not chemically change in steps such as calcination of resist coating, radiation irradiation, and development is preferable.

Examples of the dissolution controlling agent include aromatic hydrocarbons such as phenanthrene, anthracene, and acenaphthene; ketones such as acetophenone, benzophenone, and phenyl naphtyl ketone; and sulfones such as methyl phenyl sulfone, diphenyl sulfone, and dinaphthyl sulfone. These dissolution controlling agents are used alone or in combination of two or more thereof.

The content of the dissolution controlling agent, which is arbitrarily adjusted according to the kind of the above compound to be used, is preferably 0 to 49% by mass, more preferably 0 to 5% by mass, still more preferably 0 to 1% by mass, and further preferably 0% by mass, based on the total mass (100% by mass) of the solid component.

(Sensitizing Agent)

The sensitizing agent is a component having a function of absorbing irradiated radiation energy, transmitting the energy to the acid generating agent, and thereby increasing the acid production amount, and improving the apparent sensitivity of a resist. Examples of such a sensitizing agent include benzophenones, biacetyls, pyrenes, phenothiazines, and fluorenes. These sensitizing agents are used alone or in combination of two or more thereof.

The content of the sensitizing agent, which is arbitrarily adjusted according to the kind of the above compound to be used, is preferably 0 to 49% by mass, more preferably 0 to 5% by mass, still more preferably 0 to 1% by mass, and further preferably 0% by mass, based on the total mass (100% by mass) of the solid component.

(Surfactant)

The surfactant is a component having a function of improving coatability and striation of the composition, and developability of a resist or the like. The surfactant may be any of anionic, cationic, nonionic, and amphoteric surfactants. Preferable examples of the surfactant include a nonionic surfactant. The nonionic surfactant has a good affinity with a solvent to be used in production of the composition, and can further enhance the effects of the composition. Examples of the nonionic surfactant include a polyoxyethylene higher alkyl ether, a polyoxyethylene higher alkyl phenyl ether, and a higher fatty acid diester of polyethylene glycol. Commercially available products may be used as these surfactants, and examples thereof include, hereinafter by trade name, EFTOP® (manufactured by Jemco Inc.), MEGAFAC® (manufactured by DIC Corporation), Fluorad (manufactured by Sumitomo 3M Limited), AsahiGuard®, Surflon® (hereinbefore, manufactured by Asahi Glass Co., Ltd.), Pepole® (manufactured by Toho Chemical Industry Co., Ltd.), KP (manufactured by Shin-Etsu Chemical Co., Ltd.), and Polyflow (manufactured by Kyoeisha Chemical Co., Ltd.). These surfactants are used alone or in combination of two or more thereof.

The content of the surfactant, which is arbitrarily adjusted according to the kind of the above solid component to be used, is preferably 0 to 49% by mass, more preferably 0 to 5% by mass, still more preferably 0 to 1% by mass, and further preferably 0% by mass based on the total mass (100% by mass) of solid components.

(Organic Carboxylic Acid or Oxo Acid of Phosphor or Derivative Thereof)

For the purpose of prevention of sensitivity deterioration or improvement of a resist pattern shape and post exposure delay stability or the like, and as an optional component, the composition can contain an organic carboxylic acid or an oxo acid of phosphor or derivative thereof. The organic carboxylic acid or the oxo acid of phosphor or derivative thereof can be used in combination with the acid diffusion controlling agent, or may be used alone. Suitable examples of the organic carboxylic acid include malonic acid, citric acid, malic acid, succinic acid, benzoic acid and salicylic acid. Examples of the oxo acid of phosphor or derivative thereof include phosphoric acid or derivative thereof such as ester including phosphoric acid, di-n-butyl phosphate and diphenyl phosphate; phosphonic acid or derivative thereof such as ester including phosphonic acid, dimethyl phosphonate, di-n-butyl phosphonate, phenylphosphonic acid, diphenyl phosphonate and dibenzyl phosphonate; and phosphinic acid and derivative thereof such as ester including phosphinic acid and phenylphosphinic acid. Among them, phosphonic acid is more preferable.

The organic carboxylic acid or the oxo acid of phosphor or derivative thereof can be used alone or in combination of two or more thereof. The content of the organic carboxylic acid or the oxo acid of phosphor or derivative thereof, which is arbitrarily adjusted according to the kind of the above compound to be used, is preferably 0 to 49% by mass, more preferably 0 to 5% by mass, still more preferably 0 to 1% by mass, and further preferably 0% by mass, based on the total mass (100% by mass) of the solid component.

<Further Additive Agent>

The composition of the present embodiment can contain one kind or two kinds or more of additive agents other than the above components, if required. Examples of such an additive agent include a dye, a pigment and an adhesion aid. For example, when the composition contains a dye or a pigment, a latent image of the exposed portion is visualized and influence of halation upon exposure can be alleviated, which is preferable. Also, when the composition contains an adhesion aid, adhesiveness to a substrate can be improved, which is preferable. Examples of the other additive agents include a halation preventing agent, a storage stabilizing agent, a defoaming agent, and a shape improving agent. Specific examples include 4-hydroxy-4'-methylchalcone. These additive agents are used alone or in combination of two or more thereof.

In the composition of the present embodiment, the total content of the additive agent (optional component) can be 0 to 99% by mass of the total mass (100% by mass) of the solid component, and is preferably 0 to 49% by mass, more preferably 0 to 10% by mass, still more preferably 0 to 5% by mass, further preferably 0 to 1% by mass, and particularly preferably 0% by mass.

[Resist Pattern Formation Method]

A method of forming a resist pattern of the present embodiment includes the steps of, in this order, forming a film using the composition of the present embodiment, exposing the formed film, and removing an exposed portion of the exposed film using a developer to form a pattern.

In order to form a resist pattern from the composition of the present invention, the composition solution is applied to a substrate such as a silicon wafer, a metal, a plastic, a glass or a ceramic by an appropriate application means such as a spin coater, a dip coater or a roller coater to form a resist film, and in some cases, heat treatment is carried out at a temperature of about 50° C. to 200° C. for a predetermined time (usually 15 to 600 seconds) before exposure through a predetermined mask pattern. The thickness of the coating film after exposure is, for example, about 0.01 to 20 μm, preferably about 0.05 to 10 μm, and more preferably about 0.07 to 2 μm. For exposure, rays of various wavelengths such as ultraviolet rays, far ultraviolet rays, electron beams, extreme ultraviolet rays, and X-rays can be used. For example, far ultraviolet rays such as F2 excimer laser (wavelength: 157 nm), ArF excimer laser (wavelength: 193 nm) and KrF excimer laser (wavelength: 248 nm); extreme ultraviolet rays (wavelength: 13 nm); X-rays; and electron beams can be arbitrarily selected and used as light sources.

The exposure conditions such as the amount of exposure are arbitrarily selected in accordance with the compound, the (co)polymer, the blending composition of the composition containing these, and the type of each additive.

In the present embodiment, in order to stably form a fine pattern with a high degree of accuracy, it is preferable to perform a heat treatment at a temperature of 50 to 200° C. for 30 seconds or longer after exposure. In this case, when the temperature is less than 50° C., variations in the sensitivity is likely to spread depending on the type of the substrate. Thereafter, a predetermined resist pattern is formed by developing with an alkaline developer, typically at 10 to 50° C. for 10 to 200 seconds, and preferably at 20 to 25° C. for 15 to 90 seconds.

As the alkaline developer, for example, an alkaline aqueous solution obtained by dissolving an alkaline compound such as an alkali metal hydroxide, an aqueous ammonia, an alkylamine, an alkanolamine, a heterocyclic amine, a tetraalkylammonium hydroxide such as tetramethylammonium hydroxide, choline, 1,8-diazabicyclo-[5.4.0]-7-undecene, and 1,5-diazabicyclo-[4.3.0]-5-nonene at a concentration of 1 to 10% by weight, preferably 1 to 3% by weight, is used. These alkali developers are used alone or in combination of two or more thereof. Further, a water-soluble organic solvent or a surfactant may be appropriately added to the developer containing the alkaline aqueous solution.

In the present embodiment, in order to stably form a fine pattern with a high degree of accuracy, it is also possible to form a resist pattern by performing a developing process with a developer containing an organic solvent as a main component after exposure and PEB.

Various organic solvents are widely used as organic solvents used for the developer. Examples of such a solvent include an ester-based solvent, a ketone-based solvent, an alcohol-based solvent, an amide-based solvent, an ether-based solvent, and a hydrocarbon-based solvent. These organic solvents are used alone or in combination of two or more thereof.

The developer preferably contains a ketone-based solvent, an ester-based solvent, an alcohol-based solvent, and an ether-based solvent.

Examples of the ester-based solvent include, for example, methyl acetate, ethyl acetate, butyl acetate, isobutyl acetate, pentyl acetate, propyl acetate, isopropyl acetate, amyl acetate (pentyl acetate), isoamyl acetate (isopentyl acetate, 3-methylbutyl acetate), 2-methylbutyl acetate, 1-methylbutyl acetate, hexyl acetate, isohexyl acetate, heptyl acetate, octyl acetate, ethyl methoxy acetate, ethyl ethoxy acetate, propylene glycol monomethyl ether acetate (PGMEA; otherwise known as 1-methoxy-2-acetoxypropane), ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3 methoxypentyl acetate, 3-methyl-4-methoxypentyl acetate, 4-methyl-4 methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl hydroxyisobutyrate, methyl propionate, ethyl propionate, propyl propionate, isopropyl propionate, butyl propionate, isobutyl propionate, pentyl propionate, hexyl propionate, heptyl propionate, butyl butanoate, isobutyl butanoate, pentyl butanoate, hexyl butanoate, isobutyl isobutanoate, propyl pentanoate, isopropyl pentanoate, butyl pentanoate, pentyl pentanoate, ethyl hexanoate, propyl hexanoate, butyl hexanoate, isobutyl hexanoate, methyl heptanoate, ethyl heptanoate, propyl heptanoate, cyclohexyl acetate, cycloheptyl acetate, 2-ethylhexyl acetate, cyclopentyl propionate, methyl 2-hydroxypropionate, ethyl 2-hydroxypropionate, methyl-3-methoxypropionate, ethyl-3-methoxypropionate, ethyl-3-ethoxypropionate, and propyl-3-ethoxypropionate. Among these, butyl acetate, amyl acetate, isoamyl acetate, 2-methylbutyl acetate, 1-methylbutyl acetate, hexyl acetate, pentyl propionate, hexyl propionate, heptyl propionate, methyl hydroxyisobutyrate, and butyl butanoate are preferable, and butyl acetate, isoamyl acetate, and methyl hydroxyisobutyrate are more preferable.

Examples of the ketone-based solvent include, for example, 1-octanone, 2-octanone, 1-nonanone, 2-nonanone, acetone, 2-heptanone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, propylene carbonate, and γ-butyrolactone. Among them, 2-heptanone is preferred.

Examples of the alcohol-based solvent include, for example, alcohols such as methanol, ethanol, 1-propanol, isopropanol, 1-butanol, 2-butanol, 3-methyl-1-butanol, tert-butyl alcohol, 1-pentanol, 2-pentanol, 1-hexanol, 1-heptanol, 1-octanol, 1-decanol, 2-hexanol, 2-heptanol, 2-octanol, 3-hexanol, 3-heptanol, 3-octanol, 4-octanol, 3-methyl-3-pentanol, cyclopentanol, 2,3-dimethyl-2-butanol, 3,3-dimethyl-2-butanol, 2-methyl-2-pentanol, 2-methyl-3-pentanol, 3-methyl-2-pentanol, 3-methyl-3-pentanol, 4-methyl-2-pentanol, 4-methyl-3-pentanol, cyclohexanol, 5-methyl-2-hexanol, 4-methyl-2-hexanol, 4,5-dithyl-2hexal, 6-methyl-2-heptanol, 7-methyl-2-octanol, 8-methyl-2-nonal, 9-methyl-2-decanol, and 3-methoxy-1-butanol (monohydric alcohol); glycol-based solvents such as ethylene glycol, diethylene glycol, and triethylene glycol; glycol ether-based solvents containing hydroxy groups such as ethylene glycol monomethyl ether, propylene glycol monomethyl ether (PGME; otherwise known as 1-methoxy-2-propanol), diethylene glycol monomethyl ether, triethylene glycol monoethyl ether, methoxymethyl butanol, ethylene glycol monoethyl ether, ethylene glycol monopropyl ether, ethylene glycol monobutyl ether, propylene glycol monoethyl ether, propylene glycol monopropyl ether, propylene glycol monobutyl ether, and propylene glycol monophenyl ether; and the like. Among these, a glycol ether-based solvent is preferably used.

Examples of the ether-based solvent include, for example, in addition to the glycol ether-based solvent containing hydroxy groups, glycol ether-based solvents not containing hydroxy groups such as propylene glycol dimethyl ether, propylene glycol diethyl ether, diethylene glycol dimethyl ether, and diethylene glycol diethyl ether; aromatic ether solvents such as anisole and phenetol; dioxane, tetrahydrofuran, tetrahydropyran, perfluoro-2-butyltetrahydrofuran, perfluorotetrahydrofuran, 1,4-dioxane, and isopropyl ether. Among these, glycol ether-based solvents not containing a hydroxy group and aromatic ether-based solvents such as anisole are preferable.

Examples of the amide-based solvent include N-methyl-2-pyrrolidone, N,N-dimethylacetamide, N,N-dimethylformamide, phosphoric hexamethyltriamide, and 1,3-dimethyl-2-imidazolidinone.

Examples of the hydrocarbon-based solvent include aliphatic hydrocarbon-based solvents such as pentane, hexane, octane, nonane, decane, dodecane, undecane, hexadecane, 2,2,4-trimethylpentane, 2,2,3-trimethylhexane, perfluorohexane, and perfluoroheptane; and aromatic hydrocarbon-based solvents such as toluene, xylene, ethylbenzene, propylbenzene, 1-methylpropylbenzene, 2-methylpropylbenzene, dimethylbenzene, diethylbenzene, ethylmethylbenzene, trimethylbenzene, ethyldimethylbenzene, and dipropylbenzene.

An unsaturated hydrocarbon-based solvent can also be used as the hydrocarbon-based solvent. Examples of such a solvent include unsaturated hydrocarbon-based solvents such as octene, nonene, decene, undecene, dodecene, and hexadecene. The number of double bonds or triple bonds of the unsaturated hydrocarbon-based solvent is not particularly limited, and the unsaturated hydrocarbon solvent may have a double bond or a triple bond at any position of the hydrocarbon chain. When the unsaturated hydrocarbon-based solvent has a double bond, a cis isomer and a trans isomer may be mixed.

The aliphatic hydrocarbon-based solvent which is a hydrocarbon-based solvent may be a mixture of compounds having the same carbon number but different structures. For example, when decane is used as the aliphatic hydrocarbon-based solvent, 2-methylnonane, 2,2-dimethyloctane, 4-ethyloctane, isooctane and the like which are compounds having the same number of carbon atoms and different structures may be contained in the aliphatic hydrocarbon-based solvent.

Further, only one kind of compounds having the same carbon number and different structures may be contained, or a plurality of kinds may be contained as described above.

Further, a publicly known basic compound, a publicly known water-soluble organic solvent, or a publicly known surfactant may be appropriately added to the developer containing the organic solvent.

[Method for Producing (Co)Polymer Having Hydroxy Group Represented by Formula (Y)]

In a practical aspect, the (co)polymer of the present embodiment can be made into a (co)polymer having a hydroxy group represented by the formula (Y) to form hydroxy groups by hydrolyzing a part or all of the acyl groups. Such a (co)polymer is obtained by hydrolyzing the acyl group in the iodine-containing (meth)acrylate (co) polymer of the present embodiment. Since the stability of the compound is high, the (co)polymer containing the compound as a constituent unit also has high stability, and by using such a (co)polymer, a (co)polymer having a hydroxy group useful for a resist material can be efficiently and stably produced.

(Y)

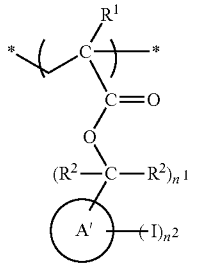

In the formula (Y), $R^1$, $R^2$, A', $n^1$, and $n^2$ are as described above, and the symbol * represents a bonding site to an adjacent constituent unit.

The hydrolysis can be carried out by a publicly known method, such as hydrolysis with an acid, hydrolysis with a base, and the like.

Examples of suitable acid catalysts include an inorganic acid such as hydrochloric acid, sulfuric acid, phosphoric acid, hydrobromic acid, and hydrofluoric acid; an organic acid such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; a Lewis acid such as zinc chloride, aluminum chloride, iron chloride, and boron trifluoride; and a solid acid such as tungstosilicic acid, tungstophosphoric acid, silicomolybdic acid, and phosphomolybdic acid.

Examples of suitable base catalysts include amine-containing catalysts such as pyridine and ethylenediamine; and non-amine basic catalysts such as metal salts. The metal salt is preferably a potassium salt or an acetate salt. Examples of such a catalyst include potassium acetate, potassium carbonate, potassium hydroxide, sodium acetate, sodium carbonate, sodium hydroxide, and magnesium oxide.

Non-amine base catalysts are commercially available, for example, from EM Science and Aldrich.

These catalysts are used alone or in combination of two or more thereof.

The amount of the catalyst to be used can be appropriately set according to the substrate to be used, the catalyst, the reaction conditions, or the like, and is not particularly limited, but in general, is suitably 1 to 5000 parts by mass, and is preferably 50 to 3000 parts by mass based on 100 parts by mass of the reaction raw materials from the viewpoint of the yield.

This reaction may be carried out in an organic solvent. As the organic solvent, a wide variety of organic solvents are used, including polar aprotic organic solvents and protic polar organic solvents. A single protic polar solvent and a single polar aprotic solvent can be used. Furthermore, it is possible to use mixtures of polar aprotic solvents, mixtures of protic polar solvents, mixtures of polar aprotic solvents with protic polar solvents and mixtures of aprotic or protic solvents with nonpolar solvents, and polar aprotic solvents or mixtures thereof are preferred. The solvent is effective but not an essential component. Examples of suitable polar aprotic solvents include, for example, alcohol-based solvents such as methanol and ethanol; ether-based solvents such as diethyl ether, tetrahydrofuran, dimethoxyethane, diglyme, and triglyme; ester-based solvents such as ethyl acetate and γ-butyrolactone; nitrile solvents such as acetonitrile; hydrocarbon-based solvents such as toluene and hexane; amide-based solvents such as N,N-dimethylformamide, 1-methyl-2-pyrrolidinone, N,N-dimethylacetamide, hexamethylphosphoramide, and hexamethylphosphorous triamide; and dimethyl sulfoxide. Among them, tetrahydrofuran and dimethyl sulfoxide are preferable. Examples of suitable protic polar solvents include di(propylene glycol) methyl ether, di(ethylene glycol)methyl ether, 2-butoxyethanol, ethylene glycol, 2-methoxyethanol, propylene glycol methyl ether, n-hexanol, and n-butanol.

The amount of the solvent to be used can be appropriately set according to the substrate to be used, the catalyst, the reaction conditions, or the like, and is not particularly limited, but in general, is suitably 0 to 10000 parts by mass, and is preferably 100 to 2000 parts by mass based on 100 parts by mass of the reaction raw materials from the viewpoint of the yield.

In the reaction, an iodine-containing (meth)acrylate (co) polymer, a catalyst, and optionally an organic solvent are added to a reactor to form a reaction mixture. Any suitable reactor may be used for the reaction. The reaction can be carried out by appropriately selecting a publicly known method such as a batch system, a semi-batch system, or a continuous system.

The reaction temperature depends on the concentration of the substrate, the stability of the product formed, the choice of catalyst and the desired yield and is not particularly limited. In general, a temperature of 0 to 200° C. is suitable, and from the viewpoint of yield, a temperature of 0 to 100° C. is preferable.

The reaction pressure depends on the concentration of the substrate, the stability of the product formed, the choice of catalyst and the desired yield and is not particularly limited. The pressure can be adjusted using an inert gas such as nitrogen or using an intake pump or the like. Conventional pressure reactors, including shaker vessels, rocker vessels, and agitated autoclaves, are used for high-pressure reactions.

The reaction time depends on the concentration of the substrate, the stability of the product formed, the choice of catalyst and the desired yield and is not particularly limited. Usually, most of the reaction is carried out in less than 12 hours, and the reaction time is generally 15 to 600 minutes.

Isolation and purification can be carried out after completion of the reaction using any suitable method publicly known in the art. For example, the reaction mixture is poured onto ice water and extracted into an organic solvent such as ethyl acetate, butyl acetate, and diethyl ether. The product is then recovered by removing the solvent using evaporation at reduced pressure. The monomer can be isolated and purified with a desired high-purity by a purification method well known in the art such as a separation and purification method using filtration, concentration, distillation, extraction, crystallization, recrystallization, column chromatography, activated carbon, or the like, or a method using a combination thereof. Further, for the purpose of removing metal-containing impurities such as metal ions and metal oxides contained in the obtained high-purity monomer, a purification method for the purpose of removing metal impurities may be added. For the details of the purification method, reference can be made to the methods described herein, such as the above and Examples. In the obtained high-purity monomer, the content of various metals (for example, Na, K, Ca, Mg, Fe, Cu, Ni, Sn, Ag, Mo, Mn, Zn, Co, Al, Pb, Cr, and Ti) in the compound is usually 10 ppb or less, preferably 5 ppb or less, and more preferably 1 ppb or less.

EXAMPLES

Hereinafter, the present embodiment will be described in further detail with reference to Examples and Comparative Examples, but the present embodiment is not limited by these examples in any way.

[Measurement Method]

(1) Structure of Compound

The structure of the compound was verified by carrying out 1H-NMR measurement under the following conditions using a product from Bruker, "Advance 600 II spectrometer".

Frequency: 400 MHz

Solvent: $CDCl_3$ or $d_6$-DMSO

Internal standard: TMS

Measurement temperature: 23° C.

(2) Measurement of Contents of Various Metals (Impurities) Contained in Precipitates ICP-MS was used to measure the contents of various metals (Na, K, Ca, Mg, Fe, Cu, Ni, Sn, Ag, Mo, Mn, Zn, Co, Al, Pb, Cr, and Ti) contained in the precipitate under the following measurement conditions.

Apparatus: triple quadrupole ICP-MS (inductively coupled plasma mass spectrometer) (8900 ICP-QQQ (trade name) manufactured by Agilent Technologies, Inc.

(Synthesis Example 1-1) Synthesis of MAC-2H35I and Ac-MAC-2H35I

Into 900 ml of methanol, 90 g (0.24 mol) of 3,5-diiodosalicylaldehyde was dissolved, and 22.8 g (0.60 mol) of $NaBH_4$ was added thereto at 10° C. or lower. Subsequently, the mixture was stirred and reacted under ice-cooling for 3 hours, then stirred at 25° C. for 16 hours to react, and methanol was distilled off under reduced pressure and concentrated. Water and ethyl acetate were added to the concentrate, and the organic phase was extracted. The organic phase was dried over magnesium sulfate added, and the solvent was distilled off under reduced pressure to obtain a crude product of 2-hydroxy-3,5-diiodobenzyl alcohol. The obtained crude product of 2-hydroxy-3,5-diiodobenzyl alcohol was purified by column chromatography to obtain 82.5 g (yield: 91%) of 2-hydroxy-3,5-diiodobenzyl alcohol shown below.

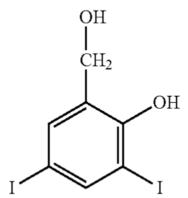

(2-hydroxy-3,5-diiodobenzyl alcohol)

In 100 mL of dichloromethane, 10 g (27 mmol) of 2-hydroxy-3,5-diiodobenzyl alcohol obtained above was dissolved, 3.1 g (39 mmol) of pyridine was added under ice-cooling, and 4.1 g (27 mmol) of methacrylic anhydride was added dropwise thereto. Subsequently, the mixture was stirred and reacted under ice-cooling for 4 hours and at room temperature for 18 hours. After completion of the reaction, water was added to the reaction liquid, and the mixture was washed with aqueous sodium hydrogen carbonate solution. The organic phase was dried over magnesium sulfate, concentrated, and purified by column chromatography to obtain 9 g (yield: 88%) of the objective product MAC-2H35I shown below.

When the obtained compound (MAC-2H35I) was subjected to NMR measurement under the above measurement conditions, the following peaks were detected, and it was confirmed that the compound had a chemical structure represented by the formula (MAC-2H35I):

δ (ppm) ($CDCl_3$): 7.2-8.0 (2H, Ph), 7.6 (1H, —OH), 6.2 (1H, $=CH_2$), 5.7 (1H, $=CH_2$), 5.1 (2H, $—CH_2—$), 2.0 (3H, $—CH_3$)

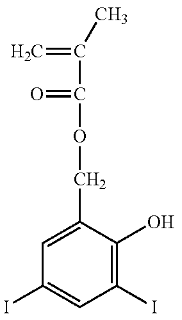

(MAC-2H35I)

In 100 mL of dimethylsulfoxide, 9 g (20 mmol) of MAC-2H35I obtained above was dissolved, and 2 eq. of acetic anhydride and 1 eq. of sulfuric acid were added thereto. Subsequently, the temperature was elevated to 80° C., and the mixture was stirred and reacted for 3 hours. After completion of the reaction, water was added to the reaction liquid, and the mixture was washed with aqueous sodium hydrogen carbonate solution. The organic phase was dried over magnesium sulfate, concentrated, and purified by column chromatography to obtain 6 g (yield: 60%) of the objective product Ac-MAC-2H35I shown below.

When the obtained compound (Ac-MAC-2H35I) was subjected to NMR measurement under the above measurement conditions, the following peaks were detected, and it was confirmed that the compound had a chemical structure represented by the formula (Ac-MAC-2H35I):

δ (ppm) ($CDCl_3$): 7.2-8.0 (2H, Ph), 6.2 (1H, $=CH_2$), 5.7 (1H, $=CH_2$), 5.1 (2H, $—CH_2—$), 2.2 (3H, $—CH_3$), 2.0 (3H, $—CH_3$)

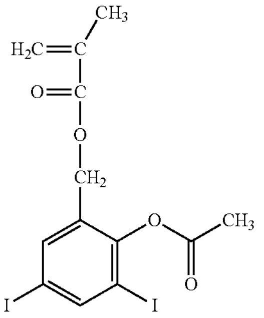

(Ac-MAC-2H35I)

(Synthesis Example 2-1) Synthesis of MAC-4H35I and Ac-MAC-4H35I

In 2.8 L of ethanol, 128 g (0.78 mol) of calcium chloride and 91.3 g (2.4 mol) of $NaBH_4$ were dissolved, and 410 g (1.1 mol) of 4-hydroxy-3,5-diiodobenzaldehyde was added thereto under ice-cooling. After the reaction was carried out by stirring at 25° C. for 18 hours, 10 L of water was added to the mixture, the pH was adjusted to 2.5 with hydrochloric acid, and the precipitate was filtered, washed with water, and dried to obtain 401 g (yield: 97%) of 4-hydroxy-3,5-diiodobenzyl alcohol shown below.

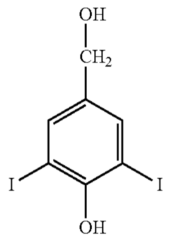

(4-hydroxy-3,5-diiodobenzyl alcohol)

In 2.8 L of toluene, 400 g (1.06 mol) of 4-hydroxy-3,5-diiodobenzyl alcohol obtained above was dissolved, and 916 g (10.6 mol) of methacrylic anhydride, 20 g of paratoluenesulfonic acid monohydrate (0.105 mol), and 13 mg (0.01 mmol) of 4-methoxyphenol were added thereto, followed by stirring at 110° C. under reflux for 2 hours. After the reaction, 4 L of water was added to the reaction mixture to dry the organic layer, and the organic layer was purified by recrystallization twice with hexane to obtain 158 g (yield: 33%) of the objective product MAC-4H35I shown below.

When the obtained compound (MAC-4H35I) was subjected to NMR measurement under the above measurement conditions, the following peaks were detected, and it was confirmed that the compound had a chemical structure represented by the formula (MAC-4H35I):

δ (ppm) ($CDCl_3$): 9.7 (1H, —OH), 7.8 (2H, Ph), 6.7 (1H, $=CH_2$), 5.0 (1H, $=CH_2$), 5.0 (2H, $—CH_2—$), 1.9 (3H, $—CH_3$)

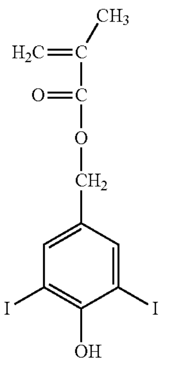

(MAC-4H35I)

In 100 mL of toluene, 50.0 g of the obtained compound (MAC-4H35I) was dissolved. Thereafter, a separation treatment using 100 mL of a 0.1 N sulfuric acid solution was performed 2 times, and then a separation treatment using 100 mL of a 0.1 mmol/L oxalic acid solution was performed 1 time. Thereafter, a water washing treatment using 100 mL of ultrapure water was carried out a plurality of times until the pH of the aqueous layer recovered after the separation treatment reached 4 or more. The obtained toluene solution was concentrated to obtain a toluene solution having a solid content concentration of 50%. To the solution, 1 L of hexane was added to obtain 41.1 g of precipitate (MAC-4H35Ip).

When the obtained precipitate was subjected to NMR measurement under the above measurement conditions, and it was confirmed that the precipitate was identical to the compound (MAC-4H35I).

When the contents of metals (impurity) in the obtained precipitate were measured under the above measurement conditions, it was confirmed that the content was 1 ppb or less in any of the following metals: Na, K, Ca, Mg, Fe, Cu, Ni, Sn, Ag, Mo, Mn, Zn, Co, Al, Pb, Cr and Ti.

In 100 mL of dimethylsulfoxide, 9 g (20 mmol) of MAC-4H35I obtained above was dissolved, and 2 eq. of acetic anhydride and 1 eq. of sulfuric acid were added thereto. Subsequently, the temperature was elevated to 80° C., and the mixture was stirred and reacted for 3 hours. After completion of the reaction, water was added to the reaction liquid, and the mixture was washed with aqueous sodium hydrogen carbonate solution. The organic phase was dried over magnesium sulfate, concentrated, and purified by column chromatography to obtain 6 g (yield: 60%) of the objective product Ac-MAC-4H35I shown below.

When the obtained compound (Ac-MAC-4H35I) was subjected to NMR measurement under the above measurement conditions, the following peaks were detected, and it was confirmed that the compound had a chemical structure represented by the formula (Ac-MAC-4H35I):

7.8 (2H, Ph), 6.7 (1H, $=CH_2$), 5.0 (1H, $=CH_2$), 5.0 (2H, $-CH_2-$), 2.0 (3H, $-CH_3$), 1.9 (3H, $-CH_3$)

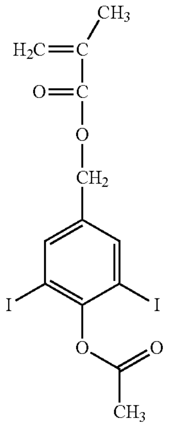

(Ac-MAC-4H35I)

In 100 mL of toluene, 50.0 g of the obtained compound (Ac-MAC-4H35I) was dissolved. Thereafter, a separation treatment using 100 mL of a 0.1 N sulfuric acid solution was performed 2 times, and then a separation treatment using 100 mL of a 0.1 mmol/L oxalic acid solution was performed 1 time. Thereafter, a water washing treatment using 100 mL of ultrapure water was carried out a plurality of times until the pH of the aqueous layer recovered after the separation treatment reached 4 or more. The obtained toluene solution was concentrated to obtain a toluene solution having a solid content concentration of 50%. To the solution, 1 L of hexane was added to obtain 38.4 g of precipitate (Ac-MAC-4H35Ip).

When the obtained precipitate was subjected to NMR measurement under the above measurement conditions, and it was confirmed that the precipitate was identical to the compound (Ac-MAC-4H35I).

When the contents of metals (impurity) in the obtained precipitate were measured under the above measurement conditions, it was confirmed that the content was 1 ppb or less in any of the following metals: Na, K, Ca, Mg, Fe, Cu, Ni, Sn, Ag, Mo, Mn, Zn, Co, Al, Pb, Cr and Ti.

(Synthesis Example 3-1) Synthesis of ACLAC-2H35I and Ac-ACLAC-2H35I

In a 300 mL eggplant flask equipped with a Dean Stark and reflux tube, 10.2 g (27 mmol) of 2-hydroxy-3,5-diiodobenzyl alcohol obtained in Synthesis Example 1-1 was dissolved in 100 mL of toluene, 0.05 g (0.3 mmol) of p-toluene sulfonic acid was added under ice-cooling, and 2.9 g (27 mmol) of chloride acrylate was added dropwise thereto. Subsequently, the mixture was stirred and reacted under reflux conditions for 1 hour. After completion of the reaction, water was added to the reaction liquid, and the mixture was washed with aqueous sodium hydrogen carbonate solution. The organic phase was dried over magnesium sulfate, concentrated, and purified by column chromatography to obtain 9.3 g (yield: 73%) of the objective product ACLAC-2H35I shown below.

When the obtained compound (ACLAC-2H35I) was subjected to NMR measurement under the above measurement conditions, the following peaks were detected, and it was confirmed that the compound had a chemical structure represented by the formula (ACLAC-2H35I):

δ (ppm) ($CDCl_3$): 7.2-8.0 (2H, Ph), 9.6 (1H, $-OH$), 6.0 (1H, $=CH_2$), 6.6 (1H, $=CH_2$), 5.1 (2H, $-CH_2-$)

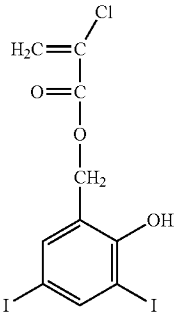

(ACLAC-2H35I)

In 100 mL of dimethylsulfoxide, 9.3 g (20 mmol) of ACLAC-2H35I obtained above was dissolved, and 2 eq. of acetic anhydride and 1 eq. of sulfuric acid were added thereto. Subsequently, the temperature was elevated to 80° C., and the mixture was stirred and reacted for 3 hours. After completion of the reaction, water was added to the reaction liquid, and the mixture was washed with aqueous sodium hydrogen carbonate solution. The organic phase was dried over magnesium sulfate, concentrated, and purified by column chromatography to obtain 5.1 g (yield: 50%) of the objective product Ac-ACLAC-2H35I shown below.

When the obtained compound (Ac-ACLAC-2H35I) was subjected to NMR measurement under the above measurement conditions, the following peaks were detected, and it was confirmed that the compound had a chemical structure represented by the formula (Ac-ACLAC-2H35I):

δ (ppm) ($CDCl_3$): 7.2-8.0 (2H, Ph), 6.0 (1H, $=CH_2$), 6.6 (1H, $=CH_2$), 5.1 (2H, $-CH_2-$), 2.0 (3H, $-CH_3$)

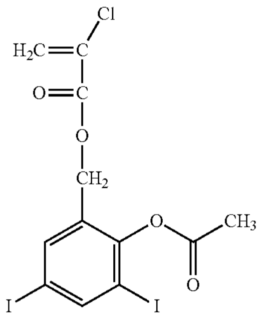

(Ac-ACLAC-2H35I)

(Synthesis Example 4-1) Synthesis of MAC-ADIOH and Ac-MAC-ADIOH

In 100 mL of toluene, 2.3 g (12.5 mmol) of 1,3,5-adamantanetriol (manufactured by Mitsubishi Gas Chemical) was dissolved, to which was added 28.1 g (125 mmol) of a 57% aqueous solution of hydrogen iodide, and the mixture was stirred at 80° C. for 13 hours to react. After the reaction, water was added, washing was performed with sodium hydrogen carbonate, and the organic layer was concentrated and then separated and purified by column chromatography to obtain 0.9 g of 3-iodo-1,5-dihydroxy-adamantane represented by the following formula:

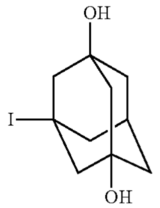

(3-iodo-1,5-dihydroxyadamantane)

In chloroform, 4.04 g (10 mmol) of 5-iodo-1,3-dihydroxyadamantane was dissolved, 0.96 g (12 mmol) of pyridine was added under ice-cooling, and 1.25 g (12 mmol) of methacrylic acid chloride was added dropwise thereto. Subsequently, the mixture was stirred and reacted under ice-cooling for 1 hour and at room temperature for 3 hours. After completion of the reaction, water was added to the reaction liquid, and the mixture was washed with saturated aqueous sodium hydrogen carbonate solution. The organic phase was dried over sodium sulfate, concentrated, and purified by column chromatography to obtain 3.5 g of the objective product MAC-ADIOH shown below.

When the obtained compound (MAC-ADIOH) was subjected to NMR measurement under the above measurement conditions, the following peaks were detected, and it was confirmed that the compound had a chemical structure represented by the formula (MAC-ADIOH):

δ (ppm) (d-DMSO): 6.4-6.5 (2H, $=CH_2$), 1.5-3.9 (14H, Ad-H, $-C(CH_3)=C$), 4.5 (1H, —OH)

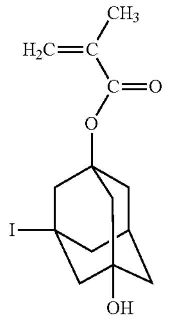

(MAC-ADIOH)

In 100 mL of methyl ethyl ketone, 50.0 g of the obtained compound (MAC-ADIOH) was dissolved. Thereafter, a separation treatment using 100 mL of a 0.1 N sulfuric acid solution was performed 2 times, and then a separation treatment using 100 mL of a 0.1 mmol/L oxalic acid solution was performed 1 time. Thereafter, a water washing treatment using 100 mL of ultrapure water was carried out a plurality of times until the pH of the aqueous layer recovered after the separation treatment reached 4 or more. The obtained methyl ethyl ketone solution was concentrated to obtain a methyl ethyl ketone solution having a solid content concentration of 50%. To the solution, 1 L of hexane was added to obtain 41.1 g of precipitate (MAC-ADIOHp).

When the obtained precipitate was subjected to NMR measurement under the above measurement conditions, and it was confirmed that the precipitate was identical to the compound (MAC-ADIOH).

When the contents of metals (impurity) in the obtained precipitate were measured under the above measurement conditions, it was confirmed that the content was 1 ppb or less in any of the following metals: Na, K, Ca, Mg, Fe, Cu, Ni, Sn, Ag, Mo, Mn, Zn, Co, Al, Pb, Cr and Ti.

In 100 mL of dimethylsulfoxide, 3.5 g (10 mmol) of MAC-ADIOH obtained above was dissolved, and 2 eq. of acetic anhydride and 1 eq. of sulfuric acid were added thereto. Subsequently, the temperature was elevated to 80° C., and the mixture was stirred and reacted for 3 hours. After completion of the reaction, water was added to the reaction liquid, and the mixture was washed with aqueous sodium hydrogen carbonate solution. The organic phase was dried over magnesium sulfate, concentrated, and purified by column chromatography to obtain 2.4 g (yield: 60%) of the objective product Ac-MAC-ADIOH shown below.

When the obtained compound (Ac-MAC-ADIOH) was subjected to NMR measurement under the above measurement conditions, the following peaks were detected, and it was confirmed that the compound had a chemical structure represented by the formula (Ac-MAC-ADIOH):

δ (ppm) ($CDCl_3$) 6.4-6.5 (2H, $=CH_2$), 1.5-3.9 (14H, Ad-H, $-C(CH_3)=C$), 2.0 (3H, $-CH_3$)

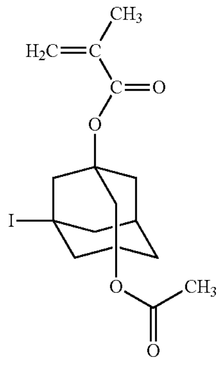

(Ac-MAC-ADIOH)

In 100 mL of methyl ethyl ketone, 50.0 g of the obtained compound (Ac-MAC-ADIOH) was dissolved. Thereafter, a separation treatment using 100 mL of a 0.1 N sulfuric acid solution was performed 2 times, and then a separation treatment using 100 mL of a 0.1 mmol/L oxalic acid solution was performed 1 time. Thereafter, a water washing treatment using 100 mL of ultrapure water was carried out a plurality of times until the pH of the aqueous layer recovered after the separation treatment reached 4 or more. The obtained methyl ethyl ketone solution was concentrated to obtain a methyl ethyl ketone solution having a solid content concentration of 50%. To the solution, 1 L of hexane was added to obtain 41.1 g of precipitate (Ac-MAC-ADIOHp).

When the obtained precipitate was subjected to NMR measurement under the above measurement conditions, and it was confirmed that the precipitate was identical to the compound (Ac-MAC-ADIOH).

When the contents of metals (impurity) in the obtained precipitate were measured under the above measurement conditions, it was confirmed that the content was 1 ppb or less in any of the following metals: Na, K, Ca, Mg, Fe, Cu, Ni, Sn, Ag, Mo, Mn, Zn, Co, Al, Pb, Cr and Ti.

(Synthesis Example 5-1) Synthesis of MAC-ADI4H4M

In 100 mL of toluene, 2.3 g (12.5 mmol) of 4-methyl-adamantane-1,4-diol was dissolved, to which was added 11.2 g (50 mmol) of a 57% aqueous solution of hydrogen iodide, and the mixture was stirred at 80° C. for 8 hours to react. After the reaction, water was added, washing was performed with sodium hydrogen carbonate, and the organic layer was concentrated and then separated and purified by column chromatography to obtain 1.1 g of 1-iodo-4-methyl-4-hydroxyadamantane represented by the following formula:

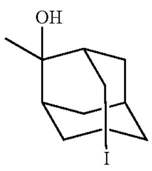

(1-iodo-4-methyl-4-hydroxyadamantane)

In chloroform, 2.92 g (10 mmol) of 1-iodo-4-methyl-4-dihydroxyadamantane was dissolved, 0.96 g (12 mmol) of pyridine was added under ice-cooling, and 1.25 g (12 mmol) of methacrylic acid chloride was added dropwise thereto. Subsequently, the mixture was stirred and reacted under ice-cooling for 1 hour and at room temperature for 3 hours. After completion of the reaction, water was added to the reaction liquid, and the mixture was washed with saturated aqueous sodium hydrogen carbonate solution. The organic phase was dried over sodium sulfate, concentrated, and purified by column chromatography to obtain 3.1 g of the objective product MAC-ADI4H4M shown below.

When the obtained compound (MAC-ADI4H4M) was subjected to NMR measurement under the above measurement conditions, the following peaks were detected, and it was confirmed that the compound had a chemical structure represented by the formula (MAC-ADI4H4M):

δ (ppm) (d-DMSO): 6.4-6.5 (2H, $=CH_2$), 1.2-2.4 (19H, Ad-H, Ad-$CH_3$, $—C(CH_3)=C$)

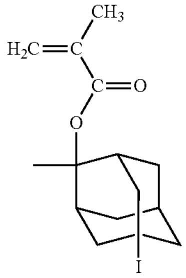

(MAC-ADI4H4M)

(Synthesis Working Example 1) Synthesis of P-Ac-MAC-2H35I Resin

In 45 mL of tetrahydrofuran, 2.4 g of Ac-MAC-2H35I obtained in Synthesis Example 1-1, 3.0 g of 2-methyl-2-adamantyl methacrylate, 2.0 g of γ-butyrolactone methacrylate and 1.5 g of 3-hydroxy-1-adamantyl methacrylate were dissolved, and 0.20 g of azobisisobutyronitrile was added thereto. After refluxing for 12 hours, the reaction solution was added dropwise to 2 L of n-heptane. The deposited resin was filtered off and dried under reduced pressure to obtain a white powdery resin represented by the following chemical formula (P-Ac-MAC-2H35I). The resin had a molecular weight (Mw) of 15400 and a dispersity (Mw/Mn) of 2.2. As a result of measuring 13C-NMR, the composition ratio (molar ratio) in the following chemical formula (P-Ac-MAC-ADIOH) was a:b:c:d=40:30:15:15. Although the chemical formula (P-Ac-MAC-2H35I) shown below is briefly described in order to indicate the ratio of each constituent unit, P-Ac-MAC-2H35I is not a block copolymer in which each constituent unit forms an independent block.

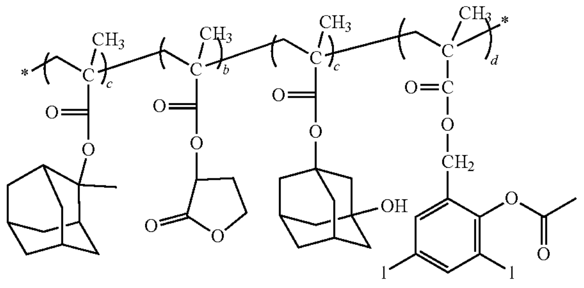

(P-Ac-MAC-2H35I)

(Synthesis Working Example 2) Synthesis of P-Ac-MAC-4H35I Resin

In the same manner as in Synthesis Working Example 1 except that Ac-MAC-4H35I (2.4 g) obtained in Synthesis Example 2-1 was used instead of Ac-MAC-2H35I (2.4 g) of Synthesis Working Example 1, a resin represented by the following chemical formula (P-Ac-MAC-4H35I) was obtained. The resin had a molecular weight (Mw) of 15000 and a dispersity (Mw/Mn) of 2.1. As a result of measuring $^{13}$C-NMR, the composition ratio (molar ratio) in the following chemical formula (P-Ac-MAC-4H35I) was a:b:c:d=40:30:15:15. Although the chemical formula (P-Ac-MAC-4H35I) shown below is briefly described in order to indicate the ratio of each constituent unit, P-Ac-MAC-4H35I is not a block copolymer in which each constituent unit forms an independent block.

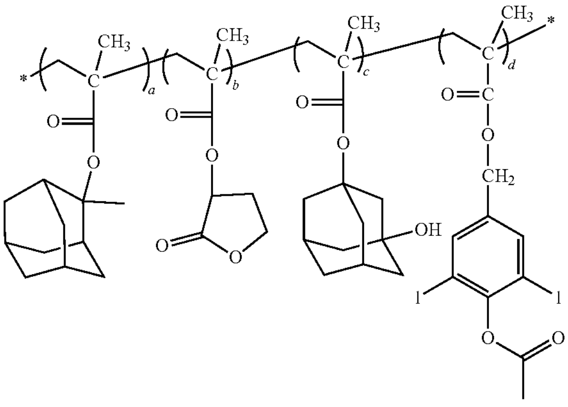

(P-Ac-MAC-4H35I)

(Synthesis Working Example 3) Synthesis of P-Ac-MAC-ADIOH1 Resin

In the same manner as in Synthesis Working Example 1 except that Ac-MAC-ADIOH (2.0 g) obtained in Synthesis Example 4-1 was used instead of Ac-MAC-2H35I (2.4 g) of Synthesis Working Example 1, a resin represented by the following chemical formula (P-Ac-MAC-ADIOH1) was obtained. The resin had a molecular weight (Mw) of 15800 and a dispersity (Mw/Mn) of 1.8. As a result of measuring $^{13}$C-NMR, the composition ratio (molar ratio) in the following chemical formula (P-Ac-MAC-ADIOH1) was a:b:c:d=40:30:15:15. Although the chemical formula (P-Ac-MAC-ADIOH1) shown below is briefly described in order to indicate the ratio of each constituent unit, P-Ac-MAC-ADIOH1 is not a block copolymer in which each constituent unit forms an independent block.

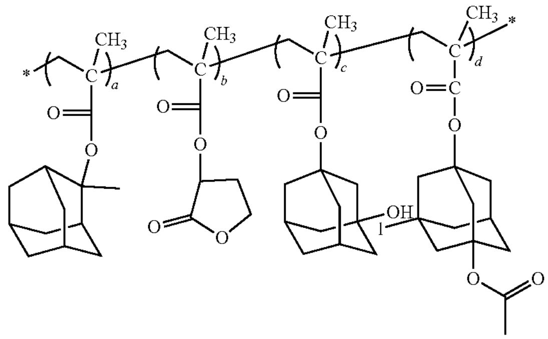

(P-Ac-MAC-ADIOH1)

(Synthesis Working Example 4) Synthesis of P-Ac-MAC-ADIOH2 Resin

In the same manner as in Synthesis Working Example 1 except that 4.7 g of MAC-ADI4H4M obtained in Synthesis Example 5-1, 2.0 g of γ-butyrolactone methacrylate, and 4.0 g of Ac-MAC-ADIOH obtained in Synthesis Example 4-1 were used as monomers (raw materials), a resin represented by the following chemical formula (P-Ac-MAC-ADIOH2) was obtained. The resin had a molecular weight (Mw) of 15800 and a dispersity (Mw/Mn) of 2.3. As a result of measuring $^{13}$C-NMR, the composition ratio (molar ratio) in the following chemical formula (P-Ac-MAC-ADIOH2) was a:b:c=40:30:30. Although the chemical formula (P-Ac-MAC-ADIOH2) shown below is briefly described in order to indicate the ratio of each constituent unit, P-Ac-MAC-ADIOH2 is not a block copolymer in which each constituent unit forms an independent block.

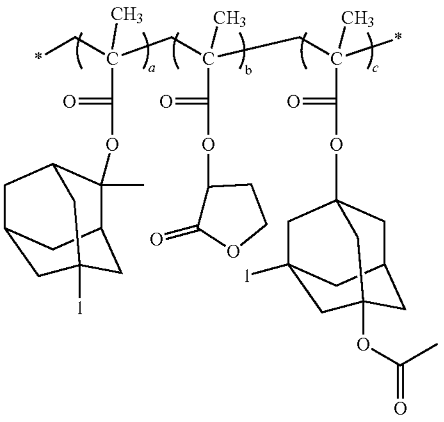

(P-Ac-MAC-ADIOH2)

(Synthesis Working Example 5) Synthesis of P-Ac-MAC-ADIOH3 Resin

In the same manner as in Synthesis Working Example 1 except that 4.7 g of MAC-ADI4H4M obtained in Synthesis Example 5-1, 2.0 g of γ-butyrolactone methacrylate, 0.6 g of 4-hydroxystyrene, and 2.0 g of Ac-MAC-ADIOH obtained in Synthesis Example 4-1 were used as monomers (raw materials), a resin represented by the following chemical formula (P-Ac-MAC-ADIOH3) was obtained. The resin had a molecular weight (Mw) of 15500 and a dispersity (Mw/Mn) of 2.1. As a result of measuring $^{13}C$-NMR, the composition ratio (molar ratio) in the following chemical formula (P-Ac-MAC-ADIOH3) was a:b:c:d=40:30:15:15. Although the chemical formula (P-Ac-MAC-ADIOH3) shown below is briefly described in order to indicate the ratio of each constituent unit, P-Ac-MAC-ADIOH3 is not a block copolymer in which each constituent unit forms an independent block.

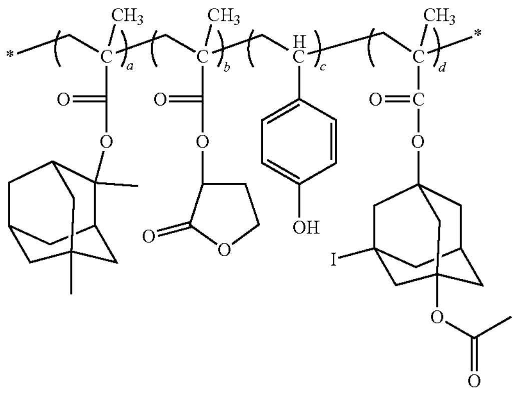

(P-Ac-MAC-ADIOH3)

(Synthesis Working Example 6) Synthesis of P-Ac-MAC-ADIOH4 Resin

In the same manner as in Synthesis Working Example 1 except that 4.7 g of MAC-ADI4H4M obtained in Synthesis Example 5-1, 2.0 g of γ-butyrolactone methacrylate, 1.9 g of 3,5-diiodo-4-hydroxystyrene, and 2.0 g of Ac-MAC-ADIOH obtained in Synthesis Example 4-1 were used as monomers (raw materials), a resin represented by the following chemical formula (P-Ac-MAC-ADIOH4) was obtained. The resin had a molecular weight (Mw) of 15600 and a dispersity (Mw/Mn) of 2.3. As a result of measuring $^{13}C$-NMR, the composition ratio (molar ratio) in the following chemical formula (P-Ac-MAC-ADIOH4) was a:b:c:d=40:30:15:15. Although the chemical formula (P-Ac-MAC-ADIOH4) shown below is briefly described in order to indicate the ratio of each constituent unit, P-Ac-MAC-ADIOH4 is not a block copolymer in which each constituent unit forms an independent block.

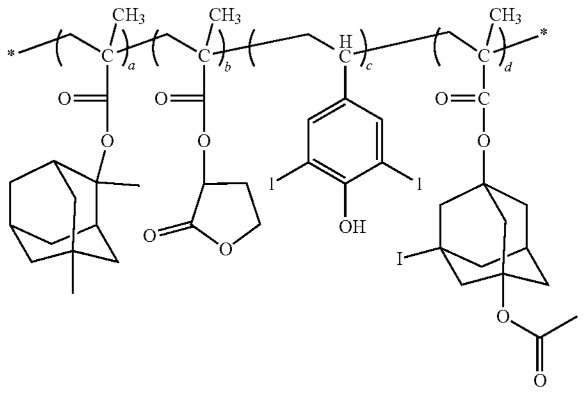

(P-Ac-MAC-ADIOH4)

(Synthesis Comparative Example 1) Synthesis of P-AC-1 Resin

A resin represented by the following chemical formula (P-AC-1) was obtained in the same manner as in Synthesis Working Example 1 except that Ac-MAC-2H35I was not used. The resin had a molecular weight (Mw) of 13500 and a dispersity (Mw/Mn) of 2.3.

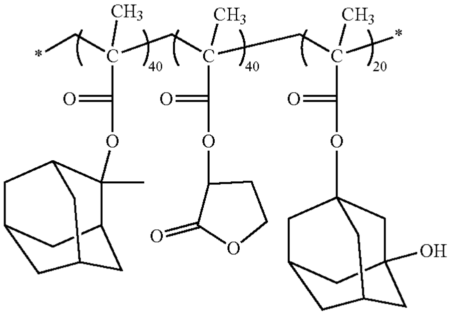

(P-AC-1)

In the above formula (P-AC-1), "40", "40", and "20" indicate molar ratios of the constituent units. Although the formula (P-AC-1) is briefly described in order to indicate the ratio of each constituent unit, P-AC-1 is not a block copolymer in which each constituent unit forms an independent block.

Example 1

The P-Ac-MAC-2H35I resin-solution obtained in Synthesis Working Example 1 was applied onto a silicon wafer and baked at 110 to 130° C. for 60 seconds to form a photoresist layer having a film thickness of 100 nm. Here, a resin solution was prepared by mixing 5 parts by mass of P-Ac-MAC-2H35I resin, 1 part by mass of triphenylsulfonium nonafluoromethanesulfonate, 0.1 part by mass of tributylamine, and 92 parts by mass of propylene glycol monomethyl ether acetate (PGMEA).

Subsequently, the photoresist layer was exposed using an electron beam lithography system (manufactured by ELIONIX INC.; ELS-7500 (trade name), 50 keV), baked (PEB, post exposure bake) at 115° C. for 90 seconds, and developed at 23° C. for 60 seconds using a 2.38 mass % tetramethylammonium hydroxide (TMAH) aqueous solution to obtain a positive type pattern. From the obtained pattern, resolution (50 nm L/S) was evaluated by a scanning electron microscope (S-4800 manufactured by Hitachi High-Technologies Corporation).

The obtained resin solution was filled in a light-shielding bottle and stored at 40° C. for 30 days. Thereafter, with respect to the resin solution after storage, a change with time of the resin solution was evaluated by the following method.

That is, the resin solutions before and after storage were respectively applied to different silicon wafers by a spin coater, and heated on a hotplate at 110° C. for 1 minute to form a resist layer having a film thickness of 80 nm.

Next, each of the obtained resist layers was subjected to maskless shot exposure with different exposure amounts from 1 $mJ/cm^2$ to 80$mJ/cm^2$ by 1$mJ/cm^2$ using an extreme ultraviolet (EUV) exposure apparatus "EUVS-7000" (trade name, manufactured by Lithotech Japan Co., Ltd.) to obtain a wafer having a portion where the resist layer was exposed at different exposure amounts by 1$mJ/cm^2$. Thereafter, the entire surface of the wafer was baked (PEB) at 110° C. for 90 seconds and developed using isoamyl acetate at 23° C. for 60 seconds. The film thickness of each of the 80 portions after development was measured by an optical interference film thickness meter "VM 3200" (trade name, manufactured by SCREEN Semiconductor Solutions Co., Ltd.), profile data of the film thickness with respect to the exposure amount was obtained, and the exposure amount at which the gradient of the film thickness variation amount with respect to the exposure amount became the largest was calculated as a sensitivity value ($mJ/cm^2$), and used as an index of the EUV sensitivity of the resist layer.

Then, using the sensitivity values before and after the storage, the variation rate was determined by the following index.

"variation rate"=[("sensitivity value of resin solution before storage"−"sensitivity value of resin solution after storage")/"sensitivity value of resin solution before storage"]×100

Using the obtained variation rate, the change with time of the resin solution was evaluated as follows. A variation rate of less than 2% means that the storage stability of the resist composition is good, defects in fine processing are prevented, and productivity is excellent.

A: variation rate is less than 2%

B: variation rate is 2% or more

The results of resolution, sensitivity, and change with time are shown in Table 1.

Examples 2 to 6

Resin solutions were prepared in the same manner as in Example 1 except that the resins obtained in Synthesis Working Examples 2 to 6 were used instead of the P-Ac-MAC-2H35I resin, and photoresist layers were formed using the resin solutions. Next, using each of the photoresist layers, resolution and sensitivity were evaluated in the same manner as in Example 1. Further, using each of the resin solutions, the change with time was evaluated in the same manner as in Example 1. The results are shown in Table 1.

Comparative Example 1

A Resin solution was prepared in the same manner as in Example 1 except that the P-AC-1 resin obtained in Synthesis Comparative Example 1 was used instead of the P-Ac-MAC-2H35I resin, and a photoresist layer was formed using the resin solution. Next, using the photoresist layer, resolution and sensitivity were evaluated in the same manner as in Example 1. Further, using the resin solution, the change with time was evaluated in the same manner as in Example 1. The results are shown in Table 1.

TABLE 1

| | Resin | Resolution | Sensitivity | Change with time |
|---|---|---|---|---|
| Example 1 | P-AC-MAC-2H35I | 40 nm L/S | 15 $\mu C/cm^2$ | A |
| Example 2 | P-AC-MAC-4H35I | 40 nm L/S | 15 $\mu C/cm^2$ | A |
| Example 3 | P-AC-MAC-ADIOH1 | 40 nm L/S | 20 μC/cm2 | A |
| Example 4 | P-AC-MAC-ADIOH2 | 40 nm L/S | 15 $\mu C/cm^2$ | A |
| Example 5 | P-AC-MAC-ADIOH3 | 40 nm L/S | 10 $\mu C/cm^2$ | A |
| Example 6 | P-AC-MAC-ADIOH4 | 40 nm L/S | 10 $\mu C/cm^2$ | A |
| Comparative Example 1 | P-AC-1 | 80 nm L/S | 26 $\mu C/cm^2$ | B |

As described above, the iodine-containing (meth)acrylate compound and the iodine-containing (meth)acrylate (co) polymer of the present embodiment are excellent in stability, and can provide a composition capable of forming a resist film having high sensitivity and high resolution.

(Synthesis Working Example 7) Synthesis of P-MAC-2H35I Resin

In 45 mL of tetrahydrofuran, 5.0 g of P-Ac-MAC-2H35I resin obtained in Synthesis Working Example 1 was dissolved, and 0.5 g of 37% by mass of hydrochloric acid was added to the solution. After stirring at 50° C. for 5 hours, 45 mL of butyl acetate and 45 mL of water were added to the reaction solution, and liquid separation and purification was performed. Further, the organic layer was concentrated under reduced pressure, redissolved in propylene glycol monomethyl ether, and poured into a large amount of water. The deposited resin was filtered off and dried under reduced pressure to obtain a white powdery resin represented by the following chemical formula (P-MAC-2H35I). The conversion of acetyl group to hydroxy group was confirmed by 1H-NMR. The resin had a molecular weight (Mw) of 14400 and a dispersity (Mw/Mn) of 2.2. As a result of measuring $^{13}C$-NMR, the composition ratio (molar ratio) in the following chemical formula (P-MAC-2H35I) was a:b:c:d=40:30:15:15. Although the chemical formula (P-MAC-2H35I) shown below is briefly described in order to indicate the ratio of each constituent unit, P-MAC-2H35I is not a block copolymer in which each constituent unit forms an independent block.

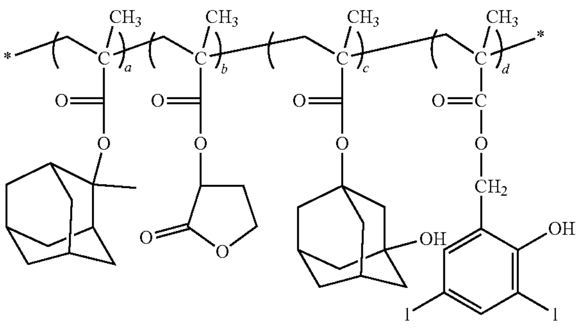

(P-MAC-2H351)

(Synthesis Working Example 8) Synthesis of P-MAC-4H35I Resin

A P-MAC-4H35I resin represented by the following structural formula was synthesized in the same manner as in Synthesis Working Example 7 except that the P-Ac-MAC-4H35I resin obtained in Synthesis Working Example 2 was used instead of the P-Ac-MAC-2H35I resin. The conversion of acetyl group to hydroxy group was confirmed by $^1$H-NMR. As a result of measuring $^{13}$C-NMR, the composition ratio (molar ratio) in the following chemical formula (P-MAC-4H35I) was a:b:c:d=40:30:15:15. Although the chemical formula (P-MAC-4H35I) shown below is briefly described in order to indicate the ratio of each constituent unit, P-MAC-4H35I is not a block copolymer in which each constituent unit forms an independent block.

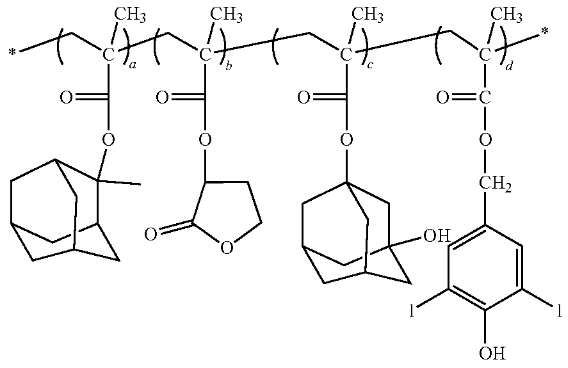

(P-MAC-4H35I)

(Synthesis Working Example 9) Synthesis of P-MAC-ADIOH1 Resin

A P-MAC-ADIOH1 resin represented by the following structural formula was synthesized in the same manner as in Synthesis Working Example 7 except that the P-Ac-MAC ADIOH1 resin obtained in Synthesis Working Example 3 was used instead of the P-Ac-MAC-2H35I resin. The conversion of acetyl group to hydroxy group was confirmed by 1H-NMR. As a result of measuring $^{13}$C-NMR, the composition ratio (molar ratio) in the following chemical formula (P-MAC-ADIOH1) was a:b:c:d=40:30:15:15. Although the chemical formula (P-MAC-ADIOH1) shown below is briefly described in order to indicate the ratio of each constituent unit, P-MAC-ADIOH1 is not a block copolymer in which each constituent unit forms an independent block.

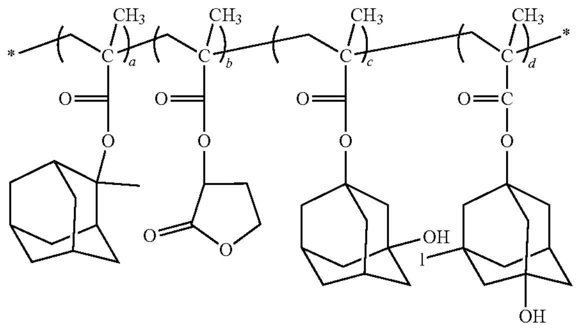

(P-MAC-ADIOH1)

(Synthesis Working Example 10) Synthesis of P-MAC-ADIOH2 Resin

A P-MAC-ADIOH2 resin represented by the following structural formula was synthesized in the same manner as in Synthesis Working Example 7 except that the P-Ac-MAC ADIOH2 resin obtained in Synthesis Working Example 4 was used instead of the P-Ac-MAC-2H35I resin. The conversion of acetyl group to hydroxy group was confirmed by 1H-NMR. As a result of measuring $^{13}$C-NMR, the composition ratio (molar ratio) in the following chemical formula (P-MAC-ADIOH2) was a:b:c=40:30:30. Although the chemical formula (P-MAC-ADIOH2) shown below is briefly described in order to indicate the ratio of each constituent unit, P-MAC-ADIOH2 is not a block copolymer in which each constituent unit forms an independent block.

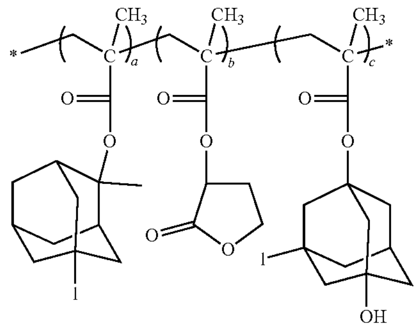

(P-MAC-ADIOH2)

(Synthesis Working Example 11) Synthesis of P-MAC-ADIOH3 Resin

A P-MAC-ADIOH3 resin represented by the following structural formula was synthesized in the same manner as in Synthesis Working Example 7 except that the P-Ac-MAC ADIOH3 resin obtained in Synthesis Working Example 5 was used instead of the P-Ac-MAC-2H35I resin. The conversion of acetyl group to hydroxy group was confirmed by 1H-NMR. As a result of measuring $^{13}$C-NMR, the composition ratio (molar ratio) in the following chemical formula (P-MAC-ADIOH3) was a:b:c:d=40:30:15:15. Although the chemical formula (P-MAC-ADIOH3) shown below is briefly described in order to indicate the ratio of each constituent unit, P-MAC-ADIOH3 is not a block copolymer in which each constituent unit forms an independent block.

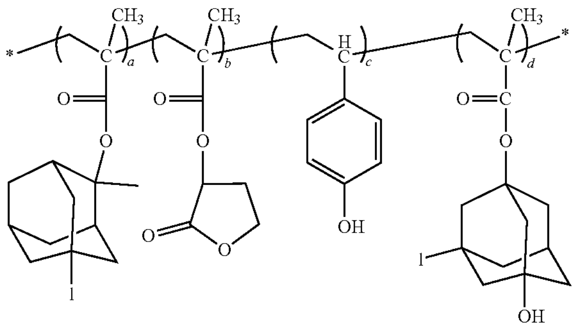

(P-MAC-ADIOH3)

(Synthesis Working Example 12) Synthesis of P-MAC-ADIOH4 Resin

A P-MAC-ADIOH4 resin represented by the following structural formula was synthesized in the same manner as in Synthesis Working Example 7 except that the P-Ac-MAC ADIOH4 resin obtained in Synthesis Working Example 6 was used instead of the P-Ac-MAC-2H35I resin. The conversion of acetyl group to hydroxy group was confirmed by 1H-NMR. As a result of measuring 13C-NMR, the composition ratio (molar ratio) in the following chemical formula (P-MAC-ADIOH4) was a:b:c:d=40:30:15:15. Although the chemical formula (P-MAC-ADIOH4) shown below is briefly described in order to indicate the ratio of each constituent unit, P-MAC-ADIOH4 is not a block copolymer in which each constituent unit forms an independent block.

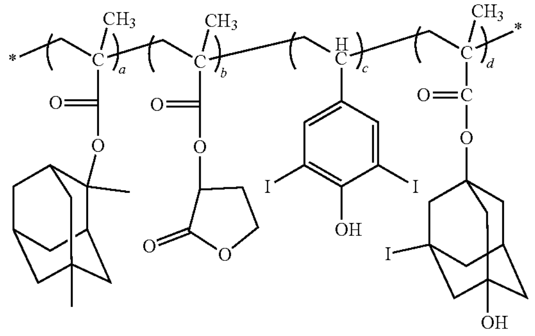

(P-MAC-ADIOH4)

The present application is based on Japanese Patent Application No. 2020-085904 filed on May 15, 2020, the contents of which are incorporated herein by reference.

INDUSTRIAL APPLICABILITY

According to the present embodiment, it is possible to provide a compound suitable for a resist material and having high stability, and capable of forming a film having high sensitivity and high resolution, a method for producing the compound, a (co)polymer, a composition, and a method for forming a resist pattern using the composition. It is also possible to provide a method for efficiently producing a (co)polymer having a hydroxy group useful for a resist material by using the compound and the (co)polymer.

The compound, (co)polymer, and composition of the present embodiment can be utilized widely and effectively in, for example, electrical insulating materials, resins for resists, encapsulation resins for semiconductors, adhesives for printed circuit boards, electrical laminates mounted in electric equipment, electronic equipment, industrial equipment, and the like, matrix resins of prepregs mounted in electric equipment, electronic equipment, industrial equipment, and the like, buildup laminate materials, resins for fiber-reinforced plastics, resins for encapsulation of liquid crystal display panels, coating materials, various coating agents, adhesives, coating agents for semiconductors, resins for resists for semiconductors, resins for resist underlayer film formation, and the like.

The invention claimed is:

1. An iodine-containing (meth) acrylate compound represented by formula (1):

(1)

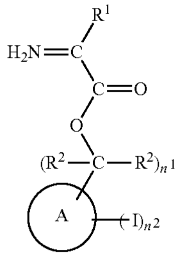

wherein $R^1$ represents a hydrogen atom, a methyl group, or halogen;

each $R^2$ independently represents a hydrogen atom, a linear organic group having 1 to 20 carbon atoms, a branched organic group having 3 to 20 carbon atoms, or a cyclic organic group having 3 to 20 carbon atoms;

A is adamantane or benzene having at least one acetoxy group;

$n^1$ represents 0 or 1; and $n^2$ represents an integer of 1 to 20.

2. The iodine-containing (meth) acrylate compound according to claim 1, wherein the formula (1) is formula (2):

(2)

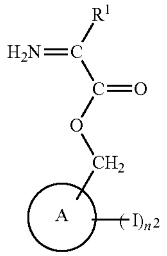

wherein $R^1$, A, and $n^2$ are the same as described above.

3. The iodine-containing (meth) acrylate compound according to claim 2, wherein the formula (2) is formula (3):

(3)

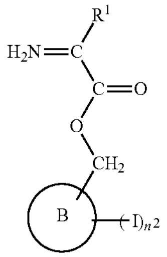

wherein B represents an organic group containing an aromatic group and having 5 to 30 carbon atoms, B is benzene having at least one acetoxy group, and $R^1$ and $n^2$ are as described above.

4. The iodine-containing (meth) acrylate compound according to claim 2, wherein the formula (2) is formula (3'):

(3')

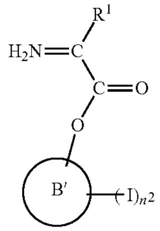

wherein B' represents an organic group containing an alicyclic ring and having 5 to 30 carbon atoms, B' is adamantane having at least one acetoxy group, and $R^1$ and $n^2$ are as described above.

5. The iodine-containing (meth) acrylate compound according to claim 1, wherein $n^2$ represents an integer of 2 to 20.

6. An iodine-containing (meth) acrylate (co) polymer comprising a constituent unit represented by formula (4):

(4)

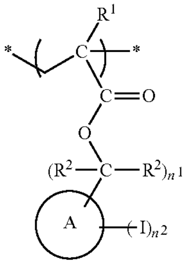

wherein $R^1$ represents a hydrogen atom, a methyl group, or halogen;

each $R^2$ independently represents a hydrogen atom, a linear organic group having 1 to 20 carbon atoms, a branched organic group having 3 to 20 carbon atoms, or a cyclic organic group having 3 to 20 carbon atoms;

A is adamantane or benzene having at least one acetoxy group;

$n^1$ represents 0 or 1;

$n^2$ represents an integer of 1 to 20; and the symbol * represents a bonding site to an adjacent constituent unit.

7. The iodine-containing (meth) acrylate (co) polymer according to claim 6, wherein the formula (4) is formula (5):

(5)

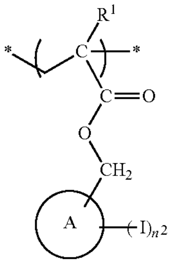

wherein $R^1$, $n^2$, A, and the symbol * are the same as described above.

8. The iodine-containing (meth) acrylate (co) polymer according to claim 7, wherein the formula (5) is formula (6):

(6)

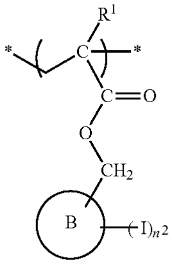

wherein B represents an organic group containing an aromatic group and having 5 to 30 carbon atoms, B is benzene having at least one acetoxy group, and $R^1$, $n^2$, and the symbol * are as described above.

9. The iodine-containing (meth) acrylate (co) polymer according to claim 7, wherein the formula (5) is formula (6'):

(6')

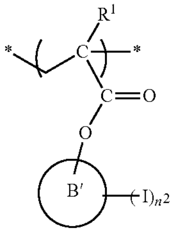

wherein B' represents an organic group containing an alicyclic ring and having 5 to 30 carbon atoms, B' is adamantane having at least one acetoxy group, and $R^1$, $n^2$, and the symbol * are as described above.

10. The iodine-containing (meth) acrylate (co) polymer according to claim 6, wherein $n^2$ represents an integer of 2 to 20.

11. A composition comprising the iodine-containing (meth) acrylate compound according to claim 1.

12. The composition according to claim 11, further comprising a solvent.

13. The composition according to claim 11, further comprising an acid generating agent.

14. The composition according to claim 11, further comprising an acid diffusion controlling agent.

15. A method for forming a resist pattern, comprising the steps of:

forming a film using the composition according to claim 11;

exposing the formed film; and removing an exposed portion of the exposed film using a developer to form a pattern.

* * * * *